(12) United States Patent
Miyazaki et al.

(10) Patent No.: US 11,401,276 B2
(45) Date of Patent: Aug. 2, 2022

(54) CHROMENE COMPOUND, CURABLE COMPOSITION COMPRISING THE COMPOUND, AND OPTICAL ARTICLE INCLUDING A CURED BODY OF THE CURABLE COMPOSITION

(71) Applicant: TOKUYAMA CORPORATION, Shunan (JP)

(72) Inventors: Masayuki Miyazaki, Shunan (JP); Junji Takenaka, Shunan (JP)

(73) Assignee: TOKUYAMA CORPORATION, Shunan (JP)

(*) Notice: Subject to any disclaimer, the term of this patent is extended or adjusted under 35 U.S.C. 154(b) by 241 days.

(21) Appl. No.: 16/629,277

(22) PCT Filed: Jul. 11, 2018

(86) PCT No.: PCT/JP2018/026175
§ 371 (c)(1),
(2) Date: Jan. 7, 2020

(87) PCT Pub. No.: WO2019/013249
PCT Pub. Date: Jan. 17, 2019

(65) Prior Publication Data
US 2020/0190106 A1 Jun. 18, 2020

(30) Foreign Application Priority Data

Jul. 14, 2017 (JP) ............... JP2017-138466
Nov. 2, 2017 (JP) ............... JP2017-213247

(51) Int. Cl.
*C07D 497/10* (2006.01)
*C07D 311/96* (2006.01)
(Continued)

(52) U.S. Cl.
CPC .......... *C07D 497/10* (2013.01); *C07D 311/96* (2013.01); *C08G 63/91* (2013.01);
(Continued)

(58) Field of Classification Search
CPC .. C07D 497/10; C07D 311/96; C07D 311/78; C08G 63/91; C08G 65/26; C08G 65/331; C08G 65/3315; C08G 65/33396; C08G 65/3346; C08K 5/357; C08K 5/46; C08K 5/0041; C08K 5/1545; C08K 5/378; C08K 2211/1425; C08K 2211/1433; C08K 2211/145; C08K 2211/1491; G02B 5/23; G02B 1/04; C09K 9/02
See application file for complete search history.

(56) References Cited

U.S. PATENT DOCUMENTS 5,961,892 A 10/1999 Gemert et al.
7,247,262 B2 7/2007 Evans et al.
(Continued)

FOREIGN PATENT DOCUMENTS

EP  2221325 A1  8/2010
JP  2002-524559 A  8/2002
(Continued)

OTHER PUBLICATIONS

Machine translation of JP 2008-273848 A, published Nov. 13, 2008.*
International Search Report for PCT/JP2018/026175 (PCT/ISA/210) dated Sep. 18, 2018.
Written Opinion of the International Searching Authority for PCT/JP2018/026175 (PCT/ISA/237) dated Sep. 18, 2018.
International Preliminary Report on Patentability and English translation of Written Opinion of the International Searching Aughority for PCT/JP2018/026175 (Forms PCT/IB/373 and PCT/ISA/237) dated Jan. 14, 2020.
(Continued)

*Primary Examiner* — Robert S Jones, Jr.
(74) *Attorney, Agent, or Firm* — Birch, Stewart, Kolasch & Birch, LLP

(57) ABSTRACT

A chromene compound having at least one indenonaphthopyran moiety which has a group forming a spiro ring together with the 13-position carbon atom and further an oligomer chain group selected from a polyalkylene oxide oligomer chain group having at least three recurring units and a polyester oligomer chain group having at least three recurring units, represented by the following formula and having reduced matrix dependence:

[CF 1]

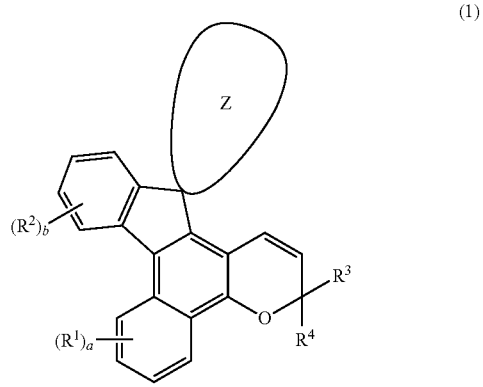

(1)

wherein $R^1$ and $R^2$ are each a group which may have an oligomer chain group, the ring Z bonded to the 13-position carbon atom of the chromene compound is a Spiro ring group, and $R^3$ and $R^4$ are each an aryl group or heteroaryl group which may have an oligomer chain group.
Preferably, the chromene compound has at least one oligomer chain group in the molecule.

15 Claims, No Drawings

(51) Int. Cl.

| | | |
|---|---|---|
| *C08G 65/26* | (2006.01) | |
| *C08K 5/357* | (2006.01) | |
| *C08K 5/46* | (2006.01) | |
| *C08G 63/91* | (2006.01) | |
| *C08G 65/331* | (2006.01) | |
| *C08G 65/333* | (2006.01) | |
| *C08G 65/334* | (2006.01) | |
| *G02B 5/23* | (2006.01) | |

(52) U.S. Cl.
CPC ......... *C08G 65/26* (2013.01); *C08G 65/3315* (2013.01); *C08G 65/3346* (2013.01); *C08G 65/33396* (2013.01); *C08K 5/357* (2013.01); *C08K 5/46* (2013.01); *G02B 5/23* (2013.01)

(56) References Cited

U.S. PATENT DOCUMENTS

| | | | |
|---|---|---|---|
| 7,807,075 B2 | 10/2010 | Evans et al. | |
| 8,865,029 B2 | 10/2014 | Evans et al. | |
| 9,217,812 B2 | 12/2015 | Evans et al. | |
| 9,250,356 B2 | 2/2016 | Evans et al. | |
| 2008/0226883 A1* | 9/2008 | Izumi | G02C 7/102 |
| | | | 427/164 |
| 2012/0170098 A1 | 7/2012 | Takahashi et al. | |
| 2014/0054520 A1 | 2/2014 | Takenaka et al. | |
| 2014/0154527 A1 | 6/2014 | Izumi et al. | |
| 2020/0172681 A1 | 6/2020 | Takenaka et al. | |
| 2021/0032532 A1 | 2/2021 | Miyazaki et al. | |

FOREIGN PATENT DOCUMENTS

| | | |
|---|---|---|
| JP | 2008-273848 A | 11/2008 |
| WO | WO 00/15630 A1 | 3/2000 |
| WO | WO 2004/041961 A1 | 5/2004 |
| WO | WO 2009/146509 A1 | 12/2009 |
| WO | WO 2011/034202 A1 | 3/2011 |
| WO | WO 2012/121414 A1 | 9/2012 |
| WO | WO 2012/149599 A1 | 11/2012 |
| WO | WO 2012/162725 A1 | 12/2012 |
| WO | WO 2012/176918 A1 | 12/2012 |
| WO | WO 2018/235771 A1 | 12/2018 |
| WO | WO 2019/203205 A1 | 10/2019 |

OTHER PUBLICATIONS

Extended European Search Report for corresponding European Application No. 18831038.7, dated Mar. 9, 2021.
Malic et al., "The Use of Poly(Alkylene Oxide)s to Achieve Fast and Controlled Photochromic Switching in Rigid Matrices," Journal of Polymer Science Part A: Polymer Chemistry, vol. 50, 2012, pp. 1434-1444.

* cited by examiner

CHROMENE COMPOUND, CURABLE COMPOSITION COMPRISING THE COMPOUND, AND OPTICAL ARTICLE INCLUDING A CURED BODY OF THE CURABLE COMPOSITION

TECHNICAL FIELD

The present invention relates to a novel chromene compound, a novel photochromic curable composition comprising the chromene compound, and a novel optical article including a cured body of the photochromic curable composition.

BACKGROUND ART

Photochromism is a reversible function that a certain compound changes its color swiftly upon exposure to light including ultraviolet light such as sunlight or light from a mercury lamp and returns to its original color when it is put in the dark by stopping its exposure to light. A compound having this property is called "photochromic compound", and various compounds have been developed so far. Since it is known that chromene compounds out of these photochromic compounds have high durability and develop various colors, active studies have been made on these compounds in recent years.

For example, photochromic spectacle lenses which are manufactured by providing photochromic properties to spectacle lenses function as sunglasses which are quickly colored outdoors where they are irradiated with sunlight and as ordinary spectacle lenses indoors where they are faded, and demand for the photochromic spectacle lenses is growing.

For photochromic compounds used in optical materials, the following properties are generally required.
(1) The degree of coloration at a visible light range before ultraviolet light is applied (initial coloration) should be low.
(2) The degree of coloration upon exposure to ultraviolet light (color optical density) should be high.
(3) The speed from the start of the application of ultraviolet light to the time when optical color density reaches saturation (color development sensitivity) should be high.
(4) The speed from the stoppage of the application of ultraviolet light to the time when the compound returns to its original state (fading speed) should be high.
(5) The repeated durability of this reversible function should be high.
(6) The compound should dissolve in a monomer composition which will become a host material after curing in a high concentration to ensure that its dispersibility in the host material in use becomes high.

Chromene compounds which have been found so far have excellent photochromic properties themselves and, there are known, for example, some chromene compounds having high color development and high fading speeds and high color optical density in a solution. It is known that the color change of a chromene compound is caused by its structural change. Therefore, the chromene compound has quick light response in an environment where the structural change tends to occur, for example, in a solution. However, the chromene compound tends to have slow light response and a long fading half-life, that is, reduced light response in an environment where the structural change hardly occurs, for example, in a polymer solid matrix. It is considered that the cause of this is that the structural change of the chromene compound is restricted due to a very small free space in the polymer solid matrix as compared with a space in a solution. When the chromene compound is dispersed in a polymer matrix such as a plastic material, the chromene compound cannot develop excellent photochromic properties that chromene compounds originally have with the result that the fading speed in particular becomes low. This problem tends to become notable when the chromene compound is kneaded into a synthetic resin (polymer) having high hardness or high heat resistance.

To solve this problem, photochromic compounds having various structures are now under study. For example, there are proposed photochromic compounds which can be nano-capsulated to increase the fading speed. Stated more specifically, there are disclosed photochromic compounds represented by the following formulas (A) and (B), which have a polyalkylene oxide oligomer chain group or polysiloxane oligomer chain group (refer to Patent Documents 1 and 2).

[CF 1]

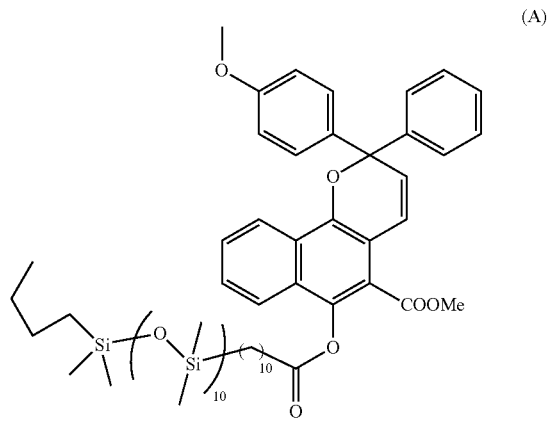

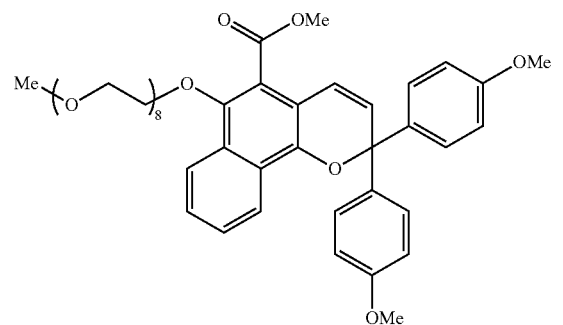

However, according to studies conducted by the inventors of the present invention, it was found that the chromene compounds represented by the above formulas (A) and (B) need to be further improved to meet recent requirements for high photochromic properties and repeated durability though they can be nano-capsulated.

Besides these chromene compounds, there are proposed photochromic compounds having at least two photochromic moieties (refer to Patent Documents 3 to 5). However, even when the compounds have a plurality of photochromic moieties to increase pigment density, these conventional photochromic compounds need to be further improved to meet recent requirements for high photochromic properties. It has been difficult to reduce matrix dependence and further increase the fading speed in particular.

PRIOR ART DOCUMENTS

Patent Documents

[Patent Document 1] WO2004/041961 pamphlet
[Patent Document 2] WO2000/015630 pamphlet
[Patent Document 3] WO2009/146509 pamphlet
[Patent Document 4] WO2012/149599 pamphlet
[Patent Document 5] WO2012/162725 pamphlet

DISCLOSURE OF THE INVENTION

Problem to be Solved by the Invention

As described above, when the synthetic resin is used as a matrix, there is room for the improvement of fading speed in the prior art.

Further, various polymers have recently been used as materials for optical articles. Then, if a photochromic compound which has low matrix dependence (matrix environmental dependence) with high color optical density and high fading speed in any polymer solid matrix as in a solution can be produced, its utility value will increase. In addition, the cost of an expensive photochromic curable composition (curable composition comprising a photochromic compound and a polymerizable compound) will be able to be reduced.

It is therefore an object of the present invention to provide a chromene compound which has low matrix environmental dependence, high fading speed and high repeated durability.

Means for Solving the Problem

The inventors of the present invention conducted intensive studies to solve the above problem. As described above, conventionally, it was considered that a photochromic compound into which an oligomer chain group has been introduced achieves high fading speed in a polymer solid matrix as it takes a form (nano-capsulation) that the oligomer chain encloses the photochromic compound in the matrix.

The inventors of the present invention considered that a photochromic compound having low matrix dependence can be obtained by utilizing this form. Although matrix dependence can be reduced by introducing the oligomer chain group, the fading speed of the photochromic compound itself cannot be increased. Therefore, when indenonaphthopyran compounds having various substituents were studied as further improvement needed to be made, they found that the above problem can be solved by an indenonaphthopyran compound having the following structure (may be referred to as "chromene compound" hereinafter). Thus, the present invention was accomplished.

That is, the first invention is a chromene compound having an indenonaphthopyran moiety, wherein the indenonaphthopyran moiety has a spiro ring formed together with the 13-position carbon atom at the 13-position and an oligomer chain group selected from the group consisting of a polyalkylene oxide oligomer chain group and a polyester oligomer chain group both of which have at least three recurring units.

The second invention is a photochromic curable composition comprising the chromene compound of the present invention and a polymerizable monomer.

The third invention is a photochromic optical article having a polymer molded body containing the chromene compound of the present invention dispersed therein as a structural member.

The fourth invention is an optical article having an optical substrate whose at least one surface is wholly or partially covered with a polymer film containing the chromene compound of the present invention dispersed therein as a structural member.

Effect of the Invention

The chromene compound of the present invention has at least one indenonaphthopyran moiety (indenonaphthopyran structure) which has a spiro ring formed together with the 13-position carbon atom at the 13-position (may be simply referred to as "13-position spiro ring group" hereinafter) and an oligomer chain group (may be simply referred to as "oligomer chain group" hereinafter) selected from the group consisting of a polyalkylene oxide oligomer chain group having at least three recurring units and a polyester oligomer chain group having at least three recurring units. Since the chromene compound has this structure, it exhibits an excellent effect. That is, due to the structural feature that the chromene compound has both the 13-position spiro ring group and the oligomer chain group, it exhibits an excellent effect. Stated more specifically, there can be obtained a chromene compound having low matrix dependence, high fading speed and high durability.

Stated more specifically, when the chromene compound has only the 13-position Spiro ring group or only the oligomer chain group, it cannot exhibit a satisfactory effect. For example, when the chromene compound has no 13-position spiro ring group but an alkyl group substituted to the 13-position and even when it has the oligomer chain group, it cannot be a compound having excellent photochromic properties, especially high fading speed. Even when the compound has the oligomer chain group substituted to the 13-position directly, its durability tends to lower.

As obvious from above, since the compound has the structure of the present invention, the compound is able to have reduced environmental dependence and even when the material of a solid matrix is changed, high fading speed in the matrix. In addition, as compared with an optical article obtained by using a conventional similar chromene compound having an oligomer chain group, high repeated durability can be provided.

A compound having both the 13-position spiro ring group and the oligomer chain group like the chromene compound of the present invention has not been existent in the prior art.

Therefore, for instance, when the chromene compound of the present invention is used in a photochromic spectacle lens and even when a spectacle lens having high hardness and a spectacle lens having relatively low hardness are produced, these spectacle lenses have high optical color density and high fading speed.

BEST MODE FOR CARRYING OUT THE INVENTION

The chromene compound of the present invention is a compound having in the molecule at least one indenonaphthopyran moiety which has a spiro ring formed together with the 13-position carbon atom at the 13-position.

The number of the indenonaphthopyran moieties is not particularly limited if there is at least one in the molecule. When the productivity, photochromic properties and compatibility with a polymer solid matrix in particular of the chromene compound itself are taken into consideration, the number of the indenonaphthopyran moieties is preferably 1 to 10, more preferably 1 to 6, much more preferably 1 to 4, particularly preferably 1.

When the chromene compound has a plurality of indenonaphthopyran moieties, the indenonaphthopyran moieties may have the same structure or different structures. At least one of the indenonaphthopyran moieties should have the 13-position spiro ring group. To develop excellent photochromic properties, all the indenonaphthopyran moieties preferably have the 13-position spiro ring group.

The indenonaphthopyran moiety of the chromene compound of the present invention has an oligomer chain group having at least three recurring units. The oligomer chain group is a group selected from the group consisting of a polyalkylene oxide oligomer chain group and a polyester oligomer chain group. In the present invention, "having at least three recurring units" means "the existence of at least three recurring units which are binding moieties having the same composition". More specifically, for example, the polyalkylene oxide oligomer chain group having at least three recurring units (formula; —(R—O)s-, R: alkylene group, s: number of recurring units) is a group in which "s" is at least three in the above formula.

When the number of the recurring units of the oligomer chain group is smaller than 3, excellent photochromic properties and compatibility with a matrix deteriorate disadvantageously. The maximum number of recurring units is not particularly limited but is suitably determined according to the number of the oligomer chain groups, the structural formula forming the oligomer chain group and the number of the indenonaphthopyran moieties. When the productivity and photochromic properties in particular of the chromene compound itself are taken into consideration, the maximum number of recurring units is preferably smaller than 200. The number of recurring units is preferably 3 to 150, more preferably 10 to 100.

The average molecular weight of the oligomer chain group is not particularly limited but preferably 300 to 20,000, more preferably 350 to 15,000, much more preferably 350 to 12,000, particularly preferably 440 to 7,500. When the average molecular weight of the above oligomer chain group is too low (oligomer chain length is short), the formation of a nano-capsule enclosing the photochromic compound may be difficult or the size of the capsule tends to become small. Therefore, a free space around the photochromic compound cannot be secured completely, whereby the effect of reducing matrix environmental dependence tends to become small. When the average molecular weight is too high, the percentage of the photochromic compound per unit weight tends to become small, color optical density becomes unsatisfactory, and the amount of the photochromic compound to be added must be increased.

In the chromene compound of the present invention, the number of the oligomer chain groups is not particularly limited but should be at least one in one molecule of the chromene compound. When the productivity and photochromic properties in particular of the chromene compound itself are taken into consideration, the number of the oligomer chain groups is preferably 1 to 10, more preferably 1 to 5. The number of the oligomer chain groups for one indenonaphthopyran moiety is preferably 0.5 to 6, more preferably 0.5 to 3, much more preferably 0.5 to 2. When productivity and efficient photochromic properties in particular are taken into consideration, the number of the oligomer chain groups is preferably 0.5 to 1. When the number of the oligomer chain groups is 0.5 for one indenonaphthopyran moiety, the indenonaphthopyran moiety is existent at both ends of the oligomer chain group. When there are a plurality of the oligomer chain groups, they may be the same or different. When the productivity of the chromene compound is taken into consideration, they are preferably the same. When photochromic properties are taken into consideration, the oligomer chain group is most preferably a polyalkylene oligomer chain group.

It is preferred that the above oligomer chain group should be substituted to the 3-position, 6-position, 7-position, 11-position or 13-position spiro ring group of the indenonaphthopyran as the effect of the present invention, i.e., the productivity of the chromene compound itself can be improved.

<Preferred Chromene Compound>

In the present invention, the indenonaphthopyran moiety preferably has a structure represented by the following formula (1).

[CF 2]

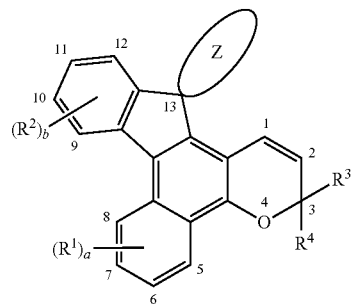

(1)

As will be described in detail hereinafter, as a matter of course, the formula Z is the 13-position spiro ring group. At least one oligomer chain group must be bonded to the indenonaphthopyran moiety represented by the above formula (1). That is, at least one of $R^2$, $R^3$ and $R^4$ should be the above oligomer chain group, or $R^1$, $R^2$, $R^3$, $R^4$ and the spiro ring group of the formula Z should have the above oligomer chain group as a substituent.

The chromene compound of the present invention preferably has at least one indenonaphthopyran moiety represented by the above formula (1) in the molecule. It is known that a chromene compound having an indenonaphthopyran skeleton generally exhibits excellent photochromic properties. A description is subsequently given of specific substituents. The preferred number and type of the indenonaphthopyran moieties represented by the formula (1) and the preferred number and type of the above oligomer chain groups are the same as those described above.

Preferably, <$R^1$ and $R^2$> are each independently an oligomer chain group having at least three recurring units (oligomer chain group selected from a polyalkylene oxide oligomer chain group having at least three recurring units, a polyester oligomer chain group having at least three recurring units and a polyester polyether oligomer chain group having at least three recurring units), hydroxyl group, alkyl group, haloalkyl group, cycloalkyl group which may have a substituent, alkoxy group, amino group, substituted amino group, heterocyclic group which may have a substituent, cyano group, halogen atom, alkylthio group, arylthio group which may have a substituent, nitro group, formyl group, hydroxycarbonyl group, alkylcarbonyl group, alkoxycarbonyl group, aralkyl group which may have a substituent, aralkoxy group which may have a substituent, aryloxy group which may have a substituent, aryl group which may have a substituent, heteroaryl group which may have a substituent, thiol group, alkoxyalkylthio group, haloalkylthio group or cycloalkylthio group which may have a substituent.

In the above formula (1), "a" indicates the number of s "b" indicates the number of $R^2$'s. "a" is an integer of 0 to 4, and "b" is an integer of 0 to 4.

When "a" is 2 to 4, a plurality of $R^1$'s may be the same or different, and when "b" is 2 to 4, a plurality of $R^2$'s may be the same or different.

When "a" is 2 to 4 and adjacent $R^1$'s are existent, two adjacent $R^1$'s may form together with two carbon atoms bonded to these $R^1$'s a ring which may include an oxygen atom, carbon atom, sulfur atom or nitrogen atom, and further the ring may have a substituent.

When "b" is 2 to 4 and adjacent $R^2$'s are existent, two adjacent $R^2$'s may form together with two carbon atoms bonded to these $R^2$'s a ring which may include an oxygen atom, carbon atom, sulfur atom or nitrogen atom, and further the ring may have a substituent.

Preferably, <$R^3$ and R> are each independently an aryl group which may have a substituent or heteroaryl group which may have a substituent.

In $R^1$, $R^2$, $R^2$ and $R^4$, the substituent of each of the groups which may have a substituent may be at least one oligomer chain group in the molecule.

A detailed description is subsequently given of $R^1$, $R^2$, $R^3$ and $R^4$. A first description is given of the oligomer chain group which may be $R^1$ and $R^2$ and a group other than the oligomer chain group.

<$R^1$ and $R^2$; Oligomer Chain Group>

The chromene compound of the present invention should be such that the indenonaphthopyran moiety represented by the above formula (1) has at least the above oligomer chain group(s) and at least one of $R^1$ and $R^2$ may become the oligomer chain group.

The above oligomer chain group is not particularly limited if it has at least three recurring units. The oligomer chain group is preferably a group having a polyalkylene oxide oligomer chain with at least three recurring units. As described above, the number of recurring units is preferably 3 to 200, more preferably 3 to 150. The average molecular weight of the oligomer chain group is preferably 300 to 20,000, more preferably 350 to 15,000, much more preferably 350 to 12,000, particularly preferably 440 to 7,500.

Out of the above oligomer chain groups, groups represented by the following formulas (5a) to (5c) are particularly preferred to achieve excellent photochromic properties and reduce matrix dependence. A chromene compound which always has one of these groups and the 13-position spiro ring group exhibits a particularly excellent effect.

<$R^1$ and $R^2$; Preferred Oligomer Chain Group>

The oligomer chain group which is particularly preferred in the present invention is preferably selected from groups represented by the following formulas (5a) to (5c):

[CF 3]

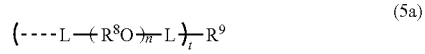
(5a)

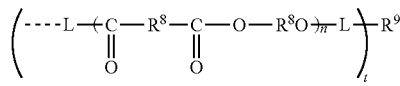
(5b)

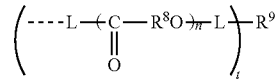
(5c)

(In the above formulas, $R^8$ is a liner or branched alkylene group having 1 to 20 carbon atoms, when a plurality of $R^8$'s are contained in the same molecule, $R^8$'s may be the same or different, "n" indicates the number of the recurring units of the above oligomer chain group and is an integer of 3 to 200, the divalent groups of the recurring units may be the same or different, L is a divalent bond group represented by the following formula (6):

[CF 4]

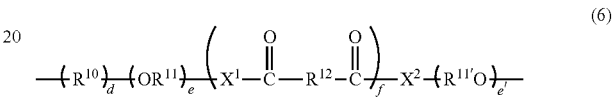
(6)

(In the above formula, is a divalent group such as linear or branched alkylene group having 1 to 20 carbon atoms, cycloalkyl group which may have a substituent with 3 to 12 carbon atoms forming a ring, aryl group which may have a substituent with 6 to 12 carbon atoms forming a ring or heterocyclic group which may have a substituent with 3 to 12 atoms forming a ring, $R^{11}$ and $R^{11'}$ are each independently a divalent group such as linear or branched alkylene group having 1 to 20 carbon atoms, cycloalkyl group which may have a substituent with 3 to 12 carbon atoms forming a ring or aryl group which may have a substituent with 6 to 12 carbon atoms forming a ring, $R^{12}$ is a divalent group such as linear or branched alkylene group having 1 to 20 carbon atoms, cycloalkyl group which may have a substituent with 3 to 12 carbon atoms forming a ring or aryl group which may have a substituent with 6 to 12 carbon atoms forming a ring, $X^1$ and $X^2$ are each independently a divalent group such as single bond, 0, S, amino group, substituted amino group, (thio)amide group or (thio) ester group, "d" is an integer of 0 to 50, "e" and "e'" are each independently an integer of 0 to 50, "f" is an integer of 0 to 50, when "d" is 2 or more, a plurality of $R^{10}$'s may be the same or different, and when "e" and "e'" are each independently 2 or more, an "e" number of divalent groups and an "e'" number of divalent groups may be the same or different, and when "f" is 2 or more, an "f" number of divalent groups may be the same or different)
a plurality of L's may be the same or different, the broken line represents a bond to the above indenonaphthopyran moiety, "t" indicates the number of the oligomer chain groups and is an integer of 1 to 10, when "t" is 1, $R^9$ is a hydrogen atom or alkyl group having 1 to 20 carbon atoms, when "t" is 2, $R^9$ is a bond or divalent organic residue, and when "t" is 3 to 10, $R^9$ is a "t" number of organic residues.}

The oligomer chain group represented by the above formula (5a) is a preferred polyalkylene oxide oligomer chain group. The oligomer chain group represented by the above formula (5b) and the oligomer chain group represented by the above formula (5c) are preferred polyester oligomer chain groups.

As for particularly preferred examples, $R^8$ is preferably an ethylene group, propylene group or butylene group, particularly preferably a propylene group.

"n" indicates the number of the recurring units of the oligomer chain group and is an integer of 3 to 200. When the productivity and photochromic properties of the chromene compound itself are taken into consideration, "n" is preferably 3 to 150, particularly preferably 10 to 100.

Particularly preferred examples of L are divalent groups represented by the following formulas.

[CF 5]

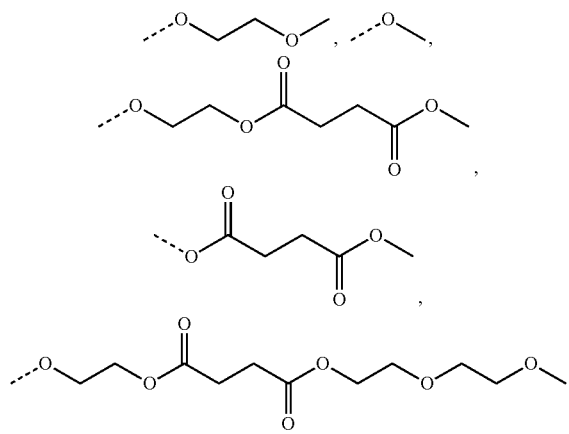

In the above preferred divalent groups represented by L and the above formulas (5a) to (5c), the broken lines indicate bonding to the above indenonaphthopyran moiety.

In the oligomer chain groups represented by the above formulas (5a) to (5c), "t" is equal to the number of oligomer chain groups.

When "t" is 1, that is, the number of oligomer chain groups is 1, the alkyl group having 1 to 20 carbon atoms represented by $R^9$ is preferably a methyl group, ethyl group, propyl group, butyl group, pentyl group or hexyl group.

When "t" is 2, $R^9$ may be a bond. That is, when $R^9$ is a bond, the substantial length of the oligomer chain is doubled and the indenonaphthopyran moiety is existent at both ends of the oligomer chain.

When "t" is 3 to 10, $R^9$ becomes a "t" number of organic residues. "t" is preferably 3 to 6. Preferred examples of the organic residue ($R^9$) are polyvalent organic residues represented by the following formulas.

[CF 6]

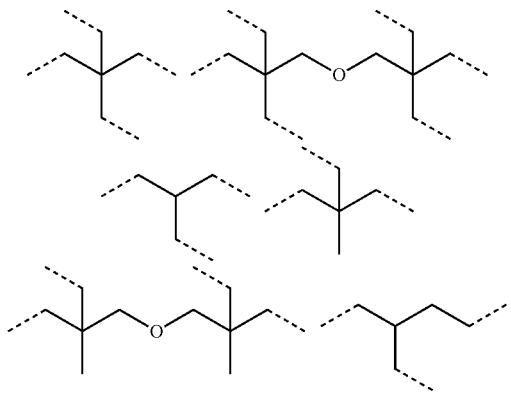

-continued

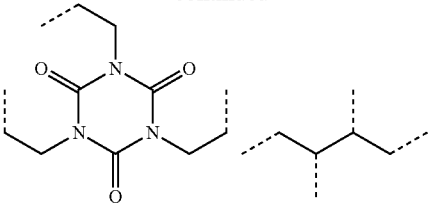

In the polyvalent organic residues, the broken lines indicate bonding to L.

The above oligomer chain groups are preferred oligomer chain groups represented by $R^1$ and $R^2$.

<$R^1$ and $R^2$; Other Groups>

In the chromene compound of the present invention, the indenonaphthopyran moiety represented by the above formula (1) should have at least one oligomer chain group and other $R^1$ and $R^2$ may be groups other than the oligomer chain group as described above.

The above alkyl group which may be represented by $R^1$ and $R^2$ is not particularly limited but preferably an alkyl group having 1 to 6 carbon atoms. Preferred examples of the alkyl group having 1 to 6 carbon atoms include methyl group, ethyl group, n-propyl group, isopropyl group, n-butyl group, sec-butyl group, tert-butyl group, pentyl group and hexyl group.

The above haloalkyl group is not particularly limited but preferably a haloalkyl group having 1 to 6 carbon atoms. The haloalkyl group having 1 to 6 carbon atoms is preferably an alkyl group substituted by a fluorine atom, chlorine atom or bromine atom. Preferred examples of the haloalkyl group include trifluoromethyl group, tetrafluoroethyl group, chloromethyl group, 2-chloroethyl group and bromomethyl group.

The above cycloalkyl group is not particularly limited but preferably a cycloalkyl group having 3 to 8 carbon atoms (cycloalkyl group having 3 to 8 carbon atoms forming a ring). Examples of the cycloalkyl group having 3 to 8 carbon atoms include cyclopropyl group, cyclobutyl group, cyclopentyl group and cyclohexyl group. Although the above cycloalkyl group may have a substituent, the above number of carbon atoms (3 to 8 carbon atoms) does not include the number of the carbon atoms of the substituent.

The above alkoxy group is not particularly limited but preferably an alkoxy group having 1 to 6 carbon atoms. Preferred examples of the alkoxy group having 1 to 6 carbon atoms include methoxy group, ethoxy group, n-propoxy group, isopropoxy group, n-butoxy group, sec-butoxy group and tert-butoxy group.

The above amino group is a primary amino group (—$NH_2$), and the substituted amino group is a secondary or tertiary amino group whose one or two hydrogen atoms are substituted. Although the substituent of the substituted amino group is not particularly limited, examples thereof include the above oligomer chain group, alkyl group having 1 to 6 carbon atoms, haloalkyl group having 1 to 6 carbon atoms, alkoxy group having 1 to 6 carbon atoms, cycloalkyl group having 3 to 7 carbon atoms, aryl group having 6 to 14 carbon atoms and heteroaryl group having 4 to 14 carbon atoms. Preferred examples of the amino group include amino group, methylamino group, dimethylamino group, ethylamino group, diethylamino group, phenylamino group and diphenylamino group.

The above heterocyclic group is preferably a heterocyclic group having 3 to 10 atoms. Examples of the group include aliphatic heterocyclic groups such as morpholino group, piperidino group, pyrrolidinyl group, piperazino group and N-methylpiperazino group, and aromatic heterocyclic groups such as indolinyl group. Further, the heterocyclic group may have a substituent. The substituent is preferably the above oligomer chain group or alkyl group having 1 to 6 carbon atoms. Preferred examples of the heterocyclic group having a substituent include 2,6-dimethylmorpholino group, 2,6-dimethylpiperidino group and 2,2,6,6-tetramethylpiperidino group.

Examples of the above halogen atom include fluorine atom, chlorine atom, bromine atom and iodine atom.

The above alkylthio group is not particularly limited but preferably an alkylthio group having 1 to 6 carbon atoms. Examples of the alkylthio group having 1 to 6 carbon atoms include methylthio group, ethylthio group, n-propylthio group, isopropylthio group, n-butylthio group, sec-butylthio group and t-butylthio group.

The above arylthio group is not particularly limited but preferably an arylthio group having 6 to 10 carbon atoms. Examples of the arylthio group having 6 to 10 carbon atoms include phenylthiol group, 1-naphtylthio group and 2-naphthylthio group.

The above alkylcarbonyl group is not particularly limited but preferably an alkylcabonyl group having 2 to 7 carbon atoms. Examples of the alkylcarbonyl group having 2 to 7 carbon atoms include acetyl group and ethylcarbonyl group.

The above alkoxycarbonyl group is not particularly limited but preferably an alkoxycarbonyl group having 2 to 7 carbon atoms. Examples of the alkoxycarbonyl group having 2 to 7 carbon atoms include methoxycarbonyl group and ethoxycarbonyl group.

The above aralkyl group is not particularly limited but preferably an aralkyl group having 7 to 11 carbon atoms. Examples of the aralkyl group having 7 to 11 carbon atoms include benzyl group, phenylethyl group, phenylpropyl group, phenylbutyl group and naphthylmethyl group.

The above aralkoxy group is not particularly limited but preferably an aralkoxy group having 7 to 11 carbon atoms. Examples of the aralkoxy group having 7 to 11 carbon atoms include benzyloxy group and naphthylmethoxy group.

The above aryloxy group is not particularly limited but preferably an aryloxy group having 6 to 12 carbon atoms. Examples of the aryloxy group having 6 to 12 carbon atoms include phenyloxy group and naphthyloxy group.

The above aryl group is not particularly limited but preferably an aryl group having 6 to 12 carbon atoms. Examples of the aryl group having 6 to 12 carbon atoms include phenyl group, 1-naphthyl group and 2-naphthyl group.

The above heteroaryl group is not particularly limited but preferably a heteroaryl group having 3 to 12 carbon atoms. Examples of the heteroaryl group having 3 to 12 carbon atoms include thienyl group, furyl group, pyrrolinyl group, pyridyl group, benzothienyl group, benzofuranyl group and benzopyrrolinyl group.

The above alkoxyalkylthio group is not particularly limited but preferably an alkoxyalkylthio group having 2 to 9 carbon atoms. Examples of the alkoxyalkylthio group having 2 to 9 carbon atoms include methoxymethylthio group, methoxyethylthio group, methoxy-n-propylthio group, methoxy-n-butylthio group, ethoxyethylthio group and n-propoxypropylthio group.

The above haloalkylthio group is not particularly limited but preferably a haloalkylthio group having 1 to 6 carbon atoms. Examples of the haloalkylthio group having 1 to 6 carbon atoms include trifluoromethylthio group, tetrafluoroethylthio group, chloromethylthio group, 2-chloroethylthio group and bromomethylthio group.

The above cycloalkylthio group is not particularly limited but preferably a cycloalkylthio group having 3 to 8 carbon atoms. Examples of the cycloalkylthio group having 3 to 8 carbon atoms include cyclopropylthio group, cyclobutylthio group, cyclopentylthio group and cyclohexylthio group. Although the above cycloalkylthio group may have a substituent, the above number of carbon atoms (3 to 8 carbon atoms) does not include the number of the carbon atoms of the substituent.

The above cycloalkyl group, the above arylthio group, the above aralkyl group, the above aralkoxy group, the above aryloxy group, the above aryl group, the above heteroaryl group and the above cycloalkylthio group may be non-substituted. When they have a substituent, 1 to 8 hydrogen atoms, particularly preferably 1 to 4 hydrogen atoms of the group forming a ring are preferably substituted by a substituent selected from the above oligomer chain group, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group having 3 to 8 carbon atoms, cyano group, nitro group and halogen atom. Examples of these substituents are the same as those listed above.

The number of the carbon atoms of each of the above aralkyl group, the above aralkoxy group, the above aryloxy group, the above aryl group and the above heteroaryl group does not include the number of the carbon atoms of the substituent.

<"a" and "b">

In the above formula (1), "a" indicates the number of $R^1$'s. "b" indicates the number of $R^2$'s. "a" is an integer of 0 to 4, and "b" is an integer of 0 to 4. When "a" is 2 to 4, a plurality of $R^1$'s may be the same or different, and when "b" is 2 to 4, a plurality of R's may be the same or different.

<When "a" and "b" are 2 or More>

When "a" is 2 to 4 and there are adjacent $R^1$'s, two adjacent $R^1$'s may form together with two carbon atoms bonded to these s a ring which may include an oxygen atom, sulfur atom, carbon atom or nitrogen atom, and further the ring may have a substituent. The ring may have at least two atoms among oxygen atoms, sulfur atoms, carbon atoms or nitrogen atoms at the same time.

Examples of a combination of adjacent $R^1$'s are $R^1$'s at the 5-position and the 6-position, $R^1$'s at the 6-position and 7-position and $R^1$'s at the 7-position and 8-position of the chromene compound.

When "b" is 2 to 4 and there are adjacent $R^2$'s, two adjacent $R^2$'s may form together with two carbon atoms bonded to these $R^2$'s a ring which may include an oxygen atom, sulfur atom, carbon atom or nitrogen atom, and further the ring may have a substituent. The ring may have at least two atoms among oxygen atoms, sulfur atoms, carbon atoms or nitrogen atoms at the same time.

Examples of a combination of adjacent $R^2$'s are $R^2$'s at the 9-position and the 10-position, $R^2$'s at the 10-position and the 11-position and $R^2$'s at the 11-position and the 12-position of the chromene compound.

Two adjacent s and two adjacent $R^2$'s may independently form together a ring group which may include an oxygen atom, sulfur atom, carbon atom or nitrogen atom. Although the ring groups are not particularly limited, they are preferably rings having 5 to 7 atoms including carbon atoms bonded to $R^1$ and $R^2$, respectively. Although each of the rings may have a substituent, the substituent is selected from the above oligomer chain group, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group having 3 to 8 atoms, cyano group, nitro group and halogen atom. Examples of the substituent are the same as those listed above. The substituent is preferably selected to obtain a ring represented by a formula (3) which will be described hereinafter.

<Particularly Preferred $R^1$ and $R^2$>

In the above groups, when the developed color tone and color optical density of the obtained photochromic compound are taken into consideration, $R^1$ and $R^2$ are each preferably the above oligomer chain group, the above alkyl group, the above alkoxy group, the above heterocyclic group, the above aryl group or the above arylthio group. Preferably, adjacent $R^1$'s or adjacent $R^2$'s are bonded together to form a ring. The substituent of each of the above groups which may have a substituent may be the above oligomer chain group.

<$R^3$ and $R^4$>

$R^3$ and $R^4$ are each independently an aryl group which may have a substituent or heteroaryl group which may have a substituent.

Examples of the aryl group or the heteroaryl group include those listed for the above <$R^1$ and $R^2$>, out of which phenyl group is most preferred.

The aryl group or the heteroaryl group may have a substituent. These substituents are each independently selected from oligomer chain group, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, heterocyclic group, cyano group, halogen atom, alkylthio group having 1 to 6 carbon atoms, arylthio group having 6 to 10 carbon atoms which may have a substituent, hydroxyl group, alkyl group, haloalkyl group, cycloalkyl group, alkoxy group, amino group, substituted amino group, heterocyclic group which may have a substituent, cyano group, nitro group and halogen atom. Examples of these substituents include groups listed for the above <$R^1$ and $R^2$>.

The substituents of the above aryl group and the above heteroaryl group are each preferably selected from the above oligomer chain group, the above alkyl group, the above alkoxy group, the above amino group, the above substituted amino group, the above heterocyclic group, the above halogen atom and the above arylthio group as excellent photochromic properties are obtained.

<Ring Z (Group)>

The spiro ring Z (13-position spiro ring group) represented by the following formula (Z)

[CF 7]

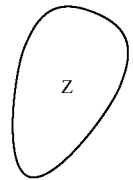

and bonded to the 13-position of the chromene compound together with the 13-position carbon atom is an aliphatic ring which may have a substituent and has 3 to 20 carbon atoms constituting the ring together with the 13-position carbon atom, condensed polycyclic ring obtained by condensing an aromatic ring or aromatic heterocyclic ring which may have a substituent to the aliphatic ring, heterocyclic ring which may have a substituent and has 3 to 20 atoms constituting the ring together with the 13-position carbon atom, or condensed polycyclic ring obtained by condensing an aromatic ring or aromatic heterocyclic ring which may have a substituent to the heterocyclic ring. As a matter of course, the number of carbon atoms or atoms specified for the above ring group is the number of carbon atoms or atoms constituting the ring and does not include the number of carbon atoms or atoms of a substituent.

Examples of the above aliphatic ring include cyclopentane ring, cyclohexane ring, cyclooctane ring, cycloheptane ring, norbornane ring, bicyclononane ring, adamantane ring and spirodicyclohexane ring.

Examples of the condensed polycyclic ring obtained by condensing an aromatic ring or aromatic heterocyclic ring to the aliphatic ring include phenanthrene ring.

Examples of the heterocyclic ring include thiophene ring, furan ring and pyridine ring.

Examples of the condensed polycyclic ring obtained by condensing an aromatic ring or aromatic heterocyclic ring to the heterocyclic ring include phenylfuran ring and biphenylthiophene ring.

The above aliphatic ring, the above condensed polycyclic ring obtained by condensing an aromatic ring or aromatic heterocyclic ring to the aliphatic ring, the above heterocyclic ring or the above condensed polycyclic ring obtained by condensing an aromatic ring or aromatic heterocyclic ring to the heterocyclic ring may have a substituent. The substituent substituted to the ring (condensed polycyclic ring) is selected from the above oligomer chain group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group and halogen atom. These substituents are the same as those listed for <$R^1$ and $R^2$>. Out of the substituents of the spiro ring Z, alkyl group having 1 to 6 carbon atoms, cycloalkyl group, haloalkyl group having 1 to 6 carbon atoms and alkoxy group having 1 to 6 carbon atoms are particularly preferred as the chromene compound of the present invention exhibits a particularly excellent effect.

Out of the above Spiro rings Z, the above aliphatic hydrocarbon ring groups having 6 to 16 carbon atoms constituting a spiro ring, ring groups having an alkyl group having 1 to 6 carbon atoms (preferably alkyl group having 1 to 3 carbon atoms) substituted to the aliphatic hydrocarbon rings, or ring groups obtained by bonding or condensing a cycloalkyl group having 3 to 8 carbon atoms to the aliphatic hydrocarbon rings are preferred to obtain high fading speed.

Out of these, the following ring is preferred from the viewpoints of obtaining excellent fading speed and high color optical density. That is, preferably, the spiro ring Z is a ring selected from cyclopentane ring, cyclohexane ring, cycloheptane ring, cyclooctane ring, cyclononane ring, cyclodecane ring, cycloundecane ring, cyclododecane ring and spirodicyclohexane ring, the ring may have 1 to 10 alkyl groups with 1 to 3 carbon atoms or 1 to 10 cycloalkyl groups with 5 to 7 carbon atoms as substituents, or the ring is a ring to which a cycloalkyl group having 5 to 7 carbon atoms may be condensed.

Particularly preferred examples of the Spiro ring Z are represented by the following formulas.

[CF 8]

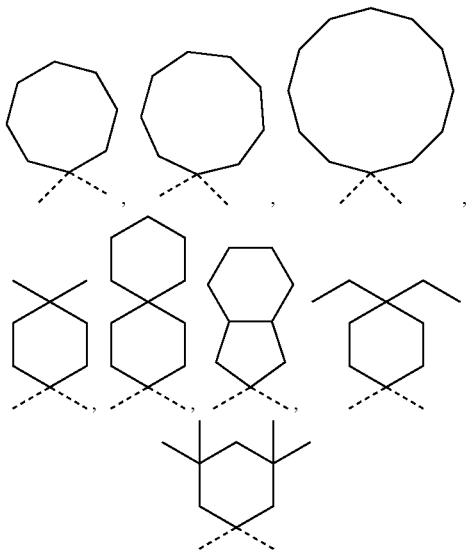

In the above formulas, the carbon atom having a bond shown by a dotted line is the 13-position carbon atom.

<Preferred Substitution Position of Oligomer Chain Group>

The chromene compound of the present invention must have at least one oligomer chain group in the molecule. Therefore, in the groups represented by $R^1$, $R^2$, $R^3$ and $R^4$, the substituent of each of the groups which may have a substituent may be the above oligomer chain group. Preferably, the above oligomer chain group is substituted to the 3-position ($R^3$ and $R^4$), 6-position ($R^1$), 7-position ($R^1$), 11-position ($R^2$) or 13-position spiro ring group (formula Z) of the indenonaphthopyran as the effect of the present invention, i.e., the productivity of the chromene compound itself can be improved. The above oligomer chain group may be directly bonded to the 3-position, the 6-position, the 7-position or the 11-position or may be introduced as the substituent of a group bonded to any one of these positions.

<Particularly Preferred Chromene Compound>

In the present invention, the preferred chromene compound is a chromene compound represented by the following formula (2). This chromene compound must have at least one oligomer chain group in the molecule.

[CF 9]

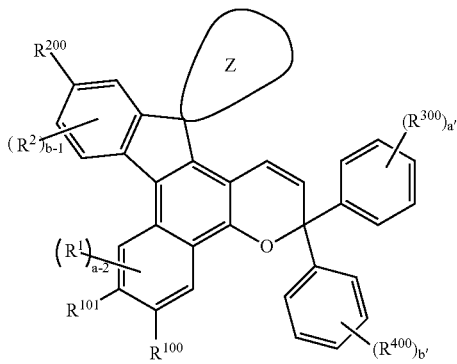

In the above formula, $R^1$, $R^2$, "a", "b" and the ring Z are as defined in the above formula (1). "a-2" is a number obtained by subtracting 2 from the integer "a" and is an integer of 0 to 2. "b-1" is a number obtained by subtracting 1 from the integer "b" and is an integer of 0 to 3.

<$R^{100}$ and $R^{101}$>

$R^{100}$ and $R^{101}$ are preferably the following groups out of the groups listed for the above <$R^1$ and $R^2$>. Stated more specifically, they are each the oligomer chain group, hydrogen atom, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group which may have a substituent, cyano group, halogen atom, alkylthio group having 1 to 6 carbon atoms, arylthio group having 6 to 10 carbon atoms which may have a substituent, nitro group, formyl group, hydroxycarbonyl group, alkylcarbonyl group having 2 to 7 carbon atoms, alkoxycarbonyl group having 2 to 7 carbon atoms, aralkyl group having 7 to 11 carbon atoms which may have a substituent, aralkoxy group having 7 to 11 carbon atoms which may have a substituent, aryloxy group having 6 to 12 carbon atoms which may have a substituent, aryl group having 6 to 12 carbon atoms which may have a substituent, heteroaryl group having 3 to 12 carbon atoms which may have a substituent, thiol group, alkoxyalkylthio group having 2 to 9 carbon atoms, haloalkylthio group having 1 to 6 carbon atoms or cycloalkylthio group having 3 to 8 carbon atoms. These groups are the same as those listed for the above <$R^1$ and $R^2$>.

$R^{100}$ and $R^{101}$ may form a ring represented by the following formula (3) together.

[CF 10]

(3)

In the above formula, two asterisk marks represent bonds to the 6-position carbon atom and 7-position carbon atom, respectively.

<X and Y>

In the above formula, either one or both of X and Y are sulfur atoms, methylene groups, oxygen atoms or groups represented by the following formula (4).

[CF 11]

(4)

In the above formula, $R^7$ is the above oligomer chain group, hydrogen atom, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, aryl group having 6 to 12 carbon atoms which may have a substituent or heteroaryl group having 3 to 12 carbon atoms which may have a substituent. Examples of these groups are the same as those listed for the above <$R^1$ and $R^2$>, and preferred groups are the same as those listed for the above <$R^1$ and $R^2$>.

<$R^5$ and $R^6$>

Preferably, $R^5$ and $R^6$ are each independently the above oligomer chain group, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group which may have a substituent, cyano group, nitro group, formyl group, hydroxycarbonyl group, alkylcarbonyl group having 2 to 7 carbon atoms, alkoxycarbonyl group having 2 to 7 carbon atoms, halogen atom, aralkyl group having 7 to 11 carbon atoms which may have a substituent, aralkoxy group having 7 to 11 carbon atoms which may have a substituent, aryl group having 6 to 12 carbon atoms which may have a substituent, thiol group, alkylthio group having 1 to 6 carbon atoms, alkoxyalkylthio group having 2 to 9 carbon atoms, haloalkylthio group having 1 to 6 carbon atoms, cycloalkylthio group having 3 to 8 carbon atoms or arylthio group having 6 to 10 carbon atoms which may have a substituent. Examples of these groups are the same as those listed for the above <$R^1$ and $R^2$>, and preferred groups are the same as those listed for the above <$R^1$ and $R^2$>.

$R^5$ and $R^6$ may form an aliphatic ring which may have a substituent together with carbon atoms bonded thereto. Examples of the aliphatic ring include cyclopentane ring and cyclohexane ring. Although the substituent of the aliphatic ring is not particularly limited, 1 to 8 hydrogen atoms, particularly preferably 1 to 4 hydrogen atoms of the group forming the ring may be substituted by a substituent selected from the above oligomer chain group, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group having 3 to 8 atoms, cyano group, nitro group and halogen atom. Examples of these substituents are the same as those listed for the above <$R^1$ and $R^2$>.

In the above formula, "c" is an integer of 1 to 3.

<Particularly Preferred $R^{100}$ and $R^{101}$>

When the developed color tone and color optical density of the obtained photochromic compound are taken into consideration, $R^{100}$ and $R^{101}$ are each preferably the above oligomer chain group, hydrogen atom, the above alkyl group, the above alkoxy group, the above heterocyclic group, the above aryl group or the above arylthio group out of the above groups. They may form a ring represented by the above formula (3) together. The substituent of each of the above groups which may have a substituent may be the oligomer chain group.

<$R^{200}$>

$R^{200}$ is preferably the following group out of the groups listed for the above <$R^1$ and $R^2$>. Stated more specifically, it is the above oligomer chain group, hydrogen atom, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group which may have a substituent, cyano group, nitro group, formyl group, hydroxycarbonyl group, alkylcarbonyl group having 2 to 7 carbon atoms, alkoxycarbonyl group having 2 to 7 carbon atoms, halogen atom, aralkyl group having 7 to 11 carbon atoms which may have a substituent, aralkoxy group having 7 to 11 carbon atoms which may have a substituent, aryl group having 6 to 12 carbon atoms which may have a substituent, thiol group, alkylthio group having 1 to 6 carbon atoms, alkoxyalkylthio group having 2 to 9 carbon atoms, haloalkylthio group having 1 to 6 carbon atoms, cycloalkylthio group having 3 to 8 carbon atoms or arylthio group having 6 to 10 carbon atoms which may have a substituent. Examples of these groups are the same as those listed for the above <$R^1$ and $R^2$>, and preferred groups are the same as those listed for the above <$R^1$ and $R^2$>.

<Particularly Preferred $R^{200}$>

When the developed color tone and color optical density of the obtained photochromic compound are taken into consideration, $R^{200}$ is preferably the above oligomer chain group, hydrogen atom, the above alkoxy group, the above heterocyclic group or the above aryl group out of the above groups. The substituent of each of the above groups which may have a substituent may be the above oligomer chain group.

<$R^{300}$ and $R^{400}$>

Preferably, $R^{300}$ and $R^{400}$ are each independently the above oligomer chain group, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group, cyano group, halogen atom, alkylthio group having 1 to 6 carbon atoms or arylthio group having 6 to 10 carbon atoms which may have a substituent. Examples of these groups are the same as those listed for the above <$R^1$ and $R^2$>, and preferred groups are the same as those listed for the above <$R^1$ and $R^2$>.

"a'" indicates the number of $R^{300}$'s and is an integer of 0 to 5. When "a'" is 2 or more, $R^{300}$'s may be the same or different.

"b'" indicates the number of $R^{400}$'s and is an integer of 0 to 5. When "b'" is 2 or more, $R^{400}$'s may be the same or different.

<Particularly Preferred $R^{300}$ and $R^{400}$>

When the developed color tone and color optical density of the obtained photochromic compound are taken into consideration, $R^{300}$ and $R^{400}$ are each preferably the above oligomer chain group, the above alkyl group, the above alkoxy group, the above substituted amino group or the heterocyclic group out of the above groups. The substituent of the above group which may have a substituent may be the above oligomer chain group.

<Preferred Substitution Position of Preferred Oligomer Chain Group>

The above oligomer chain group is preferably existent at the 3-position ($R^{300}$ or $R^{400}$), the 6-position ($R^{100}$), the 7-position ($R^{101}$), the 11-position ($R^{200}$) or the 13-position (ring (Z)) of the indenonaphthopyran since the effect of the present invention, i.e., the productivity of the chromene compound itself can be improved. When the above oligomer chain group is existent at the 3-position ($R^{300}$ or $R^{400}$), $R^{300}$ or $R^{400}$ is preferably a phenyl group having the above oligomer chain group at the para-position.

<Preferred Examples of Chromene Compound>

In the present invention, particularly preferred examples of the chromene compound are represented by the following formulas.

As a matter of course, in the following formulas, "n" indicates the number of the recurring units of the oligomer chain group and is an integer of 3 to 200. When the productivity and photochromic properties of the chromene compound itself are taken into consideration, "n" is preferably 3 to 150, particularly preferably 10 to 100.

[CF 12]
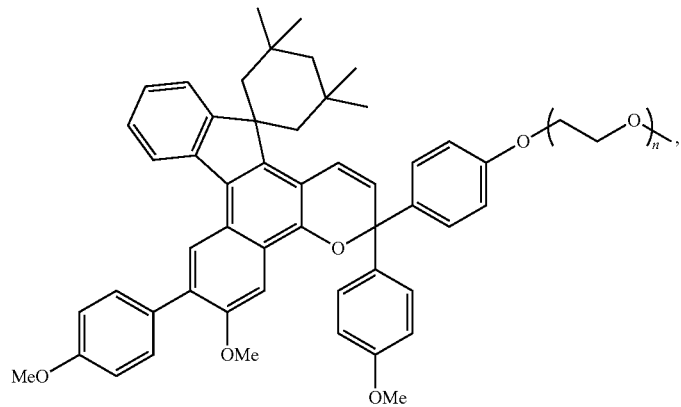
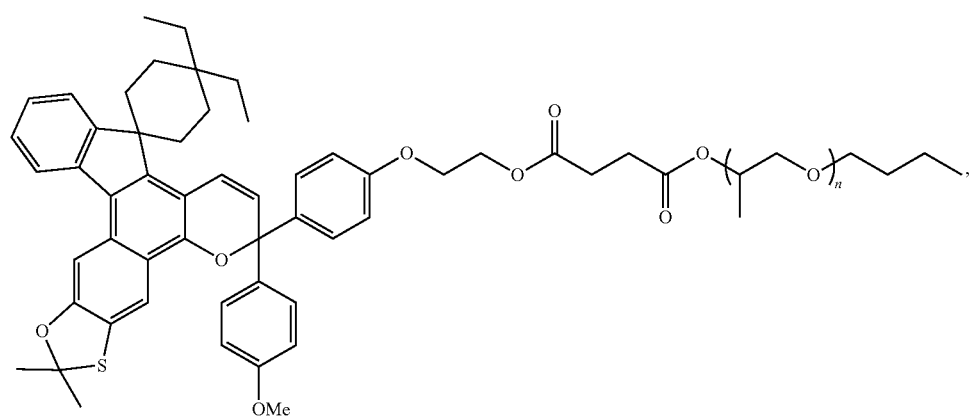
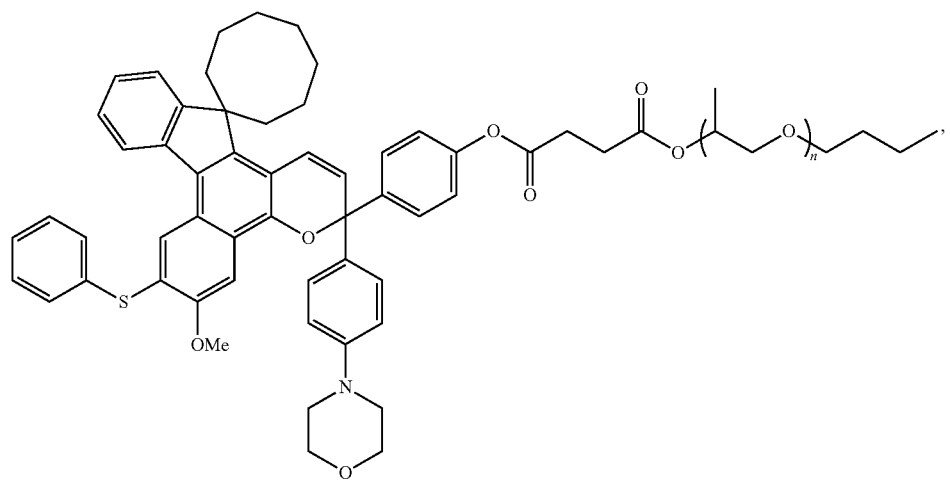

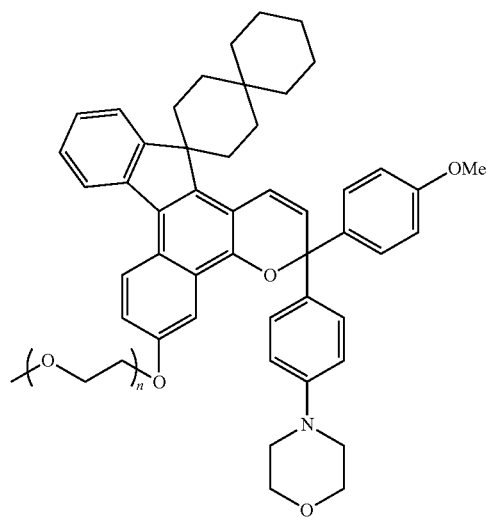
[CF 13]
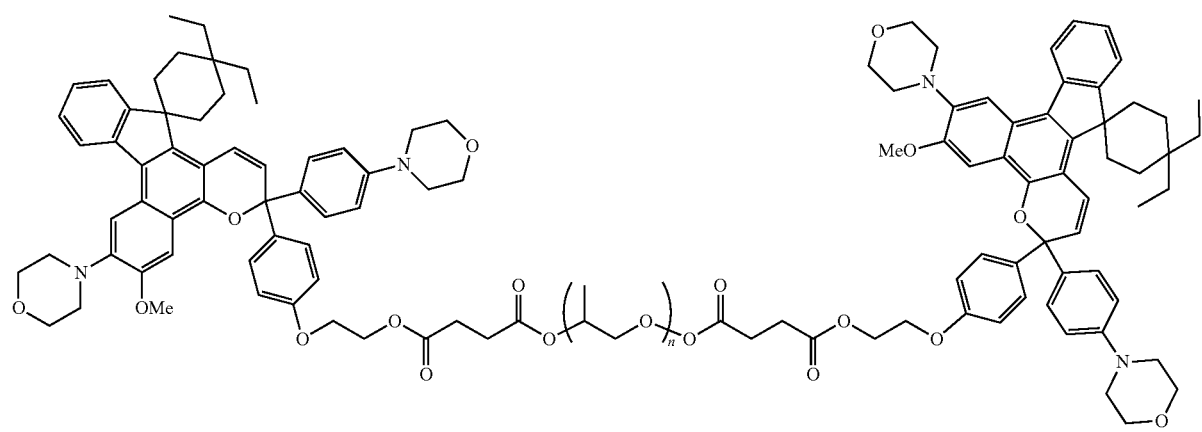
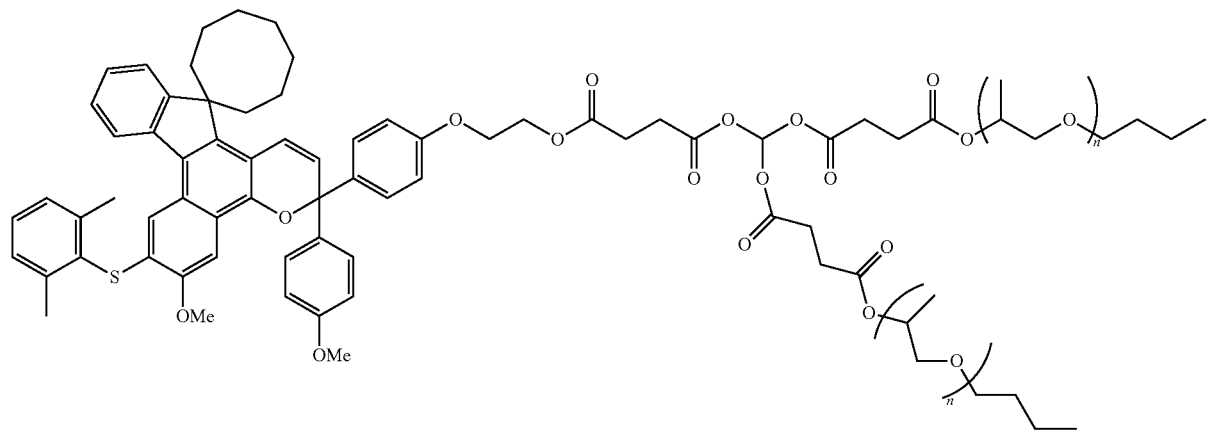

<Production Method of Chromene Compound>

The chromene compound of the present invention may be produced by any synthesizing method. A typical example of the production method of the chromene compound will be described but the present invention is not limited to this method. In the following description, reference symbols in the formulas are as defined in the above formulas unless otherwise noted.

The production of the chromene compound can be preferably carried out by reacting a naphthol compound represented by the following formula (7)

[CF 14]

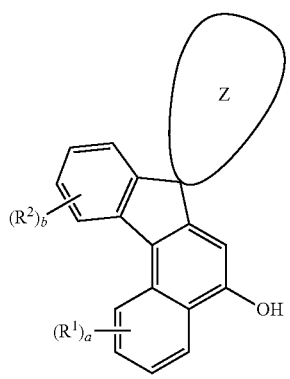

(7)

(In the above formula, $R^1$, $R^2$, "a" and "b" are as defined in the above formula (1))
and a propargyl alcohol compound represented by the following formula (8)

[CF 15]

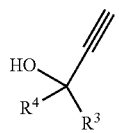

(8)

(In the above formula, $R^3$ and $R^4$ are as defined in the above formula (1))
in the presence of an acid catalyst. The reaction ratio of the naphthol compound and the propargyl alcohol compound is preferably selected from a range of 1:10 to 10:1 (molar ratio). As the acid catalyst, sulfuric acid, benzene sulfonic acid, p-toluenesulfonic acid or acidic alumina is used. The acid catalyst is preferably used in an amount of 0.1 to 10 parts by weight based on 100 parts by weight of the total of the naphthol compound and the propargyl alcohol compound. The reaction temperature is preferably 0 to 200° C. As the solvent, an aprotic organic solvent such as N-methylpyrrolidone, dimethyl formamide, tetrahydrofuran, benzene or toluene is preferably used. The method of purifying a product obtained by the above reaction is not limited. For example, the product can be purified by carrying out silica gel column purification and further recrystallization.

Stated more specifically, a production example of a chromene compound into which a polyalkylene oxide oligomer chain group (for example, oligomer chain group represented by the above formula (5a)) has been introduced is described below. That is, a method in which a polyalkylene oxide oligomer chain group is substituted to the naphthol compound represented by the above formula (7) is described below.

A polyalkylene glycol monoalkyl ether represented by the following formula (9)

[CF 16]

(9)

(In the above formula, $R^8$, $R^9$ and "n" are as defined in the formula (5a).)
is converted into a substituent having high releasability such as tosyl group or halogen atom and represented by the following formula (10).

[CF 17]

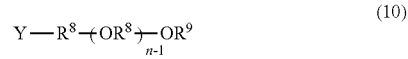

(10)

(In the above formula, Y is a releasable group such as tosyl group or halogen atom, and $R^8$, $R^9$ and "n" are as defined in the formula (5a).)

To convert into a tosyl group, a method in which a reaction with p-toluenesulfonyl chloride is carried out in the presence of a basic catalyst such as tertiary amine exemplified by triethylamine may be preferably employed. To convert into an iodine atom, bromine atom or chlorine atom, conversion may be carried out by an Appel reaction. Stated more specifically, a method in which a reaction with carbon tetrahalide, iodine, methyl iodide, hexaacetone or triphosgene is carried out in the presence of triphenyl phosphine may be preferably employed.

Subsequently, a benzophenone compound having a hydroxyl group is reacted with the substituent of the above formula (10) in an aprotic polar solvent such as dimethyl formamide or dimethyl sulfoxide in the presence of a base such as potassium carbonate to obtain a benzophenone compound substituted by a polyalkylene glycol oligomer chain and represented by the following formula (11).

[CF 18]

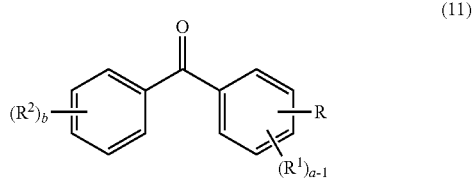

(11)

(In the above formula, R is a group obtained by removing Y from the group represented by the formula (10), and $R^1$, $R^2$, "a" and "b" are as defined in the above formula (1).)

The above benzophenone compound of the formula (11) is subjected to a Stobbe reaction, cyclization reaction, hydrolysis reaction using an alkali or acid, benzyl protection or debenzylation by a hydrolysis reaction using an alkali or acid in accordance with a known method so as to obtain a benzyl-protected carboxylic acid which is represented by the following formula (12).

[CF 19]

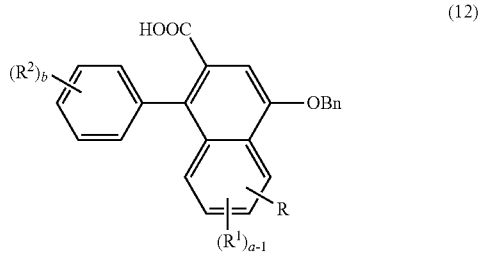

(12)

In the above formula, Bn is a benzyl group, R is as defined in the formula (11), and $R^1$, $R^2$, "a" and "b" are as defined in the formula (1).

The benzyl-protected carboxylic acid is converted into an amine by Curtius rearrangement, Hofmann rearrangement or Lossen rearrangement to prepare a diazonium salt therefrom by a method known per se. This diazonium salt is converted into a bromide by a Sandmeyer reaction and then the obtained bromide is reacted with magnesium or lithium to prepare an organic metal compound. This organic metal compound is reacted with a ketone represented by the following formula (13)

[CF 20]

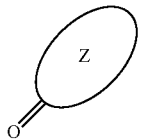

(13)

(In the above formula, the ring Z is as defined in the formula (1).)
in an organic solvent at −80 to 70° C. for 10 minutes to 4 hours, a debenzylation reaction is carried out with hydrogen and palladium carbon, and then a Friedel-Crafts reaction is carried out under a neutral to acidic condition at 10 to 120° C. for 10 minutes to 2 hours to synthesize a naphthol compound represented by the following formula (14).

[CF 21]

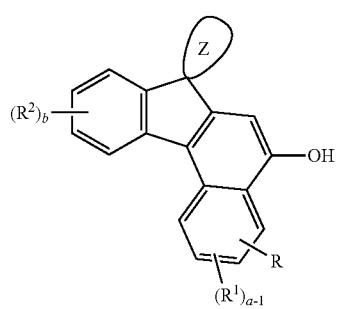

(14)

In the above formula, R is as defined in the formula (1) and $R^1$, $R^2$, ring Z, "a" and "b" are as defined in the formula (1). In the above reaction, the reaction ratio of the above organic metal compound and the ketone represented by the above formula (13) is preferably selected from a range of 1:10 to 10:1 (molar ratio). The reaction temperature is preferably −80 to 70° C. As the solvent, an aprotic organic solvent such as diethyl ether, tetrahydrofuran, benzene or toluene is preferably used. The above Friedel-Crafts reaction under a neutral to acidic condition is preferably carried out by using an acid catalyst such as acetic acid, hydrochloric acid, sulfuric acid, benzene sulfonic acid, p-toluenesulfonic acid or acidic alumina. For this reaction, an aprotic organic solvent such as tetrahydrofuran, benzene or toluene is used.

The chromene compound of the present invention in which the polyalkylene oxide oligomer chain group is substituted to the indeno-position or naphtho-position ($R^1$ or $R^2$) can be obtained by reacting the naphthol compound of the above formula (14) with the propargyl alcohol represented by the above formula (8).

As a method of introducing the polyalkylene oxide oligomer chain group into the propargyl alcohol represented by the above formula (8), after a propargyl alcohol represented by the following formula (15) is synthesized from a benzophenone compound having a polyalkylene oxide oligomer chain group and represented by the above formula (11),

[CF 22]

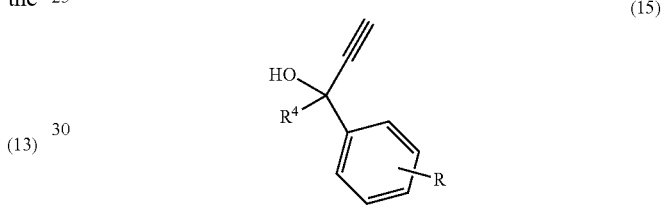

(15)

(In the above formula, R is as defined in the formula (11), and $R^4$ is as defined in the above formula (1).)
the propargyl alcohol is reacted with the naphthol compound of the above formula (7) synthesized on the basis of a reaction method described in theses such as International Publications Nos. WO2001/60881 pamphlet and WO2005/028465 pamphlet to obtain the chromene compound of the present invention in which the polyalkylene oxide oligomer chain group has been substituted to $R^3$ and $R^4$.

Besides the method in which the polyalkylene oxide oligomer chain group has been introduced in advance, it can be introduced after the synthesis of the chromene compound. Stated more specifically, a reactive substituent such as hydroxyl group, primary or secondary amino group or thiol group is substituted to a position into which the polyalkylene oxide oligomer chain group is to be introduced. Then, the precursor of the chromene compound of the present invention having the polyalkylene oxide oligomer chain group is produced by the above method. Thereafter, the reactive substituent of the obtained precursor is reacted with a polyalkylene oxide oligomer having a reactive substituent (this group is preferably a group forming the above divalent bond group L) to produce the chromene compound of the present invention.

For example, the above L can be formed by carrying out an esterification reaction with a polyalkylene oxide oligomer having a carboxyl group. Stated more specifically, the reaction may be carried out in a solvent such as toluene in the presence of a mineral acid such as sulfuric acid or hydrochloric acid, organic acid such as aromatic sulfonic acid, or Lewis acid such as boron fluoride ether by stirring under heating as required and removing the produced water by azeotropy. To remove water in the above esterification reaction, a method of removing water with a desiccant such as anhydrous magnesium sulfate or molecular sieves or a method of removing water in the presence of a dehydrating agent typified by dicyclohexyl carbodiimide may be employed.

The above L can also be formed by carrying out an esterification reaction with a polyalkylene oxide oligomer having a carboxylic acid halide. Stated more specifically, a method in which the produced hydrogen halide is removed in an ether-based solvent such as tetrahydrofuran in the presence of a base such as pyridine or dimethyl aniline by stirring under heating as required may be employed.

The polyalkylene oxide oligomer having a carboxyl group or carboxylic acid halide can be synthesized by a known method. Stated more specifically, a polyalkylene oxide oligomer monoalkyl ether having a carboxyl group can be obtained by reacting the polyalkylene oxide oligomer monoalkyl ether of the above formula (9) with a cyclic acid anhydride such as succinic anhydride in the presence of a basic or acid catalyst. The polyalkylene oxide oligomer monoether having a carboxyl group can also be obtained by reacting an organic metal compound with carbon dioxide after the organic metal compound is prepared by reacting the polyalkylene oxide oligomer monoalkyl ether having a halogen atom and represented by the above formula (10) with magnesium or lithium. A polyalkylene oxide oligomer monoether having a carboxylic acid halide can be obtained by reacting the obtained polyalkylene oxide oligomer monoether having a carboxyl group with thienyl chloride or oxalyl chloride.

While the method of producing the chromene compound of the present invention by introducing the polyalkylene glycol chain group into the indenonaphthopyran moiety has been described, the same method can be employed to introduce another oligomer chain group. Stated more specifically, the same operation should be carried out by using a compound having a polyester oligomer chain (group) or a polyester polyether oligomer chain (group) in place of the compound having a polyalkylene oligomer chain (group).

<Identification of Chromene Compound>

The chromene compound of the present invention is generally existent as a solid or viscous liquid at normal temperature and normal pressure and can be confirmed by the following means. Stated more specifically, it is confirmed by separation operation such as thin-layer chromatography, silica gel column chromatography, high-speed liquid chromatography or gas chromatography that there are no by-products such as raw material compounds and colored matter except for the chromene compound.

When the proton nuclear magnetic resonance spectrum ($^1$H-NMR) of the obtained chromene compound is measured, peaks based on an aromatic proton and an alkene proton appear at a δ of 5.0 to 9.0 ppm and peaks based on the protons of an alkyl group and an alkylene group appear at a δ of 1.0 to 4.0 ppm. The number of protons of each bond group can be known by relatively comparing the spectral intensities of these peaks.

Further, the chromene compound extracted from a photochromic curable composition and a cured body of the photochromic curable composition can be confirmed by the same method as above.

<Combination with Another Photochromic Compound (Photochromic Composition)>

The chromene compound of the present invention dissolves well in an ordinary organic solvent such as toluene, chloroform or tetrahydrofuran. When the chromene compound represented by the above formula (1) is dissolved in this solvent, the obtained solution is generally almost colorless and transparent and exhibits excellent photochromic action that it swiftly develops color when it is irradiated with sunlight or ultraviolet light and swiftly returns to its original colorless state reversibly when light is blocked.

The chromene compound of the present invention may be used in combination with another photochromic compound according to intended use. For example, to obtain various color tones required for photochromic lenses, it can be used in combination with another photochromic compound. As the photochromic compound to be combined with the chromene compound of the present invention, known compounds may be used without restriction. The compounds include fulgide, fulgimide, spirooxazine and chromene. Out of these, chromene compounds are particularly preferred as they can keep a color tone at the time of color development and fading uniformly, can suppress a color shift at the time of color development due to the deterioration of photochromic properties and further can reduce initial coloration. From the viewpoint of suppressing a color shift of color tone at the time of color development and fading due to the difference in environmental dependence, the other photochromic compound is preferably a chromene compound having an oligomer chain. Or, a plurality of the chromene compounds of the present invention are preferably used to adjust a color tone.

To prepare a photochromic composition comprising the chromene compound of the present invention and another chromene compound, the blending ratio of these chromene compounds is suitably determined according to a desired color tone.

<Photochromic Curable Composition>

The chromene compound of the present invention and the above photochromic composition are preferably used in combination with a polymerizable compound to be used as a photochromic curable composition.

In the present invention, the photochromic curable composition preferably has the following blending ratio though it cannot be specified unconditionally as it depends on the color development intensity of the chromene compound, the selected lens material and the thickness of a lens. Stated more specifically, the chromene compound or the photochromic composition of the present invention is used in an amount of 0.001 to 10 parts by mass based on 100 parts by mass of the polymerizable compound.

The optimum amount is preferably adjusted according to use purpose. For example, when the photochromic curable composition is used as a thin-film optical article or a thick-film optical article, the amount is as follows.

Stated more specifically, to form the photochromic curable composition into a thin film like a coating film, for example, a thin film having a thickness of about 100 μm (polymer film obtained by polymerizing the photochromic curable composition), the chromene compound or the photochromic composition of the present invention should be used in an amount of 0.001 to 10 parts by mass based on 100 parts by mass of the other polymerizable monomer in order to adjust a color tone.

To obtain a thick cured body (polymer molded body obtained by polymerizing the photochromic curable composition), for example, a cured body having a thickness of not less than 1 mm, the chromene compound of the present invention or the photochromic composition should be used in an amount of 0.001 to 1 part by mass based on 100 parts by mass of the thick cured body or the other polymerizable monomer which provides the thick cured body in order to adjust a color tone.

<Polymerizable Compound>

Examples of the polymerizable compound (may be referred to as "component (B)") used in the present invention include radically polymerizable compounds (B1), epoxy-based polymerizable compounds (B2), urethane- or urea-based polymerizable compounds (B3) which can form a urethane bond or urea bond and polymerizable compounds (B4) other than the above components (B1) to (B3).

<Radically Polymerizable Compound>

The radically polymerizable compounds (B1) are roughly divided into (meth)acrylic polymerizable compounds having a (meth)acrylic group (B1-1), vinyl-based polymerizable compounds having a vinyl group (B1-2), allyl-based polymerizable compounds having an allyl group (B1-3) and silsesquioxane-based polymerizable compounds (B1-4). Illustrative examples thereof are given below.

(B1-1) Examples of (Meth)Acrylic Polymerizable Compound (B1-1-1) Bifunctional (Meth)Acrylic Polymerizable Compound The photochromic curable composition of the present invention preferably comprises (B1-1-1) a bifunctional (meth)acrylic polymerizable compound. Examples thereof are given below. Specifically, they are compounds represented by the following formulas (12), (13) and (14). The compound represented by the following formula (12) may be simply referred to as "component (B1-1-1-1)", the compound represented by the following formula (13) may be simply referred to as "component (B1-1-1-2)", and the compound represented by the following formula (14) may be simply referred to as "component (B1-1-1-3)" hereinafter. A description is given of a bifunctional (meth)acrylic polymerizable compound having a urethane bond (may be simply referred to as "component (B1-1-1-4)" hereinafter) and a bifunctional (meth)acrylic polymerizable compound (may be simply referred to as "component (B1-1-1-5)" hereinafter) which does not correspond to the above component (B1-1-1-1), the above component (B1-1-1-2), the above component (B1-1-1-3) and the above component (B1-1-1-4).

(B1-1-1-1) compound represented by the following formula (16)

[CF 23]

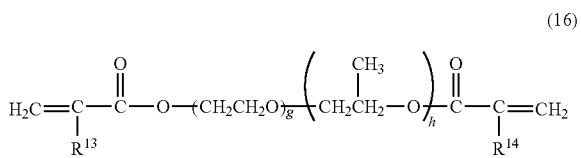

(16)

In the above formula, $R^{13}$ and $R^{14}$ are each a hydrogen atom or methyl group, "" and "h" are each independently an integer of 0 or more, and (g+h) is an average value of 2 to 50.

The polymerizable compound represented by the above formula (16) is generally obtained in the form of a mixture of molecules having different molecular weights. Therefore, "g" and "h" are average values.

Examples of the compound represented by the above formula (16) are given below.

Diethylene glycol dimethacrylate, triethylene glycol dimethacrylate, tetraethylene glycol dimethacrylate, pentaethylene glycol dimethacrylate, pentapropylene glycol dimethacrylate, diethylene glycol diacrylate, triethylene glycol diacrylate, tetraethylene glycol diacrylate, pentaethylene glycol diacrylate, tripropylene glycol diacrylate, tetrapropylene glycol diacrylate, pentapropylene glycol diacrylate, dimethacrylate composed of a mixture of polypropylene glycol and polyethylene glycol (polyethylene has two recurring units and polypropylene has two recurring units), polyethylene glycol dimethacrylate (especially average molecular weight of 330), polyethylene glycol dimethacrylate (especially, average molecular weight of 536), polyethylene glycol dimethacrylate (especially average molecular weight of 736), tripropylene glycol dimethacrylate, tetrapropylene glycol dimethacrylate, polypropylene glycol dimethacrylate (especially average molecular weight of 536), polyethylene glycol diacrylate (especially average molecular weight of 258), polyethylene glycol diacrylate (especially average molecular weight of 308), polyethylene glycol diacrylate (especially average molecular weight of 508), polyethylene glycol diacrylate (especially average molecular weight of 708) and polyethylene glycol methacrylate acrylate (especially average molecular weight of 536).

(B1-1-1-2) Compound Represented by the Following Formula (17)

[CF 24]

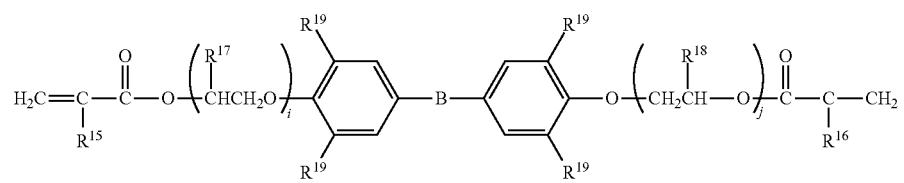

(17)

In the above formula, $R^{15}$ and $R^{16}$ are each a hydrogen atom or methyl group, $R^{17}$ and $R^{18}$ are each a hydrogen atom or methyl group, $R^{19}$ is a hydrogen atom or halogen atom, B is one of —O—, —S—, —(SO$_2$)—, —CO—, —CH$_2$—, —CH—CH—, —C(CH$_3$)$_2$— and —C(CH$_3$) (C$_6$H$_8$)—, "i" and "j" are each an integer of 1 or more, and (i+j) is an average value of 2 to 30.

The polymerizable compound represented by the above formula (17) is generally obtained in the form of a mixture of molecules having different molecular weights. Therefore, "i" and "j" are average values.

Examples of the compound represented by the above formula (17) include the following bisphenol A di(meth) acrylates.

2,2-bis[4-methacryloyloxy.ethoxy)phenyl]propane (i+j=2), 2,2-bis[4-methacryloyloxy.diethoxy)phenyl]propane (i+j=4), 2,2-bis[4-methacryloyloxy.polyethoxy)phenyl] propane (i+j=7),
2,2-bis(3,5-dibromo-4-methacryloyloxyethoxyphenyl)propane (i+j=2), 2,2-bis(4-methacryloyloxydipropoxyphenyl)propane (i+j=4), 2,2-bis[4-acryloyloxydiethoxy)phenyl]propane (i+j=4), 2,2-bis[4-acryloyloxypolyethoxy)phenyl]propane (i+j=3), 2,2-bis[4-acryloyloxypolyethoxy)phenyl]propane (i+j=7),
2,2-bis[4-methacryloyloxy(polyethoxy)phenyl]propane (i+j=10),
2,2-bis[4-methacryloyloxy(polyethoxy)phenyl]propane (i+j=17),
2,2-bis[4-methacryloyloxy(polyethoxy)phenyl]propane (i+j=30),
2,2-bis[4-acryloyloxy(polyethoxy)phenyl]propane (i+j=10) and
2,2-bis[4-acryloyloxy(polyethoxy)phenyl]propane (i+j=20).

(B1-1-1-3) Compound Represented by the Following Formula (18)

[CF 25]

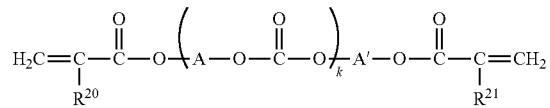

(18)

In the above formula, $R^{20}$ and $R^{21}$ are each a hydrogen atom or methyl group, "k" is an average value of 1 to 20, A and A' may be the same or different and each a linear or branched alkylene group having 2 to 15 carbon atoms, and when a plurality of A's are existent, A's may be the same or different.

The compound represented by the above formula (18) can be produced by reacting a polycarbonate diol with (meth)acrylic acid.

The following compounds may be used as the polycarbonate diol which can be used herein. Examples of the polycarbonate diol include polycarbonate diols (number average molecular weight of 500 to 2,000) obtained by the phosgenation of a polyalkylene glycol such as trimethylene glycol, tetramethylene glycol, pentamethylene glycol, hexamethylene glycol, octamethylene glycol or nonamethylene glycol; polycarbonate diols (number average molecular weight of 500 to 2,000) obtained by the phosgenation of a mixture of two or more polyalkylene glycols, for example, a mixture of trimethylene glycol and tetramethylene glycol, a mixture of tetramethylene glycol and hexamethylene diglycol, a mixture of pentamethylene glycol and hexamethylene glycol, a mixture of tetramethylene glycol and octamethylene glycol or a mixture of hexamethylene glycol and octamethylene glycol; and polycarbonate diols (number average molecular weight of 500 to 2,000) obtained by the phosgenation of 1-methyl trimethylene glycol.

(B1-1-1-4) Bifunctional (Meth)Acrylic Polymerizable Compound Having a Urethane Bond A typical example of the component (B1-1-1-4) is a reaction product of a polyol and a polyisocyanate. Examples of the polyisocyanate include hexamethylene diisocyanate, isophorone diisocyanate, lysine isocyanate, 2,2,4-hexamethylene diisocyanate, dimeric acid diisocyanate, isopropylidenebis-4-cyclohexyl isocyanate, dicyclohexylmethane diisocyanate, norbornene diisocyanate or methylcyclohexane diisocyanate.

Meanwhile, examples of the polyol include polyalkylene glycols having the recurring unit of ethylene oxide having 2 to 4 carbon atoms, propylene oxide or hexamethylene oxide, and polyester diols such as polycaprolactone diol. Polycarbonate diols, polybutadiene diols, ethylene glycol, propylene glycol, 1,3-propanediol, 1,4-butanediol, 1,5-pentanediol, 1,6-hexanediol, 1,9-nonanediol, 1,8-nonanediol, neopentyl glycol, diethylene glycol, dipropylene glycol, 1,4-cyclohexanediol and 1,4-cyclohexane dimethanol are also included.

Urethane (meth)acrylates which are reaction mixtures obtained by urethane prepolymers obtained by reacting the above polyisocyanate and polyol so as to be reacted further with 2-hydroxy (meth)acrylate, and which are reaction mixtures obtained by directly reacting the above diisocyanate with 2-hydroxy (meth)acrylate may also be used.

Examples of the bifunctional (meth)acrylic polymerizable compound having a urethane bond include U-2PPA (molecular weight of 482), UA-122P (molecular weight of 1,100), U-122P (molecular weight of 1,100), U-108A, U-200PA, UA-511, U-412A, UA-4100, UA-4200, UA-4400, UA-2235PE, UA-160TM, UA-6100, UA-6200, U-108, UA-4000 and UA-512 manufactured by Shin-Nakamura Chemical Co., Ltd., EB4858 (molecular weight of 454) manufactured by Daicel-UCB Co., Ltd. and UX-2201, UX3204, UX4101, 6101, 7101 and 8101 manufactured by Nippon Kayaku Co., Ltd.

(B1-1-1-5) Other Bifunctional (Meth)Acrylic Polymerizable Compound

Examples of the component (B1-1-1-5) include compounds having a (meth)acrylic group at both ends of an alkylene group which may have a substituent. Compounds having an alkylene group with 6 to 20 carbon atoms are preferred as the component (B1-1-1-5). Examples thereof include 1,6-hexanediol diacrylate, 1,6-hexanediol dimethacrylate, 1,9-nonanediol diacrylate, 1,9-nonanediol dimethacrylate, 1,10-decanediol diacrylate and 1,10-decanediol dimethacrylate.

Other examples of the component (B1-1-1-5) include bifunctional (meth)acrylate monomers containing a sulfur atom. The sulfur atom preferably forms part of a molecular chain as a sulfide group. The bifunctional (meth)acrylate monomers include bis(2-methacryloyloxyethylthioethyl)sulfide,
bis(methacryloyloxyethyl)sulfide,
bis(acryloyloxyethyl)sulfide,
1,2-bis(methacryloyloxyethylthio)ethane,
1,2-bis(acryloyloxyethyl)ethane,
bis(2-methacryloyloxyethylthioethyl)sulfide,
bis(2-acryloyloxyethylthioethyl)sulfide,
1,2-bis(methacryloyloxyethylthioethylthio)ethane,
1,2-bis(acryloyloxyethylthioethylthio)ethane,
1,2-bis(methacryloyloxyisopropylthioisopropyl)sulfide and
1,2-bis(acryloyloxyisopropylthioisopropyl)sulfide.

The above compounds listed as examples of the above components (B1-1-1-1), (B1-1-1-2), (B1-1-1-3), (B1-1-1-4) and (B1-1-1-5) may be used alone or in combination. When a plurality of the compounds are used, the amount of the component (B1-1-1) is the total amount of the compounds.

A description is subsequently given of the polyfunctional (meth)acrylic polymerizable compound (B1-1-2)

(B1-1-2) Polyfunctional (Meth)Acrylic Polymerizable Compound

Examples of the component (B1-1-2) include compounds represented by the following formula (8) (may be simply referred to as "component (B1-1-2-1)" hereinafter), polyfunctional (meth)acrylic polymerizable compounds having a urethane bond (may be simply referred to as "component (B1-1-2-2)" hereinafter) and polyfunctional (meth)acrylic polymerizable compounds (may be simply referred to as "component (B1-1-2-3)" hereinafter) which do not correspond to the above component (B1-1-2-1) and the above component (B1-1-2-2).

(B1-1-2-1) Compound Represented by the Following Formula (19)

A compound represented by the following formula (19) is used as the polyfunctional (meth)acrylate polymerizable compound.

[CF 26]

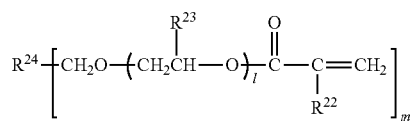

(19)

In the above formula, $R^{22}$ is a hydrogen atom or methyl group, $R^{23}$ is a hydrogen atom or alkyl group having 1 to 2 carbon atoms, $R^{24}$ is a trivalent to hexavalent organic group having 1 to 10 carbon atoms, "l" is an average value of 0 to 3, and "m" is 3 to 6.

The alkyl group having 1 to 2 carbon atoms represented by $R^{23}$ is preferably a methyl group. Examples of the organic group represented by $R^{24}$ include groups derived from a polyol, trivalent to hexavalent hydrocarbon groups and trivalent to hexavalent organic groups containing a urethane bond.

Examples of the compound represented by the above formula (19) include trimethylolpropane trimethacrylate, trimethylolpropane triacrylate, tetramethylolmethane trimethacrylate, tetramethylolmethane triacrylate, tetramethylolmethane tetramethacrylate, tetramethylolmethane tetraacrylate, trimethylolpropane triethylene glycol trimethacrylate, trimethylolpropane triethylene glycol triacrylate, ditrimethylolpropane tetramethacrylate and ditrimethylolpropane tetraacrylate.

(B1-1-2-2) Polyfunctional (Meth)Acrylicpolymerizable Compound Having a Urethane Bond The component (B1-1-2-2) is a compound obtained by reacting a polyisocyanate compound which has been explained for the component (B1-1-1-4) with a polyol compound such as glycerin, trimethylolpropane, pentaerythritol or dipentaerythritol and having three or more (meth)acrylate groups in the molecule. Commercially available products of the compound include U-4HA (molecular weight of 596, 4 functional groups), U-6HA (molecular weight of 1,019, 6 functional groups), U-6LPA (molecular weight of 818, 6 functional groups) and U-15HA (molecular weight of 2,300, 15 functional groups) manufactured by Shin-Nakamura Chemical Co., Ltd.

(B1-1-2-3) Other Polyfunctional (Meth)Acrylic Polymerizable Compound

The component (B1-1-2-3) is a compound obtained by modifying the terminal of a polyester compound with a (meth)acrylic group. Various commercially available polyester (meth)acrylate compounds which differ in the molecular weight of a polyester compound as a raw material and the modification amount of the (meth)acrylic group may be used. Examples of the compound include tetrafunctional polyester oligomers (molecular weight of 2,500 to 3,500, EB80 of Daicel-UCB Co., Ltd., etc.), hexafunctional polyester oligomers (molecular weight of 6,000 to 8,000, 5B450 of Daicel-UCB Co., Ltd., etc.), hexafunctional polyester oligomers (molecular weight of 45,000 to 55,000, EB1830 of Daicel-UCB Co., Ltd., etc.), and tetrafunctional polyester oligomers (GX8488B of DKS Co., Ltd. having a molecular weight of 10,000, etc.).

When the component (B1-1-2) ((component (B1-1-2-1), component (B-1-1-2-2) or component (B1-1-2-3)) exemplified above is used, crosslinking density is improved by polymerization, thereby making it possible to increase the surface hardness of the obtained cured body. Therefore, to obtain a photochromic cured body (laminate) by the coating method, the component (B1-1-2) is preferably contained. Out of the components (B1-1-2), the component (B1-1-2-1) is preferably used.

The above compounds listed as examples of the above components (B1-1-2-1), (B1-1-2-2) and (B1-1-2-3) may be used alone or in combination. When a plurality of the compounds are used, the amount of the component (B1-1-2) is the total amount of the compounds.

A description is subsequently given of the monofunctional (meth)acrylic polymerizable compound (B1-1-3).

(B1-1-3) Monofunctional (Meth)Acrylic Polymerizable Compound

A compound represented by the following formula (20) is used as the component (B1-1-3).

[CF 27]

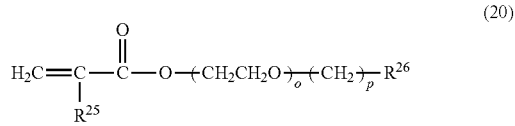

(20)

In the above formula, $R^{25}$ is a hydrogen atom or methyl group, $R^{26}$ is a hydrogen atom, methyldimethoxysilyl group, trimethoxysilyl group or glycidyl group, "o" is an integer of 0 to 10 and "p" is an integer of 0 to 20.

Examples of the compound represented by the above formula (20) are given below.

Methoxy polyethylene glycol methacrylate (especially average molecular weight of 293), methoxy polyethylene glycol methacrylate (especially average molecular weight of 468), methoxy polyethylene glycol acrylate (especially average molecular weight of 218), methoxy polyethylene glycol acrylate (especially average molecular weight of 454), stearyl methacrylate, lauryl methacrylate, methyl acrylate, ethyl acrylate, butyl acrylate, octyl acrylate, lauryl acrylate, γ-methacryloyloxypropyl trimethoxysilane, γ-methacryloyloxypropylmethyl dimethoxysilane and glycidyl methacrylate.

(B1-2) Vinyl-Based Polymerizable Compound

Examples of the vinyl-based polymerizable compound having a vinyl group include methyl vinyl ketone, ethyl vinyl ketone, ethyl vinyl ether, styrene, vinyl cyclohexane, butadiene, 1,4-pentadiene, divinyl sulfide, divinyl sulfone, 1,2-divinylbenzene, 1,3-divinyl-1,1,3,3-tetramethylpropane disiloxane, diethylene glycol divinyl ether, divinyl adipate, divinyl sebacate, ethylene glycol divinyl ether, divinyl sulfoxide, divinyl persulfide, dimethyl divinylsilane, 1,2,4-trivinyl cyclohexane, methyl trivinylsilane, α-methylstyrene and α-methylstyrene dimer.

Out of the above vinyl-based polymerizable compounds, α-methylstyrene and α-methylstyrene dimer function as a polymerization regulator and improve the moldability of a photochromic composition.

(B1-3) Allyl-Based Polymerizable Compound

Examples of the allyl-based polymerizable compound having an allyl group are given below. Diethylene glycol bisallyl carbonate, methoxy polyethylene glycol allyl ether (especially average molecular weight of 550), methoxy polyethylene glycol allyl ether (especially average molecular weight of 350), methoxy polyethylene glycol allyl ether (especially average molecular weight of 1,500), polyethylene glycol allyl ether (especially average molecular weight of 450), methoxy polyethylene glycol-polypropylene glycol allyl ether (especially average molecular weight of 750), butoxy polyethylene glycol-polypropylene glycol allyl ether (especially average molecular weight of 1,600), methacryloyloxy polyethylene glycol-polypropylene glycol allyl ether (especially average molecular weight of 560), phenoxy polyethylene glycol allyl ether (especially average molecular weight of 600), methacryloyloxy polyethylene glycol allyl ether (especially average molecular weight of 430), acryloyloxy polyethylene glycol allyl ether (especially average molecular weight of 420), vinyloxy polyethylene glycol allyl ether (especially average molecular weight of 560), styryloxy polyethylene glycol allyl ether (especially average molecular weight of 650) and methoxy polyethylene thioglycol allyl thioether (especially average molecular weight of 730)

Since the allyl-based polymerizable compound serves as a chain transfer agent, the photochromic properties (color optical density, fading speed) of the curable composition can be improved.

(B1-4) Silsesquioxane Polymerizable Compound

The silsesquioxane polymerizable compound may take a cage-like, ladder-like or random molecular structure and has a radically polymerizable group such as (meth)acrylic group.

Examples of the silsesquioxane polymerizable compound include a compound represented by the following formula (21).

[CF 28]

$$R^{27}\!-\!(SiO_{3/2})_q \qquad (21)$$

In the above formula, "q" is the degree of polymerization which is an integer of 3 to 100, a plurality of $R^{27}$'s may be the same or different and each a radically polymerizable group, organic group containing a radically polymerizable group, hydrogen atom, alkyl group, cycloalkyl group, alkoxy group or phenyl group, and at least one $R^{27}$ is a radically polymerizable group or organic group containing a radically polymerizable group.

Examples of the radically polymerizable group or organic group containing a radically polymerizable group represented by $R^{27}$ include (meth)acrylic group; organic groups having a (meth)acrylic group such as (meth)acryloyloxypropyl group and (3-(meth)acryloyloxypropyl)dimethylsiloxy group; allyl group; organic groups having an allyl group such as allylpropyl group and allylpropyldimethylsiloxy group; vinyl group; and organic groups having a vinyl group such as vinylpropyl group and vinyldimethylsiloxy group.

<Epoxy-Based Polymerizable Compound>

The epoxy-based polymerizable compounds (B2) are roughly divided into aliphatic epoxy compounds, alicyclic epoxy compounds and aromatic epoxy compounds, and examples thereof are given below.

The aliphatic epoxy compounds include ethylene oxide, 2-ethyloxirane, butyl glycidyl ether, phenyl glycidyl ether, 2,2'-methylene bisoxirane, 1,6-hexanediol diglycidyl ether, ethylene glycol diglycidyl ether, diethylene glycol diglycidyl ether, triethylene glycol diglycidyl ether, tetraethylene glycol diglycidyl ether, nonaethylene glycol diglycidyl ether, propylene glycol diglycidyl ether, dipropylene glycol diglycidyl ether, tripropylene glycol diglycidyl ether, tetrapropylene glycol diglycidyl ether, nonapropylene glycol diglycidyl ether, neopentyl glycol diglycidyl ether, trimethylolpropane triglycidyl ether, glycerol triglycidyl ether, diglycerol tetraglycidyl ether, pentaerythritol tetraglycidyl ether, diglycidyl ethers of tris(2-hydroxyethyl)isocyanurate and triglycidyl ethers of tris(2-hydroxyethyl) isocyanurate.

The alicyclic epoxy compounds include isophoronediol diglycidyl ether and bis-2,2-hydroxycyclohexylpropane diglycidyl ether.

The aromatic epoxy compounds include resorcin diglycidyl ether, bisphenol A diglycidyl ether, bisphenol F diglycidyl ether, bisphenol S diglycidyl ether, orthophthalic acid diglycidyl ester, phenol novolak polyglycidyl ether and cresol novolak polyglycidyl ether.

Besides the above compounds, epoxy-based polymerizable compounds having a sulfur atom in the molecule in addition to an epoxy group may also be used. The sulfur atom-containing epoxy-based polymerizable compounds contribute especially to the improvement of refractive index and include chain aliphatic and cyclic aliphatic compounds exemplified by the following compounds.

The chain aliphatic sulfur atom-containing epoxy-based polymerizable compounds include bis(2,3-epoxypropyl)sulfide,
bis(2,3-epoxypropyl)disulfide,
bis(2,3-epoxypropylthio)methane,
1,2-bis(2,3-epoxypropylthio)ethane,
1,2-bis(2,3-epoxypropylthio)propane,
1,3-bis(2,3-epoxypropylthio)propane,
1,3-bis(2,3-epoxypropylthio)-2-methylpropane,
1,4-bis(2,3-epoxypropylthio)butane,
1,4-bis(2,3-epoxypropylthio)-2-methylbutane,
1,3-bis(2,3-epoxypropylthio)butane,
1,5-bis(2,3-epoxypropylthio)pentane,
1,5-bis(2,3-epoxypropylthio)-2-methylpentane,
1,5-bis(2,3-epoxypropylthio)-3-thiapentane,
1,6-bis(2,3-epoxypropylthio)hexane,
1,6-bis(2,3-epoxypropylthio)-2-methylhexane,
3,8-bis(2,3-epoxypropylthio)-3,6-dithiaoctane,
1,2,3-tris(2,3-epoxypropylthio)propane,
2,2-bis(2,3-epoxypropylthio)-1,3-bis(2,3-epoxypropylthiomethyl)propane and
2,2-bis(2,3-epoxypropylthiomethyl)-1-(2,3-epoxypropylthio)butane.

The cyclic aliphatic sulfur atom-containing epoxy-based polymerizable compounds include
1,3-bis(2,3-epoxypropylthio)cyclohexane,
1,4-bis(2,3-epoxypropylthio)cyclohexane,
1,3-bis(2,3-epoxypropylthiomethyl)cyclohexane,
1,4-bis(2,3-epoxypropylthiomethyl)cyclohexane,
2,5-bis(2,3-epoxypropylthiomethyl)-1,4-dithiane,
2,5-bis(<2-(2,3-epoxypropylthio)ethyl>thiomethyl)-1,4-dithiane and
2,5-bis(2,3-epoxypropylthiomethyl)-2,5-dimethyl-1,4-dithiane <Urethane-Based Polymerizable Compound (Including Urea-Based Polymerizable Compound)>

The polymerization recurring unit of the urethane-based polymerizable compound (B3) is linked by a urethane bond or urea bond. For example, the urethane bond is formed by a reaction between a polyol and a polyisocyanate and includes a thiourethane bond formed by a reaction between a polyol and a polyisothiocyanate or a reaction between a polythiol and a polyisothioisocyanate.

The urea bond is also formed by a reaction between a polyamine and a polyisocyanate and includes a thiourea bond formed by a reaction between a polyamine and a polyisothiocyanate.

As understood from the above explanation, in the present invention, a plurality of compounds are selected from polyols (B3-1), polythiols (B3-2), polyamines (B3-3), polyisocyanates (B3-4) and polyisothiocyanates (B3-5) and used as the urethane- or urea-based polymerizable compounds so as to form the above urethane bond (thiourethane bond) or urea bond (thiourea bond).

The following compounds are used as a type of the urethane-based polymerizable compound.

(B3-1) Polyol

The polyol is a compound having at least two OH groups in one molecule, and typical examples thereof include di-, tri-, tetra-, penta- and hexa-hydroxy compounds, polyesters having at least two OH groups in one molecule (polyester polyols), polyethers having at least two OH groups in one molecule (to be referred to as "polyether polyols" hereinafter), polycarbonates having at least two OH groups in one molecule (polycarbonate polyols), polycaprolactones having at least two OH groups in one molecules (polycaprolactone polyols) and acrylic polymers having at least two OH groups in one molecule (polyacrylic polyols).

Examples of these compounds are given below.

Aliphatic alcohols include ethylene glycol, diethylene glycol, propylene glycol, dipropylene glycol, butylene glycol, neopentyl glycol, glycerin, trimethylolethane, trimethylolpropane, butanetriol, 1,2-methyl glycoside, pentaerythritol, dipentaerythritol, tripentaerythritol, sorbitol, erythritol, threitol, ribitol, arabinitol, xylitol, allitol, mannitol, dorcitol, iditol, glycol, inositol, hexanetriol, triglycerol, diglycerol, triethylene glycol, polyethylene glycol, tris(2-hydroxyethyl) isocyanurate, cyclobutanediol, cyclopentanediol, cyclohexanediol, cycloheptanediol, cyclooctanediol, cyclohexanedimethanol, hydroxypropyl cyclohexanol, tricyclo[5,2,1,0,2,6]decane-dimethanol, bicyclo[4,3,0]-nonanediol, dicyclohexanediol, tricyclo[5,3,1,1]dodecanediol, bicyclo[4,3,0]nonanedimethanol, tricyclo[5,3,1,1]dodecane-diethanol, hydroxypropyl tricyclo[5,3,1,1]dodecanol, spiro[3,4]octanediol, butyl cyclohexanediol, 1,1'-bicyclohexylidenediol, cyclohexanetriol, maltitol and lactitol.

Aromatic alcohols include dihydroxynaphthalene, trihydroxynaphthalene, tetrahydroxynaphthalene, dihydroxybenzene, benzenetriol, biphenyltetraol, pyrogallol, (hydroxynaphthyl)pyrogallol, trihydroxy phenanthrene, bisphenol A, bisphenol F, xylylene glycol and tetrabromobisphenol A.

Sulfur-containing polyols include
bis-[4-(hydroxyethoxy)phenyl]sulfide,
bis-[4-(2-hydroxypropoxy)phenyl]sulfide,
bis-[4-(2,3-dihydroxypropoxy)phenyl]sulfide,
bis-[4-(4-hydroxycyclohexyloxy)phenyl]sulfide and
bis-[2-methyl-4-(hydroxyethoxy)-6-butylphenyl]sulfide.

Compounds obtained by adding three or less molecules on average per hydroxyl group of ethylene oxide and/or propylene oxide to the above sulfur-containing polyols include di-(2-hydroxyethyl)sulfide, bis(2-hydroxyethyl)disulfide, 1,4-dithiane-2,5-diol, bis(2,3-dihydroxypropyl)sulfide, tetrakis(4-hydroxy-2-thiabutyl)methane, bis(4-hydroxyphenyl)sulfone, tetrabromobisphenol S, tetramethylbisphenol S, 4,4'-thiobis(6-tert-butyl-3-methylphenol) and 1,3-bis(2-hydroxyethylthioethyl)-cyclohexane.

The polyester polyols include compounds obtained by a condensation reaction between a polyol and a polybasic acid.

The polyether polyols include compounds obtained by a reaction between a compound having at least two active hydrogen-containing groups in the molecule and an alkylene oxide and modified products thereof.

The polycaprolactone polyols include compounds obtained by the ring-opening polymerization of ε-caprolactone.

The polycarbonate polyols include compounds obtained by the phosgenation of at least one low-molecular weight polyol and compounds obtained by transesterification using ethylene carbonate, diethyl carbonate or diphenyl carbonate.

The polyacrylicpolyols include compounds obtained by the copolymerization of an acrylic acid ester or methacrylic acid ester containing a hydroxyl group and a monomer copolymerizable with these esters.

(B3-2) Polythiol

The polythiol is a compound having at least two SH groups in one molecule, and examples thereof include the following compounds.

Aliphatic polythiols include methanedithiol,
1,2-ethanedithiol, 1,1-propanedithiol, 1,2-propanedithiol,
1,3-propanedithiol, 2,2-propanedithiol, 1,6-hexanedithiol,
1,2,3-propanetrithiol, tetrakis(mercaptomethyl)methane,
1,1-cyclohexanedithiol, 1,2-cyclohexanedithiol,
2,2-dimethylpropane-1,3-dithiol,
3,4-dimethoxybutane-1,2-dithiol,
2-methylcyclohexane-2,3-dithiol,
bicyclo[2,2,1]hepta-exo-cis-2,3-dithiol,
1,1-bis(mercaptomethyl)cyclohexane, thiomalic acid bis(2-mercaptoethyl ester), 2,3-dimercaptosuccinic acid (2-mercaptoethyl ester),
2,3-dimercapto-1-propanol(2-mercaptoacetate),
2,3-dimercapto-1-propanol(3-mercaptoacetate), diethylene glycol bis(2-mercaptoacetate), diethylene glycol bis(3-mercaptopropionate), 1,2-dimercaptopropylmethyl ether,
2,3-dimercaptopropylmethyl ether,
2,2-bis(mercaptomethyl)-1,3-propanedithiol,
bis(2-mercaptoethyl)ether, ethylene glycol bis(2-mercaptoacetate), ethylene glycol bis(3-mercaptopropionate),
1,4-bis(3-mercaptobutyryloxy)butane,
1,4-butanediol-bis(3-mercaptopropionate),
1,4-butanediol-bis(thioglycolate),
1,6-hexanediol-bis(thioglycolate), tetraethylene glycol bis (3-mercaptopropionate), trimethylolpropane tris(2-mercaptoacetate), trimethylolpropane tris(3-mercaptopropionate), trimethylolethane tris(3-mercaptobutyrate), trimethylolpropane tris(3-mercaptobutyrate), pentaerythritol tetrakis(2-mercaptoacetate), pentaerythritol tetrakis (3-mercaptopropionate),
1,2-bis(2-mercaptoethylthio)-3-mercaptopropane,
dipentaerythritol hexakis(3-mercaptopropionate),
pentaerythritol tetrakis(3-mercaptobutyrate), 1,4-bis(3-mercaptobutyryloxy)butane, trimethylolpropane tris(3-mercaptobutyrate), trimethylolethane tris(3-mercaptobutyrate),
1,2-bis[(2-mercaptoethyl)thio]-3-mercaptopropane,
2-mercaptomethyl-1,3-propanedithiol,
2-mercaptomethyl-1,4-butanedithiol,
2,4,5-tris(mercaptomethyl)-1,3-dithiolane,
2,2-bis(mercaptomethyl)-1,4-butanedithiol,
4,4-bis(mercaptomethyl)-3,5-dithiaheptane-1,7-dithiol, 2,3-bis(mercaptomethyl)-1,4-butanedithiol,
2,6-bis(mercaptomethyl)-3,5-dithiaheptane-1,7-dithiol,
4-mercaptomethyl-1,8-dimercapto-3,6-dithiaoctane,
2,5-bismercaptomethyl-1,4-dithiane,
1,1,3,3-tetrakis(mercaptomethylthio)propane,
5,7-dimercaptomethyl-1,11-dimercapto-3,6,9-trithiaundecane,
4,7-dimercaptomethyl-1,11-dimercapto-3,6,9-trithiaundecane,
4,8-dimercaptomethyl-1,11-dimercapto-3,6,9-trithiaundecane
and 4-mercaptomethyl-1,8-dimercapto-3,6-dithiaoctane.

Aromatic polythiols include 1,2-dimercaptobenzene,
1,3-dimercaptobenzene, 1,4-dimercaptobenzene,
1,2-bis(mercaptomethyl)benzene,
1,3-bis(mercaptomethyl)benzene,
1,4-bis(mercaptomethyl)benzene,
1,2-bis(mercaptoethyl)benzene,
1,3-bis(mercaptoethyl)benzene,
1,4-bis(mercaptoethyl)benzene,
1,2-bis(mercaptomethoxy)benzene,
1,3-bis(mercaptomethoxy)benzene,
1,4-bis(mercaptomethoxy)benzene,
1,2-bis(mercaptoethoxy)benzene,
1,3-bis(mercaptoethoxy)benzene,
1,4-bis(mercaptoethoxy)benzene, 1,2,3-trimercaptobenzene,
1,2,4-trimercaptobenzene, 1,3,5-trimercaptobenzene,
1,2,3-tris(mercaptomethyl)benzene,
1,2,4-tris(mercaptomethyl)benzene,
1,3,5-tris(mercaptomethyl)benzene,
1,2,3-tris(mercaptoethyl)benzene,
1,2,4-tris(mercaptoethyl)benzene,
1,3,5-tris(mercaptoethyl)benzene,
1,2,3-tris(mercaptomethoxy)benzene,
1,2,4-tris(mercaptomethoxy)benzene,
1,3,5-tris(mercaptomethoxy)benzene,
1,2,3-tris(mercaptoethoxy)benzene,
1,2,4-tris(mercaptoethoxy)benzene,
1,3,5-tris(mercaptoethoxy)benzene,
1,2,3,4-tetramercaptobenzene, 1,2,3,5-tetramercaptobenzene,
1,2,4,5-tetramercaptobenzene,
1,2,3,4-tetrakis(mercaptomethyl)benzene,
1,2,3,5-tetrakis(mercaptomethyl)benzene,
1,2,4,5-tetrakis(mercaptomethyl)benzene,
1,2,3,4-tetrakis(mercaptoethyl)benzene,
1,2,3,5-tetrakis(mercaptoethyl)benzene,
1,2,4,5-tetrakis(mercaptoethyl)benzene,
1,2,3,4-tetrakis(mercaptoethyl)benzene,
1,2,3,5-tetrakis(mercaptomethoxy)benzene,
1,2,4,5-tetrakis(mercaptomethoxy)benzene,
1,2,3,4-tetrakis(mercaptoethoxy)benzene,
1,2,3,5-tetrakis(mercaptoethoxy)benzene,
1,2,4,5-tetrakis(mercaptoethoxy)benzene,
2,2'-dimercaptobiphenyl, 4,4'-dimercaptobiphenyl,
4,4'-dimercaptobibenzyl, 2,5-toluenedithiol,
3,4-toluenedithiol, 1,4-naphthalenedithiol,
1,5-naphthalenedithiol, 2,6-naphthalenedithiol,
2,7-naphthalenedithiol, 2,4-dimethylbenzene-1,3-dithiol,
4,5-dimethylbenzene-1,3-dithiol, 9,10-anthracene dimethanethiol, 1,3-di(p-methoxyphenyl)propane-2,2-dithiol,
1,3-diphenylpropane-2,2-dithiol, phenylmethane-1,1-dithiol,
2,4-di(p-mercaptophenyl)pentane and
1,4-bis(mercaptopropylthiomethyl)benzene.

Halogen substituted aromatic polythiols include
2,5-dichlorobenzene-1,3-dithiol,
1,3-di(p-chlorophenyl)propane-2,2-dithiol,
3,4,5-tribromo-1,2-dimercaptobenzene and
2,3,4,6-tetrachloro-1,5-bis(mercaptomethyl)benzene.

Heterocyclic polythiols include
2-methylamino-4,6-dithiol-sym-triazine,
2-ethylamino-4,6-dithiol-sym-triazine,
2-amino-4,6-dithiol-sym-triazine,
2-morpholino-4,6-dithiol-sym-triazine,
2-cyclohexylamino-4,6-dithiol-sym-triazine,
2-methoxy-4,6-dithiol-sym-triazine,
2-phenoxy-4,6-dithiol-sym-triazine,
2-thiobenzeneoxy-4,6-dithiol-sym-triazine,
2-thiobutyloxy-4,6-dithiol-sym-triazine and
1,3,5-tris(3-mercaptobutyryloxyethyl)-1,3,5-triazine-2,4,6 (1H,3H,5H)-trione.

Aromatic polythiols containing a sulfur atom in addition to a mercapto group include
1,2-bis(mercaptomethylthio)benzene,
1,3-bis(mercaptomethylthio)benzene,
1,4-bis(mercaptomethylthio)benzene,
1,2-bis(mercaptoethylthio)benzene,
1,3-bis(mercaptoethylthio)benzene,
1,4-bis(mercaptoethylthio)benzene,
1,2,3-tris(mercaptomethylthio)benzene,
1,2,4-tris(mercaptomethylthio)benzene,
1,3,5-tris(mercaptomethylthio)benzene,
1,2,3-tris(mercaptoethylthio)benzene,
1,2,4-tris(mercaptoethylthio)benzene,
1,3,5-tris(mercaptoethylthio)benzene,
1,2,3,4-tetrakis(mercaptomethylthio)benzene,
1,2,3,5-tetrakis(mercaptomethylthio)benzene,
1,2,4,5-tetrakis(mercaptomethylthio)benzene,
1,2,3,4-tetrakis(mercaptoethylthio)benzene,
1,2,3,5-tetrakis(mercaptoethylthio)benzene,
1,2,4,5-tetrakis(mercaptoethylthio)benzene, and the nucleus alkylated products of the above polythiols.

Aliphatic polythiols containing a sulfur atom in addition to a mercapto group include bis(mercaptomethyl)sulfide,
bis(mercaptoethyl)sulfide, bis(mercaptopropyl)sulfide,
bis(mercaptomethylthio)methane,
bis(2-mercaptoethylthio)methane,
bis(3-mercaptopropyl)methane,
1,2-bis(mercaptomethylthio)ethane,
1,2-(2-mercaptoethylthio)ethane,
1,2-(3-mercaptopropyl)ethane,
1,3-bis(mercaptomethylthio)propane,
1,3-bis(2-mercaptoethylthio)propane,
1,3-bis(3-mercaptopropylthio)propane,
1,2-bis(2-mercaptoethylthio)-3-mercaptopropane,
2-mercaptoethylthio-1,3-propanedithiol,
1,2,3-tris(mercaptomethylthio)propane,
1,2,3-tris(2-mercaptoethylthio)propane,
1,2,3-tris(3-mercaptopropylthio)propane,
tetrakis(mercaptomethylthiomethyl)methane,
tetrakis(2-mercaptoethylthiomethyl)methane,
tetrakis(3-mercaptopropylthiomethyl)methane,
bis(2,3-dimercaptopropyl)sulfide,
2,5-dimercapto-1,4-dithiane, bis(mercaptomethyl)disulfide,
bis(mercaptoethyl)disulfide and
bis(mercaptopropyl)disulfide.

Thioglycolic acid or mercaptopropionic acid esters of the above compounds include hydroxymethyl sulfide bis(2-mercaptoacetate), hydroxymethyl sulfide bis(3-mercaptopropionate), hydroxyethyl sulfide bis(2-mercaptoacetate), hydroxyethyl sulfide bis(3-mercaptopropionate), hydroxypropyl sulfide bis(2-mercaptoacetate), hydroxypropyl sulfide bis(3-mercaptopropionate), hydroxymethyl disulfide bis(2-mercaptoacetate), hydroxyethyl disulfide bis(3-mercaptopropionate), hydroxyethyl disulfide bis(2-mercaptoacetate), hydroxyethyl disulfide bis(3-mercaptopropionate), hydroxypropyl disulfide bis(2-mercaptoacetate), hydroxypropyl disulfide bis(3-mercaptopropionate), 2-mercaptoethyl ether bis(2-mercaptoacetate), 2-mercaptoethyl ether bis(3-mercaptopropionate), 1,4-dithiane-2,5-diol bis(2-mercaptoacetate), 1,4-dithiane-2,5-diol bis(3-mercaptopropionate), 2,5-bis(mercaptomethyl)-1,4-dithiane,
2,5-bis(2-mercaptoethyl)-1,4-dithiane,
2,5-bis(3-mercaptopropyl)-1,4-dithiane,
2-(2-mercaptoethyl)-5-mercaptomethyl-1,4-dithiane,
2-(2-mercaptoethyl)-5-(3-mercaptopropyl)-1,4-dithiane,
2-mercaptomethyl-5-(3-mercaptopropyl)-1,4-dithiane,
thioglycolic acid bis(2-mercaptoethyl ester), thiodipropionic acid bis(2-mercaptoethyl ester), 4,4'-thiodibutyric acid bis(2-mercaptoethyl ester), dithiodiglycolic acid bis(2-mercaptoethyl ester), dithiodipropionic acid bis(2-mercaptoethyl ester), 4,4'-dithiodibutyric acid bis(2-mercaptoethyl ester), thiodiglycolic acid bis(2,3-dimercaptopropyl ester), thiodipropionic acid bis(2,3-dimercaptopropyl ester), dithiodiglycolic acid bis(2,3-dimercaptopropyl ester) and dithiodipropionic acid (2,3-dimercaptopropyl ester).

Heterocyclic polythiols containing a sulfur atom in addition to a mercapto group include 3,4-thiophenedithiol, tetrahydrothiophene-2,5-dimercaptomethyl and 2,5-dimercapto-1,3,4-thiadiazole Polythiols containing an isocyanurate group include 1,2-bis[(2-mercaptoethyl)thio]3-mercaptopropane,
tris-{(3-mercaptopropionyloxy)-ethyl}-isocyanurate,
1,3,5-tris(3-mercaptobutyryloxyethyl)-1,3,5-triazine-2,4,6 (1H,3H,5H)-trione and
tris-[(3-mercaptopropionyloxy)-ethyl]-isocyanurate.

(B3-3) Polyamine

The polyamine is a compound having at least two NH$_2$ groups in one molecule, and examples thereof include the following compounds. The compounds include ethylenediamine, hexamethylenediamine, isophoronediamine, nonamethylenediamine, undecanemethylenediamine, dodecamethylenediamine, metaxylenediamine, 1,3-propanediamine, putrescine, 2-(2-aminoethylamino)ethanol, diethylenetriamine, p-phenylenediamine, m-phenylenediamine, melamine and 1,3,5-benzenetriamine.

(B3-4) Polyisocyanate

The polyisocyanate is a compound having at least two NCO groups in one molecule, and examples thereof include the following compounds.

Aliphatic isocyanates include ethylene diisocyanate, trimethylene diisocyanate, tetramethylene diisocyanate, hexamethylene diisocyanate, octamethylene diisocyanate, nanomethylene diisocyanate, 2,2'-dimethylpentane diisocyanate, 2,2,4-trimethylhexamethylene diisocyanate, decamethylene diisocyanate, butene diisocyanate, 1,3-butadiene-1,4-diisocyanate, 2,4,4-trimethylhexamethylene diisocyanate, 1,6,11-undecatriisocyanate, 1,3,6-hexamethylene triisocyanate, 1,8-diisocyanato-4-isocyanatomethyloctane, 2,5,7-trimethyl-1,8-diisocyanato-5-isocyanatomethyloctane, bis(isocyanatoethyl)carbonate, bis(isocyanatoethyl)ether, 1,4-butylene glycol dipropyl ether-ω,ω'-diisocyanate, lysine diisocyanatomethyl ester, lysine triisocyanate, 2-isocyanatoethyl-2,6-diisocyanatohexanoate and 2-isocyanatopropyl-2,6-diisocyanatohexanoate.

Alicyclic isocyanates include isophorone diisocyanate, norbornane diisocyanate, bis(isocyanatomethyl)cyclohexane, dicyclohexylmethane diisocyanate, cyclohexane diisocyanate, methylcyclohexane diisocyanate, dicyclohexyldimethylmethane diisocyanate, 2,2'-dimethyldicyclohexylmethane diisocyanate,
bis(4-isocyanato-n-butylidene)pentaerythritol, dimeric acid diisocyanate,
2-isocyanatomethyl-3-(3-isocyanatopropyl)-5-isocyanatomethyl-bicyclo[2,2,1]-heptane,
2-isocyanatomethyl-3-(3-isocyanatopropyl)-6-isocyanatomethyl-bicyclo[2,2,1]-heptane,
2-isocyanatomethyl-2-(3-isocyanatopropyl)-5-isocyanatomethyl-bicyclo[2,2,1]-heptane,
2-isocyanatomethyl-2-(3-isocyanatopropyl)-6-isocyanatomethyl-bicyclo[2,2,1]heptane,
2-isocyanatomethyl-3-(3-isocyanatopropyl)-6-(2-isocyanatoethyl)-bicyclo[2,2,1]-heptane,
2-isocyanatomethyl-3-(3-isocyanatopropyl)-6-(2-isocyanatoethyl)-bicyclo[2,1,1]-heptane,
2-isocyanatomethyl-2-(3-isocyanatopropyl)-5-(2-isocyanatoethyl)-bicyclo[2,2,1]-heptane,
2-isocyanatomethyl-2-(3-isocyanatopropyl)-6-(2-isocyanatoethyl)-bicyclo[2,2,1]-heptane and
1,3,5-tris(isocyanatomethyl)cyclohexane.

Aromatic isocyanates include xylylene diisocyanate, bis(isocyanatoethyl)benzene, bis(isocyanatopropyl)benzene, α,α,α',α'-tetramethylxylylene diisocyanate, bis(isocyanatobutyl)benzene, bis(isocyanatomethyl)naphthalene, bis(isocyanatomethyl)diphenyl ether, bis(isocyanatoethyl)phthalate, mesitylene triisocyanate, 2,6-di(isocyanatomethyl) furan, phenylene diisocyanate, tolylene diisocyanate, ethyl phenylene diisocyanate, isopropyl phenylene diisocyanate, dimethyl phenylene diisocyanate, diethyl phenylene diisocyanate, diisopropyl phenylene diisocyanate, trimethylbenzene triisocyanate, benzene triisocyanate, naphthalene diisocyanate, methyl naphthalene diisocyanate, biphenyl diisocyanate, tolidine diisocyanate, 4,4'-diphenylmethane diisocyanate, 3,3'-dimethyldiphenylmethane-4,4'-diisocyanate, bibenzyl-4,4'-diisocyanate, bis(isocyanatophenyl)ethylene, 3,3'-dimethoxybiphenyl-4,4'-diisocyanate, triphenylmethane triisocyanate, polymeric MDI, naphthalene triisocyanate, diphenylmethane-2,4,4'-triisocyanate, 3-methyldiphenylmethane-4,6,4'-triisocyanate, 4-methyl-diphenylmethane-3,5,2',4',6'-pentaisocyanate, phenyl isocyanatomethyl isocyanate, phenyl isocyanatoethyl isocyanate, tetrahydronaphthylene diisocyanate, hexahydrobenzene diisocyanate, hexahydrodiphenylmethane-4,4'-diisocyanate, diphenyl ether diisocyanate, ethylene glycol diphenyl ether diisocyanate, 1,3-propylene glycol diphenyl ether diisocyanate, benzophenone diisocyanate, diethylene glycol diphenyl ether diisocyanate, dibenzofuran diisocyanate, carbazole diisocyanate, ethyl carbazole diisocyanate and dichlorocarbazole diisocyanate.

Sulfur-containing aliphatic isocyanates include thiodiethyl diisocyanate, thiodipropyl diisocyanate, thiodihexyl diisocyanate, dimethyl sulfone diisocyanate, dithiodimethyl diisocyanate, dithiodiethyl diisocyanate, dithiodipropyl diisocyanate, dicyclohexylsulfide-4,4'-diisocyanate, 1-isocyanatomethylthia-2,3-bis(2-isocyanatoethylthia)propan e, 1,2-bis(2-isocyanatoethylthio)ethane, 1,1,2,2-tetrakis (isocyanatomethylthio)ethane, 2,2,5,5-tetrakis (isocyanatomethylthio)-1,4-dithiane, 2,4-dithiapentane-1,3-diisocyanate, 2,4,6-trithiaheptane-3,5-diisocyanate, 2,4,7,9-tetrathiapentane-5,6-diisocyanate and bis (isocyanatomethylthio)phenyl methane.

Aliphatic sulfide-based isocyanates include bis[2-(isocyanatomethylthio)ethyl]sulfide.

Aromatic sulfide-based isocyanates include diphenyl sulfide-2,4'-diisocyanate, diphenyl sulfide-4,4'-diisocyanate, 3,3'-dimethoxy-4,4'-diisocyanatodibenzyl thioether, bis(4-isocyanatomethylbenzene)sulfide and 4,4'-methoxybenzenethioethylene glycol-3,3'-diisocyanate.

Aromatic disulfide-based isocyanates include diphenyl disulfide-4,4'-diisocyanate, 2,2'-dimethyl diphenyl disulfide-5,5'-diisocyanate, 3,3'-dimethyl diphenyl disulfide-5,5'-diisocyanate, 3,3'-dimethyl diphenyl disulfide-6,6'-diisocyanate, 4,4'-dimethyl diphenyl disulfide-5,5'-diisocyanate, 3,3'-dimethoxy diphenyl disulfide-4,4'-diisocyanate and 4,4'-dimethoxy diphenyl disulfide-3,3'-diisocyanate.

Aromatic sulfone-based isocyanates include diphenyl sulfone-4,4'-diisocyanate, diphenyl sulfone-3,3'-diisocyanate, benzylidene sulfone-4,4'-diisocyanate, diphenylmethane sulfone-4,4'-diisocyanate, 4-methyldiphenylmethane sulfone-2,4'-diisocyanate, 4,4'-dimethoxydiphenyl sulfone-3,3'-diisocyanate, 3,3'-dimethoxy-4,4'-diisocyanatodibenzyl sulfone, 4,4'-dimethyldiphenyl sulfone-3,3'-diisocyanate, 4,4'-di-tert-butyldiphenyl sulfone-3,3'-diisocyanate, 4,4'-dimethoxybenzene ethylene disulfone-3,3'-diisocyanate and 4,4'-dichlorodiphenyl sulfone-3,3'-diisocyanate.

Sulfonic acid ester-based isocyanates include 4-methyl-3-isocyanatobenzene sulfonyl-4'-isocyanatophenol ester and 4-methoxy-3-isocyanatobenzene sulfonyl-4'-isocyanatophenol ester.

Aromatic sulfonic acid amide-based isocyanates include 4-methyl-3-isocyanatobenzene sulfonylanilide-3'-methyl-4'-isocyanate, dibenzene sulfonyl-ethylenediamine-4,4'-diisocyanate, 4,4'-dimethoxybenzene sulfonyl-ethylenediamine-3,3'-diisocyanate and 4-methyl-3-isocyanatobenzene sulfonylanilide-4-methyl-3'-isocyanate.

Sulfur-containing heterocyclic isocyanates include thiophene-2,5-diisocyanate, thiophene-2,5-diisocyanatomethyl, 1,4-dithiane-2,5-diisocyanate, 1,4-dithiane-2,5-diisocyanatomethyl, 1,3-dithiolane-4,5-diisocyanate, 1,3-dithiolane-4,5-diisocyanatomethyl, 1,3-dithiolane-2-methyl-4,5-diisocyanatomethyl, 1,3-dithiolane-2,2-diisocyanatoethyl, tetrahydrothiophene-2,5-diisocyanate, tetrahydrothiophene-2,5-diisocyanatomethyl, tetrahydrothiophene-2,5-diisocyanatoethyl and tetrahydrothiophene-3,4-diisocyanatomethyl.

Further, halogen substitution products, alkyl substitution products, alkoxy substitution products, nitro substitution products, polyhydric alcohol prepolymer type modified products, carbodiimide modified products, urea modified products, biuret modified products, and dimerization and trimerization reaction products of the above polyisocyanates may also be used.

(B3-5) polyisothiocyanate

The polyisothiocyanate is a compound having at least two NCS groups in one molecule, and examples thereof include the following compounds.

Aliphatic isothiocyanates include 1,2-diisothiocyanatoethane, 1,3-diisothiocyanatopropane, 1,4-diisothiocyanatobutane, 1,6-diisothiocyanatohexane and p-phenylene diisopropylidene diisothiocyanate Alicyclic isothiocyanates include cyclohexyl isothiocyanate and cyclohexane diisothiocyanate.

Aromatic isothiocyanates include phenyl isothiocyanate, 1,2-diisothiocyanatobenzene, 1,3-diisothiocyanatobenzene, 1,4-diisothiocyanatobenzene, 2,4-diisothiocyanatotoluene, 2,5-diisothiocyanato-m-xylene diisocyanate, 4,4'-diisothiocyanato-1,1'-biphenyl, 1,1'-methylenebis(4-isothiocyanatobenzene), 1,1'-methylenebis(4-isothiocyanato2-methylbenzene), 1,1'-methylenebis(4-isothiocyanato3-methylbenzene), 1,1'-(1,2-ethanediyl)bis(4-isothiocyanatobenzene), 4,4'-diisothiocyanatobenzophenone, 4,4'-diisothiocyanato3,3'-dimethyl benzophenone, benzanilide-3,4'-diisothiocyanate, diphenyl ether-4,4'-diisothiocyanate and diphenylamine-4, 4'-diisothiocyanate.

Heterocyclic isothiocyanates include 2,4,6-triisothiocyanato-1,3,5-triazine.

Carbonyl isothiocyanates include hexanedioyl diisothiocyanate, nonanedioyl diisothiocyanate, carbonic diisothiocyanate, 1,3-benzenedicarbonyl diisothiocyanate, 1,4-benzenedicarbonyl diisothiocyanate and (2,2'-bipyridine)-4,4'-dicarbonyl diisothiocyanate.

Further, polyfunctional isothiocyanates having at least one sulfur atom in addition to the sulfur atom of an isothiocyanate group may also be used. Examples of the polyfunctional isothiocyanates include the following compounds.

Sulfur-containing aliphatic isothiocyanates include thiobis(3-isothiocyanatopropane), thiobis(2-isothiocyanatoethane) and dithiobis(2-isothiocyanatoethane).

Sulfur-containing aromatic isothiocyanates include 1-isothiocyanato4-[(2-isothiocyanato)sulfonyl]benzene, thiobis(4-isothiocyanatobenzene), sulfonyl bis(4-isothiocyanatobenzene), sulfinyl bis(4-isothiocyanatobenzene), dithiobis(4-isothiocyanatobenzene), 4-isothiocyanato-1-{(4-isothiocyanatophenyl)sulfonyl}2-met boxy-benzene, 4-methyl-3-isothiocyanatobenzene sulfonyl-4'-isothiocyanatophenyl ester and 4-methyl-5-isothiocyanatobenzene sulfonylanilide-3'-methyl-4'-isothiocyanate.

Sulfur-containing heterocyclic isothiocyanates include thiophene-2,5-diisothiocyanate and 1,4-dithiane-2,5-diisothiocyanate.

The above urethane-based polymerizable compounds (B3) may be used in combination to forma urethane bond or urea bond by polymerization.

<Other Polymerizable Compounds>

In the present invention, besides the above-described polymerizable compounds (B1) to (B3), an episulfide-based polymerizable compound (B4-1) and a thietanyl-based polymerizable compound (B4-2) may be used as the other polymerizable compounds (B4) to improve refractive index and also a monofunctional polymerizable compound (B4-3) (excluding the above polymerizable compounds having one polymerizable group) may be used to improve photochromic properties. Further, a composite type polymerizable compound (B4-4) having different types of polymerizable groups in the molecule may also be used.

(B4-1) Episulfide-Based Polymerizable Compound;

This polymerizable monomer is a compound having at least two episulfide groups in the molecule and examples thereof include the following compounds.

Bis(1,2-epithioethyl) sulfide,
bis(1,2-epithioethyl)disulfide,
bis(2,3-epithiopropyl) sulfide,
bis(2,3-epithiopropylthio)methane,
bis(2,3-epithiopropyl)disulfide,
bis(2,3-epithiopropyldithio)methane,
bis(2,3-epithiopropyldithio) ethane,
bis(6,7-epithio-3,4-dithiaheptyl) sulfide,
bis(6,7-epithio-3,4-dithiaheptyl)disulfide,
1,4-dithiane-2,5-bis(2,3-epithiopropyldithiomethyl),
1,3-bis(2,3-epithiopropyldithiomethyl)benzene,
1,6-bis(2,3-epithiopropyldithiomethyl)-2-(2,3-epithiopropyl dithioethylthio)-4-thiahexane,
1,2,3-tris(2,3-epithiopropyldithio)propane,
1,1,1,1-tetrakis(2,3-epithiopropyldithiomethyl)methane, 1,3-bis(2,3-epithiopropyldithio)-2-thiapropane,
1,4-bis(2,3-epithiopropyldithio)-2,3-dithiabutane,
1,1,1-tris(2,3-epithiopropyldithio)methane,
1,1,1-tris(2,3-epithiopropyldithiomethylthio)methane,
1,1,2,2-tetrakis(2,3-epithiopropyldithio)ethane,
1,1,2,2-tetrakis(2,3-epithiopropyldithiomethylthio)ethane,
1,1,3,3-tetrakis(2,3-epithiopropyldithio)propane,
1,1,3,3-tetrakis(2,3-epithiopropyldithiomethylthio)propane,
2-[1,1-bis(2,3-epithiopropyldithio)methyl]-1,3-dithietane and
2-[1,1-bis(2,3-epithiopropyldithiomethylthio)methyl]-1,3-dithietane (B4-2) Thietanyl-Based Polymerizable Compound This polymerizable compound is a thietane compound having at least two thietanyl groups in the molecule. Some of the thietanyl-based polymerizable compounds have an episulfide group together with a plurality of thietanyl groups and are listed in the above paragraph for the episulfide-based polymerizable compound. Other thietanyl-based polymerizable compounds include metal-containing thietane compounds having a metal atom in the molecule and non-metal thietane compounds containing no metal.

The non-metal thietane compounds include
bis(3-thietanyl)disulfide, bis(3-thietanyl)sulfide,
bis(3-thietanyl)trisulfide, bis(3-thietanyl)tetrasulfide,
1,4-bis(3-thietanyl)-1,3,4-trithiabutane,
1,5-bis(3-thietanyl)-1,2,4,5-tetrathiapentane,
1,6-bis(3-thietanyl)-1,3,4,6-tetrathiahexane,
1,6-bis(3-thietanyl)-1,3,5,6-tetrathiahexane,
1,7-bis(3-thietanyl)-1,2,4,5,7-pentathiaheptane,
1,7-bis(3-thietanylthio)-1,2,4,6,7-pentathiaheptane,
1,1-bis(3-thietanylthio)methane,
1,2-bis(3-thietanylthio)ethane,
1,2,3-tris(3-thietanylthio)propane,
1,8-bis(3-thietanylthio)-4-(3-thietanylthiomethyl)-3,6-dithiaoctane,
1,11-bis(3-thietanylthio)-4,8-bis(3-thietanylthiomethyl)-3,6,9-trithiaundecane,
1,11-bis(3-thietanylthio)-4,7-bis(3-thietanylthiomethyl)-3,6,9-trithiaundecane,
1,11-bis(3-thietanylthio)-5,7-bis(3-thietanylthiomethyl)-3,6,9-trithiaundecane,
2,5-bis(3-thietanylthiomethyl)-1,4-dithiane,
2,5-bis[[2-(3-thietanylthio)ethyl]thiomethyl]-1,4-dithiane,
2,5-bis(3-thietanylthiomethyl)-2,5-dimethyl-1,4-dithiane,
bisthietanyl sulfide,
bis(thietanylthio)methane3-[<(thietanylthio)methylthio>methylthio]thietane, bisthietanyl disulfide, bisthietanyl trisulfide, bisthietanyl tetrasulfide, bisthietanyl pentasulfide, 1,4-bis(3-thietanyldithio)-2,3-dithiabutane,
1,1,1-tris(3-thietanyldithio)methane,
1,1,1-tris(3-thietanyldithiomethylthio)methane,
1,1,2,2-tetrakis(3-thietanyldithio)ethane and
1,1,2,2-tetrakis(3-thietanyldithiomethylthio)ethane.

The metal-containing thietane compounds contain the group 14 element such as Sn atom, Si atom, Ge atom or Pb atom; the group 4 element such as Zr atom or Ti atom; the group 13 element such as Al atom; or the group 12 element such as Zn atom as the metal atom in the molecule. The following compounds are particularly preferably used.

Alkylthio(thietanylthio)tin's include methylthiotris(thietanylthio)tin, ethylthiotris(thietanylthio)tin, propylthiotris(thietanylthio)tin and isopropylthiotris(thietanylthio)tin.

Bis(alkylthio)bis(thietanylthio)tin's include bis(methylthio)bis(thietanylthio)tin, bis(ethylthio)bis(thietanylthio)tin, bis(propylthio)bis(thietanylthio)tin and bis(isopropylthio)bis(thietanylthio)tin.

Alkylthio(alkylthio)bis(thietanylthio)tin's include ethylthio(methylthio)bis(thietanylthio)tin, methylthio(propylthio)bis(thietanylthio)tin, isopropylthio(methylthio)bis(thietanylthio)tin, ethylthio(propylthio)bis(thietanylthio)tin, ethylthio(isopropylthio)bis(thietanylthio)tin and isopropylthio(propylthio)bis(thietanylthio)tin.

Bis(thietanylthio) cyclic dithiotin compounds include bis(thietanylthio)dithiastannetane, bis(thietanylthio)dithiastannolane, bis(thietanylthio)dithiastanninane and bis(thietanylthio)trithiastannocane.

Alkyl(thietanylthio)tin compounds include methyltris(thietanylthio)tin, dimethylbis(thietanylthio)tin, butyltris(thietanylthio)tin and tetrakis(thietanylthio)tin.

Compounds containing a metal other than tin include tetrakis(thietanylthio)germanium and tris(thietanylthio)bismuth.

(B4-3) Monofunctional Polymerizable Compound

This polymerizable compound is a compound which has one OH group or SH group in the molecule and used in combination with the above polyol to enhance photochromic properties by adjusting the molecular weight or the cross-linking degree. Examples of the monofunctional polymerizable compound include the following compounds. Polyethylene glycol monooleyl ether, polyethylene glycol monomethyl ether, polyoxyethylene lauryl ether, polyoxyethylene alkyl ether, polyoxyethylene2-ethylhexyl ether, polyoxyethylene tridecyl ether, polyoxyethylene cetyl ether, polyoxyethylene stearyl ether and polyethylene glycol mono-4-octylphenyl ether.

(B4-4) Composite Type Polymerizable Compound

This polymerizable compound has different types of polymerizable groups in the molecule, and various physical properties can be adjusted by using this polymerizable compound.

Examples of this composite type polymerizable compound include the following compounds.

Radical polymerization/OH type polymerizable compounds include 2-hydroxy methacrylate, 2-hydroxy acrylate and 2-hydroxypropyl acrylate.

Radical polymerization/isocyanate type polymerizable compounds include 2-isocyanatoethyl methacrylate and 2-isocyanatoethyl acrylate.

OH/SH type polymerizable compounds include 2-mercaptoethanol, 3-mercapto-1,2-propanediol, glycerin di(mercaptoacetate), 1-hydroxy-4-mercaptocyclohexane, 2,4-dimercaptophenol, 2-mercaptohydroquinone, 4-mercaptophenol, 1,3-dimercapto-2-propanol, 2,3-dimercapto-1-propanol, 1,2-dimercapto-1,3-butanediol, pentaerythritol tris(3-mercaptopropionate), pentaerythritol mono(3-mercaptopropionate), pentaerythritol bis(3-mercaptopropionate), pentaerythritol tris(thioglycolate), pentaerythritol pentakis(3-mercaptopropionate), hydroxymethyl-tris(mercaptoethylthiomethyl)methane,
1-hydroxyethylthio-3-mercaptoethylthiobenzene, 4-hydroxy-4'-mercaptodiphenyl sulfone, 2-(2-mercaptoethylthio)ethanol, dihydroxyethyl sulfide mono(3-mercaptopropionate), dimercaptoethane mono(salicylate) and hydroxyethylthiomethyl-tris(mercaptoethylthio)methane Out of the above polymerizable compounds (B1) to (B4), preferably used polymerizable compounds are radically polymerizable compounds (B1) and urethane-based polymerizable compounds (B3) in the kneading method, radically polymerizable compounds (B1) in the lamination method, and urethane-based polymerizable compounds (B3) in the binder method.

<Polymerization-Curing Accelerator>

Various polymerization-curing accelerators (may be referred to as "component (C)") may be used to accelerate the polymerization and curing of the photochromic composition of the present invention according to the type of the polymerizable functional group of the above polymerizable compound (B).

For example, when a radically polymerizable compound (B1) is used, a polymerization initiator (C1) is used as the polymerization-curing accelerator.

When a curable composition comprising an epoxy-based polymerizable compound (B2), an episulfide-based polymerizable compound (B4-1) and a thietanyl-based polymerizable compound (B4-2) is used, an epoxy curing agent (C2-1) and a cationic polymerization catalyst (C2-2) for the ring-opening polymerization of an epoxy group are used as the polymerization-curing accelerator.

Further, when a urethane-based polymerizable compound (B3) and the other polymerizable compound (B4) are used, a urethane reaction catalyst (C3-1) and a condensation agent (C3-2) are used as the polymerization-curing accelerator.

(C1) Polymerization Initiator

Polymerization initiators are divided into thermopolymerization initiators and photopolymerization initiators, and examples thereof are given below.

As the thermopolymerization initiators, diacyl peroxides include benzoyl peroxide, p-chlorobenzoyl peroxide, decanoyl peroxide, lauroyl peroxide and acetyl peroxide.

Peroxy esters include t-butylperoxy-2-ethyl hexanoate, t-butylperoxy neodecanoate, cumylperoxy neodecanoate and t-butylperoxy benzoate.

Percarbonates include diisopropylperoxy dicarbonate and di-sec-butylperoxy dicarbonate.

Azo compounds include azobisisobutyronitrile and 2,2'-azobis(2,4-dimethylvaleronitrile).

As the photopolymerization initiators, acetophenone-based compounds include 1-phenyl-2-hydroxy-2-methyl-propan-1-one, 1-hydroxycyclohexylphenyl ketone and 1-(4-isopropylphenyl)-2-hydroxy-2-methylpropan-1-one.

α-dicarbonyl-based compounds include 1,2-diphenylethanedione and methylphenyl glycoxylate.

Acylphosphine oxide-based compounds include 2,6-dimethylbenzoyl diphenylphosphine oxide, 2,4,6-trimethylbenzoyl diphenylphosphine oxide, 2,4,6-trimethylbenzoyl diphenylphosphinic acid methyl ester, 2,6-dichlorobenzoyl diphenylphosphine oxide, 2,6-dimethoxybenzoyl diphenylphosphine oxide and phenylbis(2,4,6-trimethylbenzoyl) phosphine oxide.

When a photopolymerization initiator is used, a known polymerization-curing acceleration aid such as tertiary amine may be used in combination.

(C2-1) Epoxy Curing Agent

Amine compounds and salts thereof include 2-methylimidazole, 2-ethyl-4-methylimidazole, 1,8-diaza-bicyclo(5,4,0)-7-undecene, trimethylamine, benzyl dimethylamine, triethylamine, 2,4,6-tris(dimethylaminomethyl)phenol and 2-(dimethylaminomethyl)phenol.

Quaternary ammonium salts include tetramethylammonium chloride, benzyltrimethylammonium bromide and tetrabutylammonium bromide.

Organic phosphine compounds include tetra-n-butylphosphonium benzotriazoleate and tetra-n-butylphosphonium-o,o-diethylphosphorodithioate.

Metal carboxylic acid salts include chromium (III) tricarboxylate and tin octylate.

Acetylacetone chelate compounds include chromium acetylacetonate.

(C2-2) Cationic Polymerization Catalyst

Lewis acid-based catalysts include $BF_3$.amine complex, $PF_5$, $BF_3$, $AsF_5$ and $SbF_5$.

Thermosetting cationic polymerization catalysts include phosphonium salts, quaternary ammonium salts, sulfonium salts, benzylammonium salts, benzylpyridinium salts, benzylsulfonium salts, hydrazinium salts, carboxylic acid esters, sulfonic acid esters and amine imides.

Ultraviolet curable cationic polymerization catalysts include diaryl iodonium hexafluorophosphate and hexafluoroantimonic acid bis(dodecylphenyl)iodonium.

(C3-1) Urethane Reaction Catalyst

This reaction catalyst is used to form a poly(thio)urethane bond by a reaction between a polyiso(thio)cyanate and a polyol or polythiol.

Examples of the reaction catalyst are given below. Triethylenediamine, hexamethylenetetramine, N, N-dimethyloctylamine, N,N,N',N'-tetramethyl-1,6-diaminohexane, 4,4'-trimethylenebis(1-methylpiperidine), 1,8-diazabicyclo-(5,4,0)-7-undecene, dimethyltin dichloride, dimethyltin bis(isooctylthioglycolate), dibutyltin dichloride, dibutyltin dilaurate, dibutyltin maleate, dibutyltin maleate polymer, dibutyltin dilicinolate, dibutyltin bis(dodecylmercaptide), dibutyltin bis(isooctyl thioglycolate), dioctyltin dichloride, dioctyltin maleate, dioctyltin maleate polymer, dioctyltin bis(butyl maleate), dioctyltin dilaurate, dioctyltin dilicinolate, dioctyltin dioleate, dioctyltin di(6-hydroxy)caproate, dioctyltin bis(isooctyl thioglycolate) and didodecyltin dilicinolate. Metal salts such as copper oleate, copper acetylacetonate, iron acetylacetonate, iron naphthenate, iron lactate, iron citrate, iron gluconate, potassium octanoate and 2-ethylhexyl titanate are also included.

(C3-2) Condensation Agent

Inorganic acids include hydrogen chloride, hydrogen bromide, sulfuric acid and phosphoric acid.

Organic acids include p-toluenesulfonic acid and camphorsulfonic acid.

Acidic ion exchange resins include compounds obtained by introducing a sulfonate group into a styrene-divinylbenzene copolymer.

Carbodiimides include dicyclohexyl carbodiimide and 1-ethyl-3-(3-dimethylaminopyrrolyl)-carbodiimide.

<Blending Amount of Polymerization-Curing Accelerator (C)>

The above polymerization-curing accelerators (C) may be used alone or in combination of two or more, and its amount may be so-called "catalytic amount". For example, the amount of the accelerator may be 0.001 to 10 parts by mass, specifically 0.01 to 5 parts by mass based on 100 parts by mass of the polymerizable compound (B).

<Other Compounding Components>

As long as the effect of the present invention is not impaired, the curable composition of the present invention may comprise various compounding agents known per se, for example, stabilizers such as release agent, ultraviolet absorbent, infrared absorbent, ultraviolet stabilizer, antioxidant, coloring inhibitor, antistatic agent, fluorescent dye, dye, pigment and flavoring agent, additives, solvent, leveling agent and polymerization control agent such as a thiol exemplified by t-dodecyl mercaptan as required.

Especially when an ultraviolet stabilizer is used, it can improve the durability of the photochromic moiety advantageously. As the ultraviolet stabilizer, there are known hindered amine optical stabilizers, hindered phenol antioxidants and sulfur-based antioxidants. Particularly preferred ultraviolet stabilizers are given below. Bis(1,2,2,6,6-pentamethyl-4-piperidyl)sebacate, ADK STAB LA-52, LA-57, LA-62, LA-63, LA-67, LA-77, LA-82 and LA-87 of ADEKA Corporation, 2,6-di-tert-butyl-4-methyl-phenol, ethylenebis(oxyethylene)bis[3-(5-tert-butyl-4-hydroxy-m-tolyl)propionate], and IRGANOX 1010, 1035, 1075, 1098, 1135, 1141, 1222, 1330, 1425, 1520, 259, 3114, 3790, 5057 and 565 of CIBA SPECIALTY CHEMICALS INC.

The ultraviolet stabilizer is preferably used in an amount of 0.001 to 10 parts by mass based on 100 parts by mass of the total of the polymerizable monomers including the chromene compound of the present invention (the total of the chromene compound and the other polymerizable monomer).

<Method of Using Photochromic Curable Composition; Optical Article>

In the present invention, the polymerizable compounds used in the photochromic curable composition are as listed above and the amounts of the other polymerizable compounds may be suitably determined according to intended use. The preferred amount of the chromene compound or the photochromic composition is as described above.

In the present invention, the photochromic curable composition can be prepared by mixing together a chromene compound in use (photochromic composition), polymerizable compounds and optional additives. Polymerization and curing for manufacturing a photochromic cured body are performed by carrying out radical polymerization, ring-opening polymerization, anionic polymerization or condensation polymerization by applying an active energy ray such as ultraviolet ray, α-ray, β-ray or γ-ray, heating or using both of them. That is, suitable polymerization means should be employed according to the types of the polymerizable compounds (B) and the polymerization-curing accelerator (C) and the shape of a photochromic cured body to be formed.

To thermally polymerize the curable composition of the present invention comprising the polymerizable compounds (B), temperature in particular affects the properties of the obtained photochromic cured body. Since this temperature condition is affected by the type and amount of the thermopolymerization initiator and the types of the polymerizable compounds, it cannot be specified unconditionally. In general, a process in which polymerization is started at a relatively low temperature and then the temperature is raised slowly is preferred. Since the polymerization time differs according to various factors like temperature, the optimum time is preferably determined in advance according to these conditions. In general, it is preferred to choose conditions under which polymerization is completed in 2 to 48 hours. To obtain a photochromic laminated sheet, it is preferred that polymerization should be carried out at a temperature at which a reaction between polymerizable functional groups proceeds and that the optimum temperature and the optimum time for obtaining a target molecular weight should be determined at that time.

To optically polymerize the curable composition of the present invention, out of polymerization conditions, UV intensity in particular affects the properties of the obtained photochromic cured body. Since this illuminance condition is affected by the type and amount of the photopolymerization initiator and the types of the polymerizable monomers, it cannot be specified unconditionally. In general, it is preferred to elect condition to ensure that 50 to 500 mW/cm$^2$ UV light having a wavelength of 365 nm should be applied for 0.5 to 5 minutes.

The chromene compound of the present invention can be used as a photochromic material in a wide variety of fields, for example, various recording materials such as recording materials substituting silver-salt photosensitive materials, copying materials, photosensitive materials for printing, recording materials for cathode-ray tubes, laser photosensitive materials and photosensitive materials for holography. The photochromic material comprising the chromene compound of the present invention may be used as a photochromic lens material, optical filter material, display material and material for actonometers and decoration.

For example, to manufacture a photochromic lens by using the chromene compound of the present invention making use of the above polymerization and curing, any known method may be employed if uniform light control performance is obtained.

To develop photochromic properties by the kneading method, the above curable composition is injected into a space formed by a glass mold held by an elastomer gasket or a spacer and cast polymerized by heating in an air furnace or applying an active energy ray such as ultraviolet ray according to the types of the polymerizable compounds (B) and the polymerization-curing accelerator, thereby making it possible to obtain a photochromic cured body which has been molded into an optical material such as a lens.

To develop photochromic properties by the lamination method, a coating solution is prepared by dissolving the curable composition in a suitable organic solvent, applied to the surface of an optical substrate such as a lens substrate by spin coating or dipping and dried to remove the organic solvent, and then polymerization and curing are carried out by UV irradiation or heating in an inert gas such as nitrogen, thereby forming a photochromic layer composed of a photochromic cured body on the surface of the optical substrate (coating method).

The photochromic layer composed of a photochromic cured body can also be formed on the surface of an optical substrate such as a lens substrate by inner-mold cast polymerization in which the optical substrate is arranged opposed to a glass mold in such a manner that a predetermined space is formed therebetween and the curable composition is injected into the space to carry out polymerization-curing by UV irradiation or heating in this state (cast polymerization method).

When the photochromic layer is to be formed on the surface of the optical substrate by the above lamination method (coating method and cast polymerization method), adhesion between the photochromic layer and the optical substrate can be enhanced by subjecting the surface of the optical substrate to a chemical treatment with an alkaline solution or acidic solution, or a physical treatment by corona discharge, plasma discharge or polishing in advance. As a matter of course, a transparent adhesive resin layer may be formed on the surface of the optical substrate.

Further, to develop photochromic properties by the binder method, sheet molding is carried out by using the curable composition to form a photochromic sheet which is then sandwiched between two transparent sheets (optical sheets) and subjected to the above-described polymerization-curing, thereby obtaining a photochromic laminate including a photochromic layer as an adhesive layer.

In this case, the photochromic sheet can also be formed by such means as the coating of a coating solution prepared by dissolving the curable composition in an organic solvent.

The photochromic laminate manufactured as described above is, for example, set in a mold and then a thermoplastic resin (such as polycarbonate) for an optical substrate such as a lens is injection molded to obtain an optical substrate such as a lens having a predetermined shape and provided with photochromic properties. This photochromic laminate may also be bonded to the surface of an optical substrate by an adhesive, thereby making it possible to obtain a photochromic lens.

When the photochromic laminate is to be manufactured as described above, it is preferred to prepare to ensure that a urethane- or urea-based polymerizable compound (B3), especially a urethane-based polymerizable compound should be used as the polymerizable compound (B) to form polyurethane as it has high adhesion to an optical substrate.

The above-described curable composition of the present invention can develop excellent photochromic properties such as color optical density and fading speed and is effectively used in the manufacture of an optical substrate provided with photochromic properties, for example, a photochromic lens, without reducing characteristic properties such as mechanical strength.

According to use purpose, the photochromic layer and the photochromic cured body formed from the curable composition of the present invention may be subjected to a post-treatment such as dying with a dye such as a dispersion dye, the formation of a hard coat film by using a silane coupling agent or a hard coating agent comprising sol of silicon, zirconium, antimony, aluminum, tin or tungsten as the main component, the formation of a thin film by the vapor deposition of a metal oxide such as $SiO_2$, $TiO_2$ or $ZrO_2$, an antireflection treatment with a thin film formed by applying an organic polymer, or an antistatic treatment.

<Hardness of Polymer Molded Body (Cured Body)>

The hardness of a polymer molded body (cured body) containing the chromene compound of the present invention dispersed therein is not particularly limited. The chromene compound of the present invention exhibits an excellent effect in a polymer molded body (cured body) having high hardness since it has low environmental dependence.

In general, since a polymer molded body having high hardness has high crystallinity or is highly crosslinked, the molecular mobility of a chromene compound is low in this polymer molded body. The chromene compound of the present invention exhibits excellent molecular mobility even in a polymer molded matrix. Therefore, the chromene compound of the present invention exhibits excellent photochromic properties even in a polymer molded body in which photochromic properties are hardly developed in the prior art.

The hardness, specifically, L-scale Rockwell hardness of the polymer molded body (cured body) in which the chromene compound of the present invention exhibits an effect is 50 or more, preferably 70 or more, more preferably 90 or more.

EXAMPLES

The following examples and comparative examples are provided for the purpose of further illustrating the present invention but are in no way to be taken as limiting. A description is first given of measuring instruments used in the present invention and the method of producing each component.

Examples 1 to 3 (Synthesis of Chromene Compound of the Present Invention)

Example 1

First Step 75 g (0.100 mol) of polyethylene glycol monoethyl ether having a number average molecular weight of 750, 19.1 g (0.100 mol) of toluene sulfonyl chloride and 11 g (0.110 mol) of triethylamine were dissolved in 150 ml of chloroform and heated at a reflux temperature. After the end of a reaction, the reaction solution was added to iced water, liquid separation was carried out, and the solvent was distilled off to obtain an oily compound represented by the following formula (22).

[CF 29]

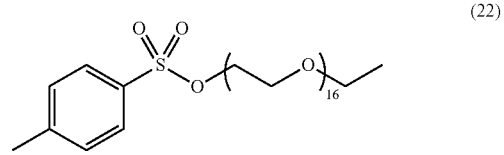

(22)

Second Step 18.1 (0.020 mol) of the product of the above formula (22) obtained in the first step, 3.8 g (0.016 mol) of 4-hydroxy-4'-methoxybenzophenone and 5.5 g (0.040 mol) of potassium carbonate were added to 40 ml of dimethyl formamide and heated at 80° C. After the end of a reaction, the reaction solution was added to iced water, liquid separation was carried out with a mixed solvent of toluene and dimethoxy-ethane, and the solvent was distilled off to obtain a product represented by the following formula (23).

[CF 30]

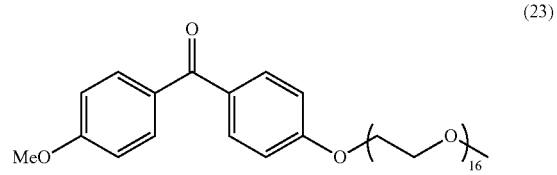

(23)

Third Step 9.6 g (0.010 mol) of the product of the above formula (23) obtained in the second step was dissolved in 40 ml of dimethyl formamide, and the resulting solution was cooled with ice. 1.38 g (0.020 mol) of a lithium acetylide ethylene diamine complex was added and heated up to room temperature slowly. After the end of a reaction, the reaction solution was added to iced water, a mixed solvent of toluene and dimethoxyethane was added, liquid separation was carried out, and the solvent was distilled off to obtain a product represented by the following formula (24).

[CF 31]

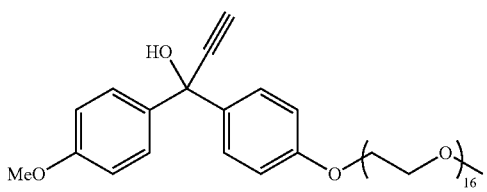

(24)

Fourth Step 2.1 g (0.005 mol) of a naphthol compound represented by the following formula (25)

[CF 32]

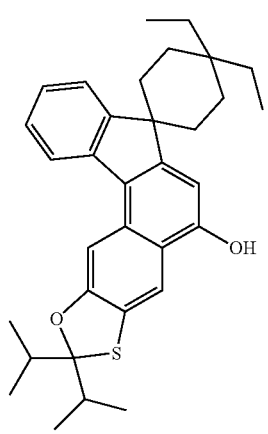

(25)

and 5.9 g (0.006 mol) of the product of the above formula (24) obtained in the third step were dissolved in 15 ml of a mixed solvent of methyl isobutyl ketone and toluene, and a catalytic amount of p-toluenesulfonic acid was further added to the resulting solution to be refluxed under heating. After the end of a reaction, the solvent was removed, and the reaction product was purified by chromatography on silica gel to obtain a chromene compound represented by the following formula (26).

[CF 33]

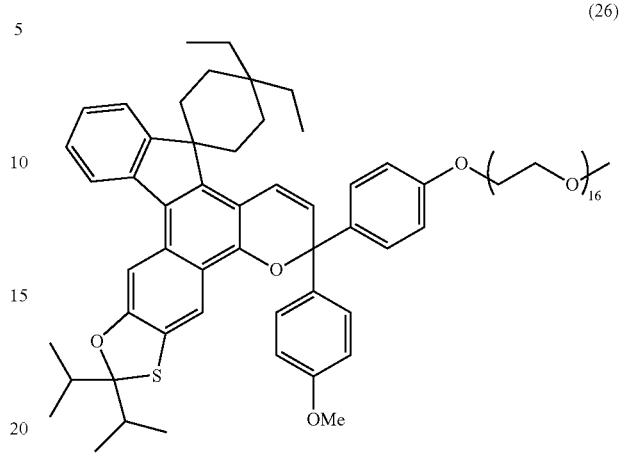

(26)

The yield was 70%.

When the proton nuclear magnetic resonance spectrum was measured, 32H peaks based on the methylene proton of a cyclohexane ring, ethyl group and isopropyl group appeared at around 1.0 to 3.0 ppm, about 70H peaks based on methoxy group and ethoxy group appeared at a δ of around 3.0 to 5.5 ppm, and 16H peaks based on an aromatic proton and an alkene proton appeared at a δ of around 5.6 to 9.0 ppm. It was confirmed that this structure matched the above formula (26).

Example 2

First Step

A product represented by the following formula (27) was obtained in the same manner as in Example 1 except that 4-fluoro-4'-hydroxybenzophenone was used in place of 4-hydroxy-4'-methoxybenzophenone in the first step of Example 1.

[CF 34]

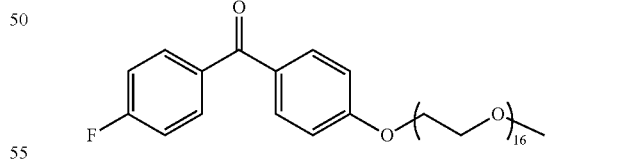

(27)

Second Step 9.5 g (0.010 mol) of the product of the above formula (27) obtained in the first step was dissolved in 20 ml of dimethyl sulfoxide, and 5.0 g of morpholine was added to the resulting solution and heated at 100° C. After the end of a reaction, the reaction solution was added to iced water, a mixed solvent of toluene and dimethoxyethane was added, liquid separation was carried out, and the solvent was distilled off to obtain a product represented by the following formula (28).

[CF 35]

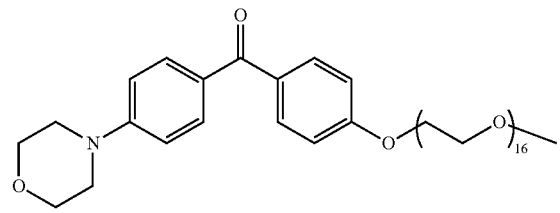

(28)

Third Step

A product represented by the following formula (29) was obtained in the same manner as in Example 1 except that the product represented by the above formula (28) was used in place of the product of the above formula (23) in the third step of Example 1.

[CF 36]

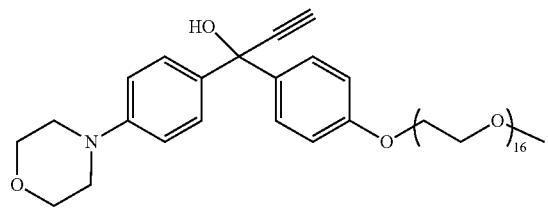

(29)

Fourth Step

A chromene compound represented by the following formula (31) was obtained in the same manner as in the fourth step of Example 1 except that a naphthol compound represented by the following formula (30) and the product of the above formula (29) obtained in the third step were used.

[CF 37]

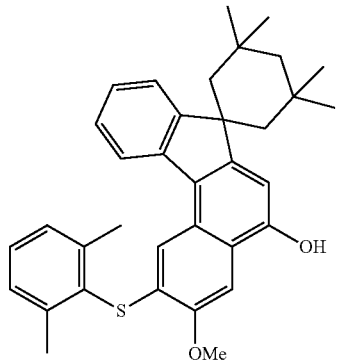

(30)

[CF 38]

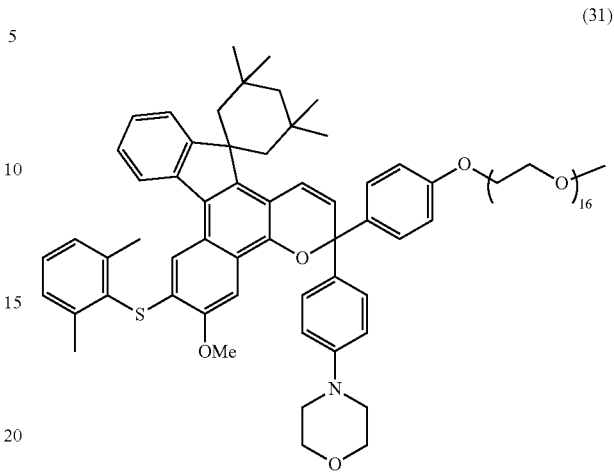

(31)

The yield was 72%.

When the proton nuclear magnetic resonance spectrum was measured, 24H peaks based on the methylene proton of a cyclohexane ring, methyl group and the proton of methyl group appeared at around 1.0 to 3.0 ppm, about 78H peaks based on methoxy group, ethyleneoxy group and morpholino group appeared at a δ of around 3.0 to 5.5 ppm, and 19H peaks based on an aromatic proton and an alkene proton appeared at a δ of around 5.6 to 9.0 ppm. It was confirmed that this structure matched the above formula (31).

Example 3

First to Third Steps

A product represented by the following formula (32) was obtained in the same manner as in Example 1 except that polypropylene glycol monobutyl ether having a number average molecular weight of 1,000 was used in place of polyethylene glycol monoethyl ether having a number average molecular weight of 750 in the first step of Example 1.

[CF 39]

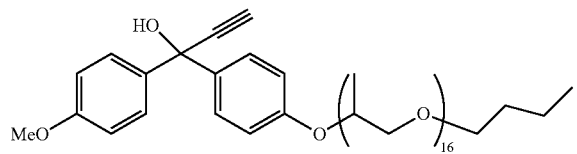

(32)

Fourth Step

A chromene compound represented by the following formula (34) was obtained in the same manner as in the fourth step of Example 1 except that a naphthol compound represented by the following formula (33) and the product represented by the above formula (32) were used.

[CF 40]

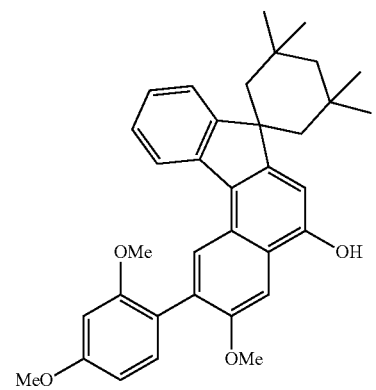

(33)

[CF 41]

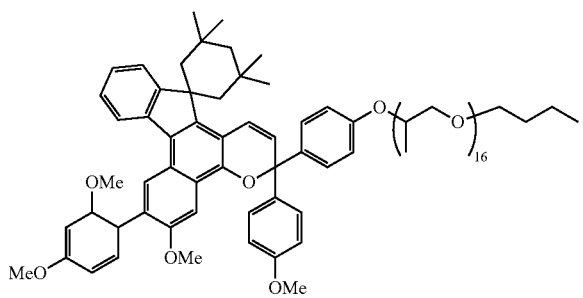

(34)

The yield was 75%.

When the proton nuclear magnetic resonance spectrum was measured, about 73H peaks based on the methylene proton of a cyclohexane ring and the protons of methyl group and butyl group appeared at around 1.0 to 3.0 ppm, about 62H peaks based on methoxy group and propyleneoxy group appeared at a δ of around 3.0 to 5.5 ppm, and 19H peaks based on an aromatic proton and an alkene proton appeared at a δ of around 5.6 to 9.0 ppm. It was confirmed that this structure matched the above formula (34).

Examples 4 to 9 (Manufacture and Evaluation of Photochromic Cured Bodies (Molded Bodies))

The photochromic properties of the above chromene compounds were evaluated as follows in Examples 4 to 9. Components were mixed together according to the following formulations to prepare photochromic curable compositions. The amount of each component is shown below. The compositions in use and the results of photochromic properties are shown in Table 1.

Composition A:
(B) Polymerizable Compounds
Component (B3-2)
26 parts by mass of dipentaerythritol hexakis(3-mercaptopropionate)
Component (B3-4)
30 parts by mass of m-xylylene diisocyanate
Component (B4-3)
44 parts by mass of stearyl-3-mercaptopropionate
(C) Polymerization-Curing Accelerator
0.1 part by mass of dibutyltin dilaurate (catalyst)
(other compounding agent)
0.3 part by mass of di-n-butyltin (release agent)
Composition B:
(B) Polymerizable Compounds
Components (B3-1)
23 parts by mass of DURANOL of Asahi Kasei Chemicals Co., Ltd. (polycarbonate diol, number average molecular weight of 500)
17 parts by mass of trimethylolpropane
Component (B3-4)
54 parts by mass of bicyclo[2.2.1]heptane-2,5(2,6)-diyl) bismethylene diisocyanate
Component (B4-3)
6 parts by mass of polyethylene glycol monooleyl ether (n≈2, Mw=352)
(Other Compounding Agent)
0.3 part by mass of di-n-butyltin (release agent)

In the above compositions, the photochromic curable compositions were added to ensure that the amount of the indenonaphthopyran moiety of the chromene compound became 60 µmol based on 100 g of the total of the polymerizable compounds (B) in the compositions A and B. Photochromic cured bodies (polymer molded bodies) were obtained by using the photochromic curable compositions obtained as described above according to the kneading method. The polymerization method is described below.

(Polymerization Method)

After each of the above photochromic curable compositions was fully defoamed, it was injected into a mold composed of a casting mold including glass molds subjected to a release treatment and a gasket made from an ethylene-vinyl acetate copolymer and having a thickness of 2 mm. Then, the composition was cured over 15 hours while the temperature was gradually raised from 30° C. to 95° C. After the end of polymerization, the photochromic cured body was removed from the glass molds of the casting mold.

(Evaluation Method of Cured Body; Optical Article)

The obtained photochromic cured body was used as a sample and exposed to light having a beam intensity at 365 nm of 2.4 mW/cm$^2$ on the surface of the photochromic cured body and at 245 nm of 24 µW/cm$^2$ with the L-2480 (300 W) SHL-100 xenon lamp of Hamamatsu Photonics K.K. through an aero-mass filter (manufactured by Corning Incorporated) at 20° C.±1° C. for 120 seconds to develop color so as to measure the photochromic properties of the photochromic cured body. The photochromic properties, L-scale Rockwell hardness and cloudiness of the cured body were evaluated by the following methods.

(1) Photochromic Properties

Maximum Absorption Wavelength (λMax):

This is maximum absorption wavelength after color development obtained by the spectrophotometer (instantaneous multi-channel photodetector MCPD1000) of Otsuka Electronics Co., Ltd. The maximum absorption wavelength is connected with color at the time of color development.

Color optical density {ε(120)−ε(0)}:

Difference between absorbance {ε(120)} after 120 seconds of exposure to light at the above maximum absorption wavelength and absorbance ε(0) before exposure. It can be said that as this value becomes larger, photochromic properties become more excellent.

Fading Speed [t½ (Sec.)]:

Time elapsed until the absorbance at the above maximum absorption wavelength of a sample drops to ½ of {ε(120)−ε(0)} when exposure is continued for 120 seconds and then stopped. It can be said that as this time becomes shorter, photochromic properties become more excellent.

Residual Rate ($A_{200}/A_0 \times 100$):

The accelerated deterioration of the obtained photochromic cured body was carried out for 200 hours by means of the X25 xenon weather meter of Suga Test Instruments Co., Ltd. Thereafter, the evaluation of the above color optical density was made before and after the test to measure color optical density ($A_0$) before the test and color optical density ($A_{200}$) after the test so as to calculate the ratio ($A_{200}/A_0$) as the residual rate which is an index of color development durability. It can be said that as the residual rate becomes higher, the color development durability becomes higher.

(2) L-Scale Rockwell Hardness (HL)

After the above cured body (as thick as 2 mm) was kept indoors at 25° C. for one day, the L-scale Rockwell hardness of the photochromic cured body (as thick as 2 mm) was measured by using the Akashi Rockwell hardness meter (model: AR-10).

(3) Cloudiness

The cloudiness of the molded photochromic cured body was visually evaluated under crossed nicols.
1: It has no problem as a product and is not clouded or almost not clouded.
2: It has no problem as a product but is slightly clouded.
3: Although it has no problem as a product, it is more clouded than 2.
4: It is clouded and cannot be used as a product.
The results are shown in Table 1.

TABLE 1

|  | Photochromic curable composition | | Photochromic properties | | | | | |
|---|---|---|---|---|---|---|---|---|
|  |  |  | Maximum absouption wavelength | Optical color density | Fading speed | Residual |  |  |
|  | composition | compound | (nm) | (—) | (sec.) | rate (%) | HL | transparency |
| Example 4 | A | Example 1 | 463 | 0.94 | 64 | 86 | 45 | 1 |
|  |  |  | 573 | 0.68 | 64 | 86 |  |  |
| Example 5 | A | Example 2 | 490 | 0.45 | 28 | 82 | 45 | 1 |
|  |  |  | 605 | 0.52 | 29 | 83 |  |  |
| Example 6 | A | Example 3 | 457 | 0.69 | 53 | 81 | 45 | 1 |
|  |  |  | 582 | 0.68 | 53 | 80 |  |  |
| Example 7 | B | Example 1 | 462 | 0.53 | 91 | 89 | 100 | 1 |
|  |  |  | 568 | 0.38 | 92 | 88 |  |  |
| Example 8 | B | Example 2 | 487 | 0.26 | 40 | 85 | 100 | 1 |
|  |  |  | 595 | 0.30 | 41 | 84 |  |  |
| Example 9 | B | Example 3 | 452 | 0.42 | 80 | 83 | 100 | 1 |
|  |  |  | 574 | 0.42 | 81 | 83 |  |  |

Comparative Examples 1 to 8

For comparison, photochromic cured bodies were obtained in the same manner as in Examples 4 to 9 by using compounds represented by the following formulas (A) to (D), respectively, and the characteristic properties of the photochromic cured bodies were evaluated in the same manner as in Examples 4 to 9. The results are shown in Table 2.

[CF 42]

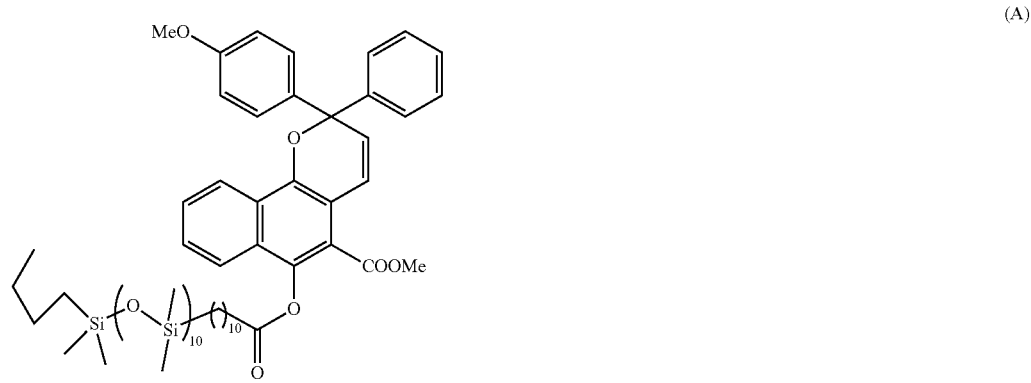

(A)

-continued
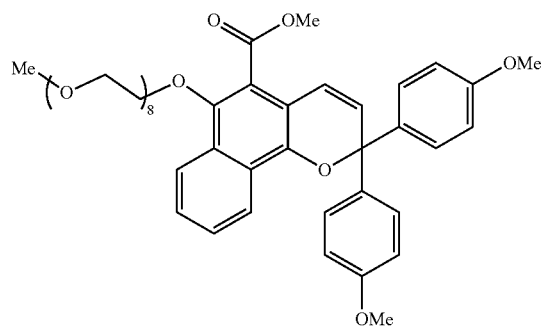
(B)
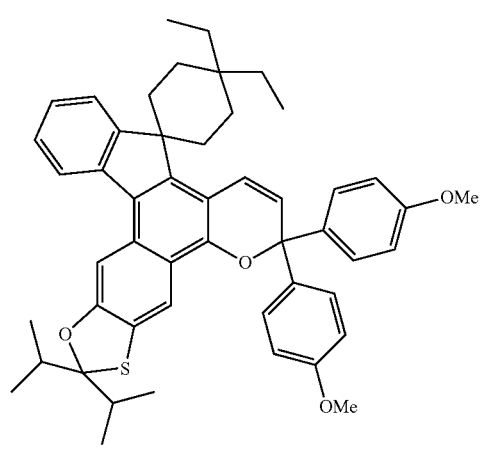
(C)
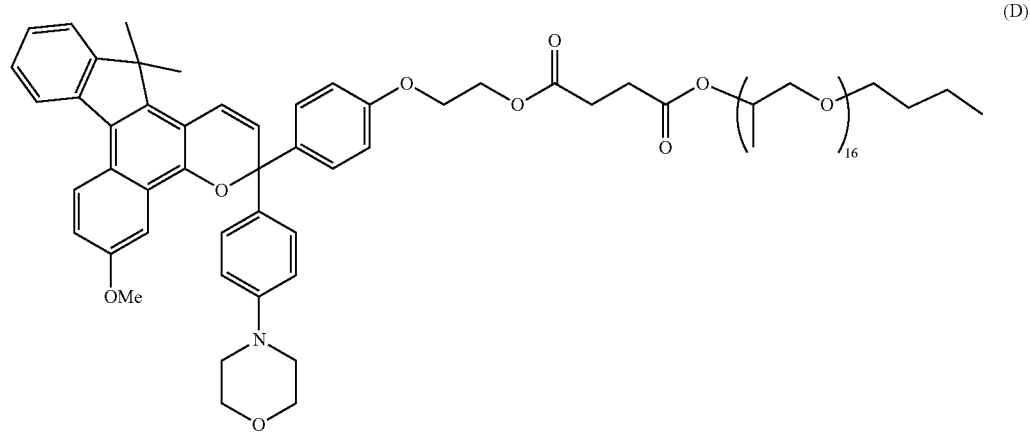
(D)

TABLE 2

|  | Photochromic curable composition | | Photochromic properties | | | | | |
|---|---|---|---|---|---|---|---|---|
|  | composition | compound | Maximum absorption wavelength (nm) | Optical color density (—) | Fading speed (sec.) | Residual speed (%) | HL | transparency |
| Comp. Ex. 1 | A | A | 507 | 0.36 | 72 | 60 | 45 | 1 |
| Comp. Ex. 2 | A | B | 514 | 0.23 | 54 | 62 | 45 | 1 |
| Comp. Ex. 3 | A | C | 465 | 0.90 | 82 | 86 | 45 | 1 |
|  |  |  | 573 | 0.65 | 83 | 86 |  |  |
| Comp. Ex. 4 | A | D | 609 | 1.50 | 97 | 83 | 45 | 1 |
| Comp. Ex. 5 | B | A | 504 | 0.21 | 110 | 65 | 100 | 1 |
| Comp. Ex. 6 | B | B | 511 | 0.13 | 88 | 66 | 100 | 1 |
| Comp. Ex. 7 | B | C | 463 | 0.43 | 152 | 88 | 100 | 1 |
|  |  |  | 567 | 0.31 | 153 | 87 |  |  |
| Comp. Ex. 8 | B | D | 602 | 0.83 | 152 | 85 | 100 | 1 |

Comp. Ex.: Comparative Example

As obvious from Tables 1 and 2, a photochromic cured body obtained by curing the photochromic curable composition of the present invention has excellent photochromic properties and high durability. As compared with the case where a similar chromene compound having no polyalkylene oxide oligomer chain group is blended, the photochromic cured body of the present invention has excellent fading speed even in a matrix having high hardness, thus improving matrix dependence.

Example 10

First Step 100 g (0.100 mol) of polypropylene glimonobutyl ether having a number average molecular weight of 1,000, 20 g (0.200 mol) of succinic anhydride and 2.6 g (0.010 mol) of p-toluenesulfonic acid monohydrate were added and heated at 130° C. for 30 minutes and further at 80° C. for 2.5 hours. After the end of a reaction, the reaction product was dissolved in dichloromethane, and liquid separation was carried out with a 10% hydrochloric acid aqueous solution and then with 20% brine. The obtained organic layer was dried with anhydrous magnesium sulfate. Magnesium sulfate was filtered out and the solvent was distilled off to obtain an oily compound represented by the following formula (35).

[CF 43]

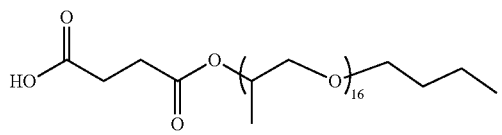

(35)

Second Step

After 21 g (0.020 mol) of the product of the above formula (35) obtained in the first step and a few drops of N,N-dimethylformamide were dissolved in 20 ml of dichloromethane, 10.2 g (0.080 mol) of oxalyl chloride was added to carry out a reaction at room temperature for 1 hour. After the end of the reaction, the solvent was distilled off to obtain an oily compound represented by the following formula (36).

[CF 44]

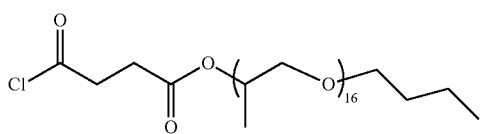

(36)

Third Step 1.0 g (0.003 mol) of a naphthol compound represented by the following formula (37)

[CF 45]

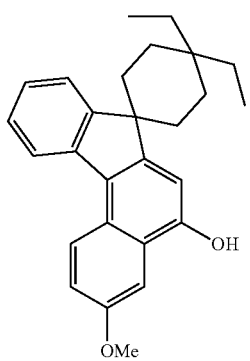

(37)

and 12.0 g (0.003 mol) of a 10 mass % methyl ethyl ketone solution of a propargyl alcohol compound having a reactive substituent (hydroxyl group) and represented by the following formula (38)

[CF 46]

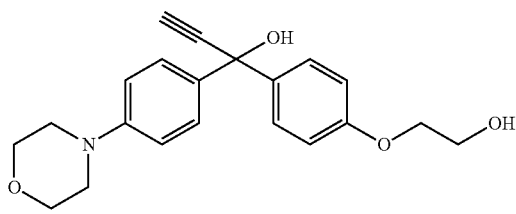
(38)

were dissolved in 50 ml of toluene, and 0.02 g of p-toluenesulfonic acid was further added to the resulting solution, heated and stirred under reflux for 1 hour. After a reaction, the solvent was removed and the obtained product was purified by chromatography on silica gel to obtain a product (precursor) represented by the following formula (39).

[CF 47]

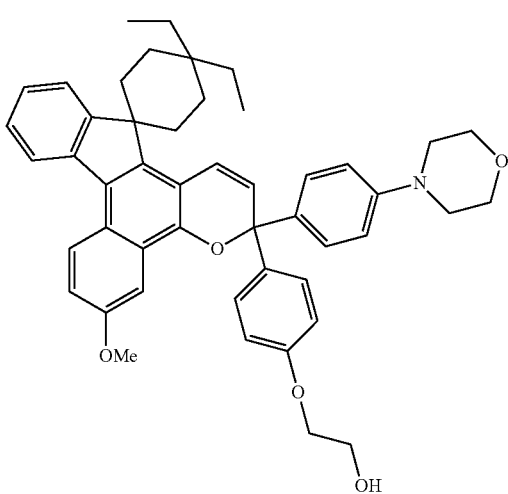
(39)

Fourth Step 1.44 g (0.002 mol) of the product of the above formula (39) obtained in the third step and 0.71 g (0.007 mol) of triethylamine were dissolved in 20 ml of dichloromethane and the resulting solution was cooled with ice. After 2.26 g (0.002 mol) of a dichloromethane solution of the product of the above formula (36) obtained in the second step was added, the resulting solution was heated up to room temperature and then stirred for 1 hour. After the end of a reaction, the solvent was removed and the reaction product was purified by chromatography on silica gel to obtain a chromene compound represented by the following formula (40).

[CF 48]

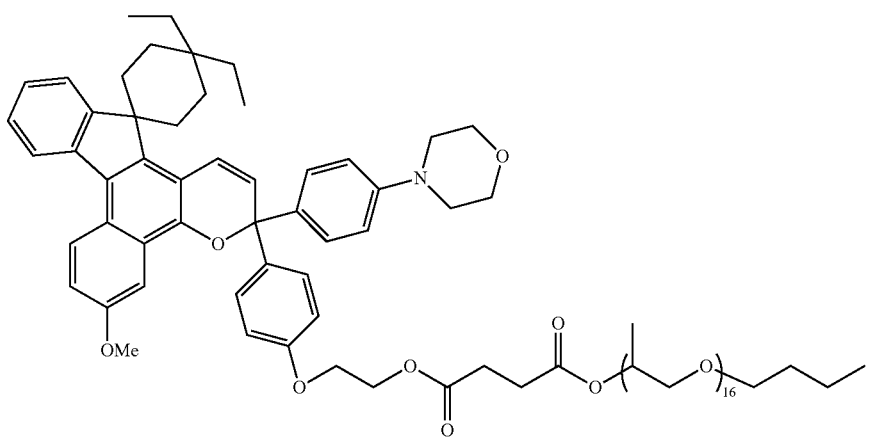
(40)

The yield was 70%. When the proton nuclear magnetic resonance spectrum was measured, about 77H peaks based on the methylene proton of a cyclohexane ring and the protons of methyl group, butyl group, succinic acid moiety and propyleneoxy appeared at around 1.0 to 3.0 ppm, about 65H peaks based on methoxy group, ethylenedioxy group, morpholino group, butyl group and propyleneoxy appeared at a δ of around 3.0 to 5.5 ppm, and 17H peaks based on an aromatic proton and an alkene proton appeared at a δ of around 5.6 to 9.0 ppm. It was confirmed that this structure matched the above formula (40).

Example 11

A chromene compound represented by the following formula (41) was obtained in the same manner as in Example 10 except that polypropylene glycol having a number average molecular weight of 2,000 was used in place of polypropylene glycol monobutyl ether having a number average molecular weight of 1,000 in the first step of Example 10.

[CF 49]

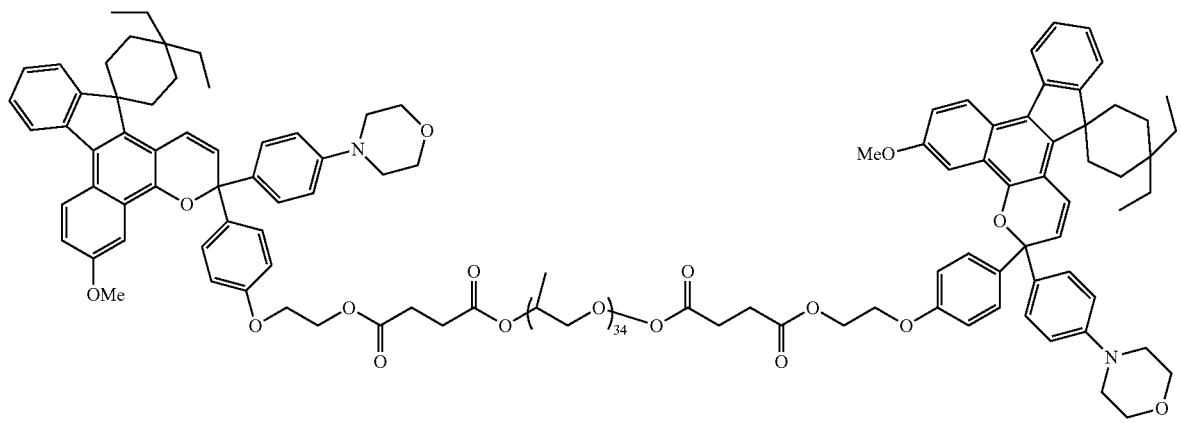

(41)

The yield was 72%. When the proton nuclear magnetic resonance spectrum was measured, about 146H peaks based on the methylene proton of a cyclohexane ring and the protons of methyl group, butyl group, succinic acid moiety and propyleneoxy appeared at around 1.0 to 3.0 ppm, about 132H peaks based on methoxy group, ethylenedioxy group, morpholino group and propyleneoxy appeared at a δ of around 3.0 to 5.5 ppm, and 34H peaks based on an aromatic proton and an alkene proton appeared at a δ of around 5.6 to 9.0 ppm. It was confirmed that this structure matched the above formula (41).

Example 12

First Step

A compound represented by the following formula (42) was obtained in the same manner as in Example 10 except that polyethylene glycol adipate having a number average molecular weight of 2,000 was used in place of polypropylene glycol monobutyl ether having a number average molecular weight of 1,000 in the first step of Example 10.

[CF 50]

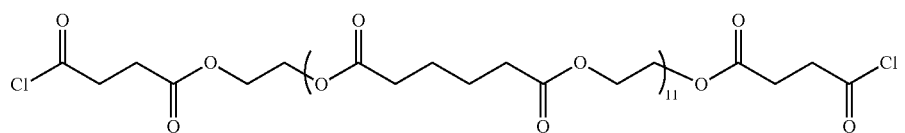

(42)

Second Step

A precursor chromene compound represented by the following formula (44) was obtained in the same manner as in Example 10 except that a naphthol compound represented by the following formula (43) was used in place of the naphthol compound of the above formula (37) in the third step of Example 10.

[CF 53]

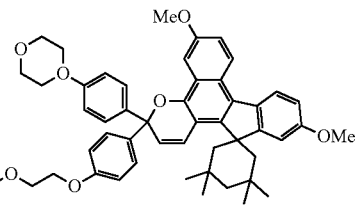

(45)

Third Step

A chromene compound represented by the following formula (45) was obtained in the same manner as in Example 10 except that the compound of the above formula (42) and the compound of the above formula (44) were used in place of the compound of the above formula (36) and the compound of the above formula (39) in the fourth step of Example 10, respectively.

[CF 51]

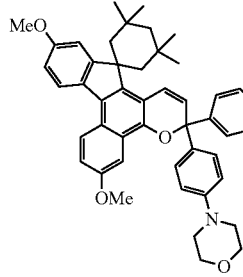

(43)

[CF 52]

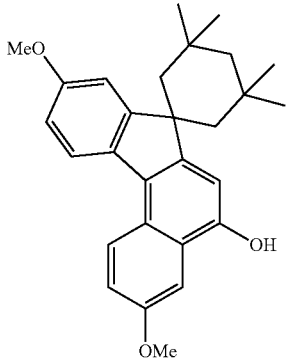

(44)

The yield was 67%. When the proton nuclear magnetic resonance spectrum was measured, about 132H peaks based on the methylene proton of a cyclohexane ring and the protons of methyl group, succinic acid moiety and adipic acid moiety appeared at around 1.0 to 3.0 ppm, about 84H peaks based on methoxy group, ethylenedioxy group, morpholino group and ethyleneoxy appeared at a δ of around 3.0 to 5.5 ppm, and 32H peaks based on an aromatic proton and an alkene proton appeared at a δ of around 5.6 to 9.0 ppm. It was confirmed that this structure matched the above formula (45).

Example 13

First Step

After 9.2 g (0.100 mol) of 1,2,3-propanetriol and 40.8 g (0.600 mol) of imidazole were dissolved in 400 ml of DMF, the resulting solution was cooled with ice. 36.2 g (0.240 mol) of tertiary butyl dimethyl chlorosilane dissolved in 200 ml of DMF was added dropwise to the resulting solution. After the solution was stirred at room temperature for 2 hours, a mixed solvent of 1,2-dimethoxyethane and toluene and brine were added to carryout liquid separation. The obtained organic layer was dried with anhydrous magnesium sulfate. Magnesium sulfate was filtered out and the solvent was distilled off to obtain 1,3-bis(tertiary butyldimethylsiloxy)-2-propanol.

Second Step 14.63 g (0.050 mol) of the product of the first step and 10.00 g (0.100 mol) of succinic anhydride were dissolved in 500 ml of dichloromethane. After the dissolution of these materials was confirmed, 12.65 g (0.130 mol) of triethylamine was added dropwise to the resulting solution to carry out a reaction at room temperature for 12 hours. After the reaction, the reaction solution was cooled with ice, a 1M hydrochloric acid solution, a mixed solvent of 1,2-dimethoxyethane and toluene and brine were added to carry out liquid separation. The obtained organic layer was dried with anhydrous magnesium sulfate. Magnesium sulfate was filtered out and the solvent was distilled off to obtain carboxylic acid represented by the following formula (46).

[CF 54]

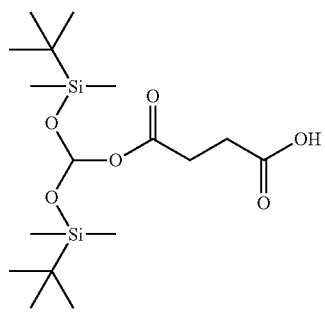

(46)

Third Step 7.85 g (0.020 mol) of the product of the second step and 5 drops of DMF were dissolved in 100 ml of dichloromethane and the resulting solution was cooled with ice. 10.2 g (0.080 mol) of oxalyl chloride was added to carry out a reaction at room temperature for 4 hours. The reaction solution was concentrated to obtain acid chloride represented by the following formula (47).

[CF 55]

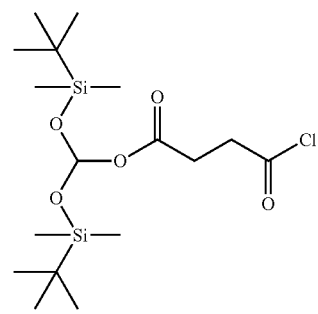

(47)

[CF 56]

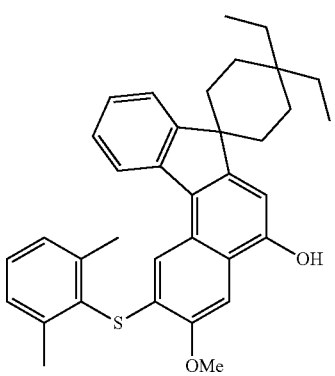

(48)

[CF 57]

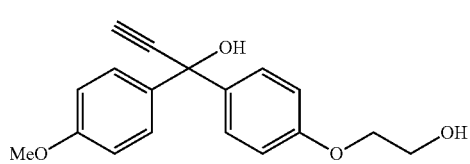

(49)

[CF 58]

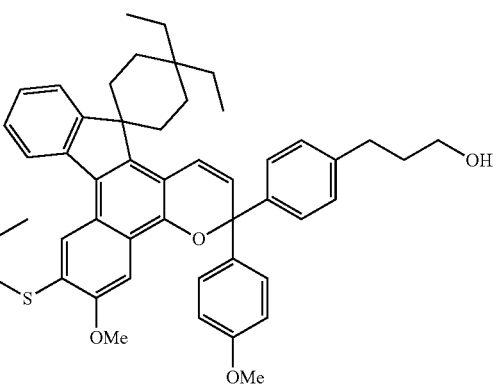

(50)

Fourth Step

A precursor chromene compound represented by the following formula (50) was obtained in the same manner as in Example 10 except that a naphthol compound represented by the following formula (48) was used in place of the naphthol compound of the above formula (37) and a propargyl alcohol represented by the following formula (49) was used in place of the propargyl alcohol of the above formula (38) in Example 10.

Fifth Step

A chromene compound represented by the following formula (51) was obtained by carrying out a reaction in the same manner as in Example 10 except that the precursor chromene compound of the above formula (50) was used in place of the compound of the above formula (39) and the acid chloride of the above formula (47) was used in place of the compound of the above formula (36) in the fourth step of Example 10.

[CF 59]

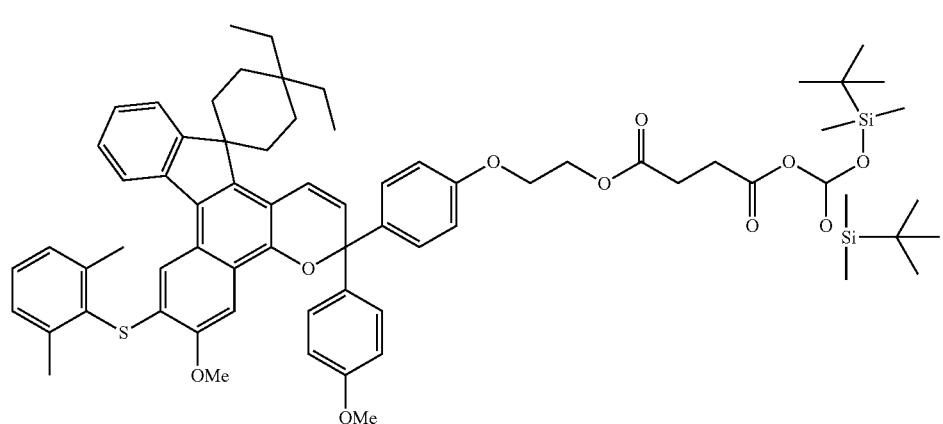

(51)

Sixth Step 5.75 g (0.005 mol) of the chromene compound of the above formula (51) was dissolved in 50 ml of THF and the resulting solution was cooled with ice. 15 ml of a 1 M THF solution of tetrabutylammonium fluoride was added dropwise to the solution over 30 minutes. After addition, the temperature was raised to room temperature slowly to carry out a reaction at room temperature for 2 hours. After the reaction, an organic layer was concentrated, and toluene and brine were added to carry out liquid separation. The obtained organic layer was dried with anhydrous magnesium sulfate. Magnesium sulfate was filtered out and the solvent was distilled off to obtain a chromene compound represented by the following formula (52).

[CF 60]

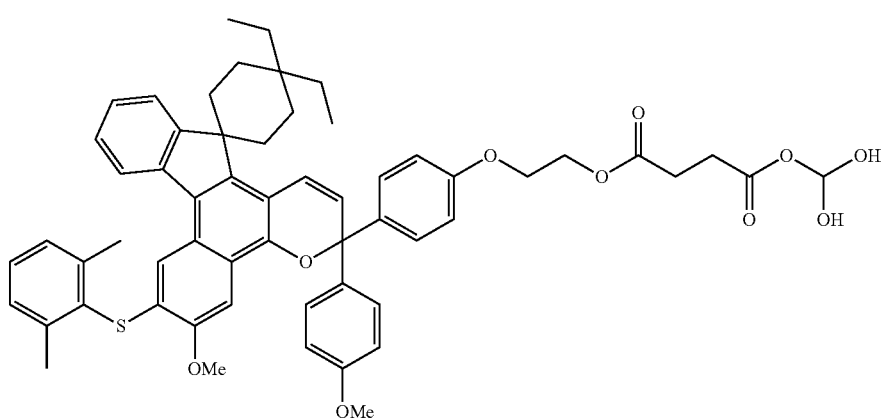

(52)

Seventh Step 4.14 g (0.004 mol) of the chromene compound represented by the above formula (52) and 1.82 g (0.018 mol) of triethylamine were dissolved in 100 ml of dichloromethane and the resulting solution was cooled with ice. Acid chloride represented by the above formula (36) was added dropwise to 10.22 g (0.009 mol) of the dichloromethane solution. After addition, the temperature was raised up to room temperature to carry out a reaction at room temperature for 12 hours. After the end of the reaction, the solvent was removed and the reaction product was purified by chromatography on silica gel to obtain a chromene compound represented by the following formula (53).

[CF 61]

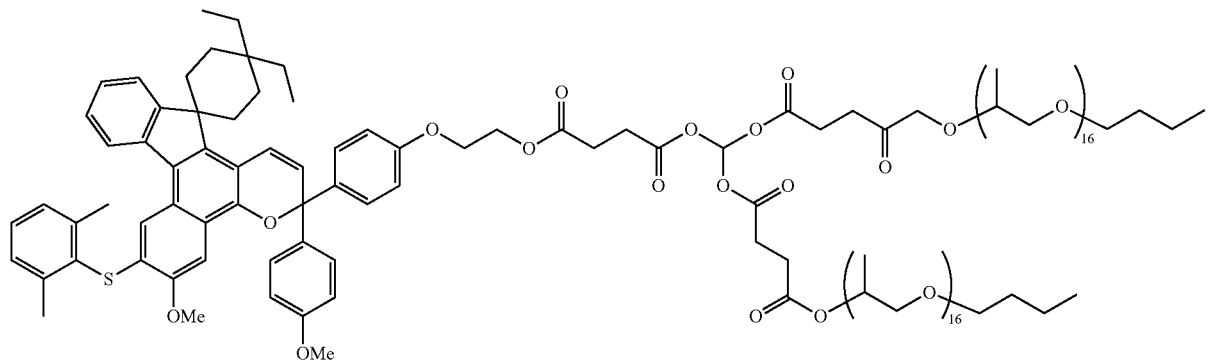

(53)

The yield was 63%.

When the proton nuclear magnetic resonance spectrum was measured, about 146H peaks based on the protons of a cyclohexane ring, methyl group, butoxy group, succinic acid moiety and propyleneoxy appeared at around 1.0 to 3.0 ppm, about 111H peaks based on methoxy group, propyleneoxy group, butoxy group and ethylenedioxy appeared at a δ of around 3.0 to 5.5 ppm, and 19H peaks based on an aromatic proton and an alkene proton appeared at a δ of around 5.6 to 9.0 ppm. It was confirmed that this structure matched the above formula (53).

Example 14

First Step

A chromene compound represented by the following formula (54) was obtained in the same manner as in Example 10 except that the chromene compound represented by the above formula (50) was used in place of the chromene compound represented by the above formula (39) in Example 10.

[CF 62]

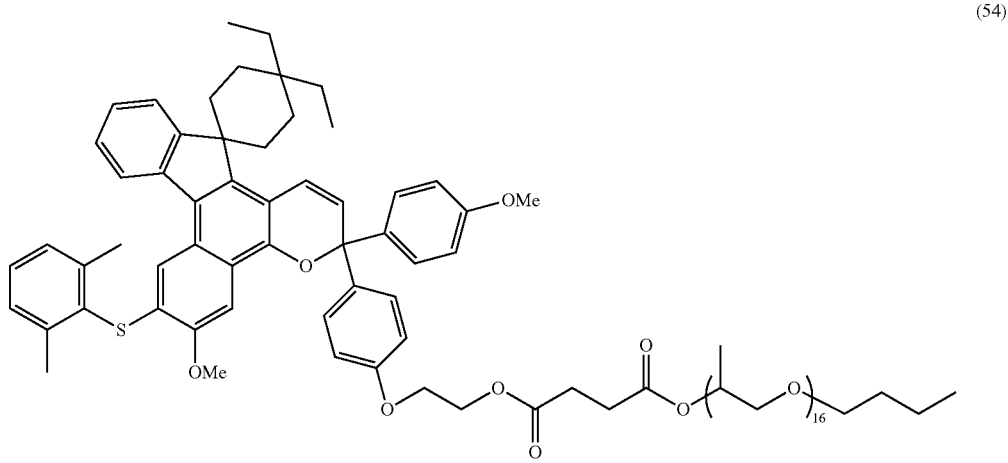

(54)

The yield was 75%.

When the proton nuclear magnetic resonance spectrum was measured, about 83H peaks based on the protons of a cyclohexane ring, methyl group, butoxy group, succinic acid moiety and propyleneoxy appeared at around 1.0 to 3.0 ppm, about 60H peaks based on methoxy group, propyleneoxy group, butoxy group and ethylenedioxy appeared at a δ of around 3.0 to 5.5 ppm, and 19H peaks based on an aromatic proton and an alkene proton appeared at a δ of around 5.6 to 9.0 ppm. It was confirmed that this structure matched the above formula (54).

Example 15

First Step

A chromene compound represented by the following formula (55) was obtained in the same manner as in Example 10 except that polypropylene glimonobutyl ether having a number average molecular weight of 4,100 was used in place of polypropylene glimonobutyl ether having a number average molecular weight of 1,000 in the first step of Example 10.

The yield was 60%.

When the proton nuclear magnetic resonance spectrum was measured, about 245H peaks based on the protons of a cyclohexane ring, methyl group, butoxy group, succinic acid moiety and propyleneoxy appeared at around 1.0 to 3.0 ppm, about 222H peaks based on methoxy group, propyleneoxy group, butoxy group and ethylenedioxy appeared at a δ of around 3.0 to 5.5 ppm, and 19H peaks based on an aromatic proton and an alkene proton appeared at a δ of around 5.6 to 9.0 ppm. It was confirmed that this structure matched the above formula (55).

Example 16

First Step

A chromene compound represented by the following formula (56) was obtained in the same manner as in Example 10 except that polypropylene glimonobutyl ether having a number average molecular weight of 340 was used in place of polypropylene glimonobutyl ether having a number average molecular weight of 1,000 in the first step of Example 10.

[CF 63]

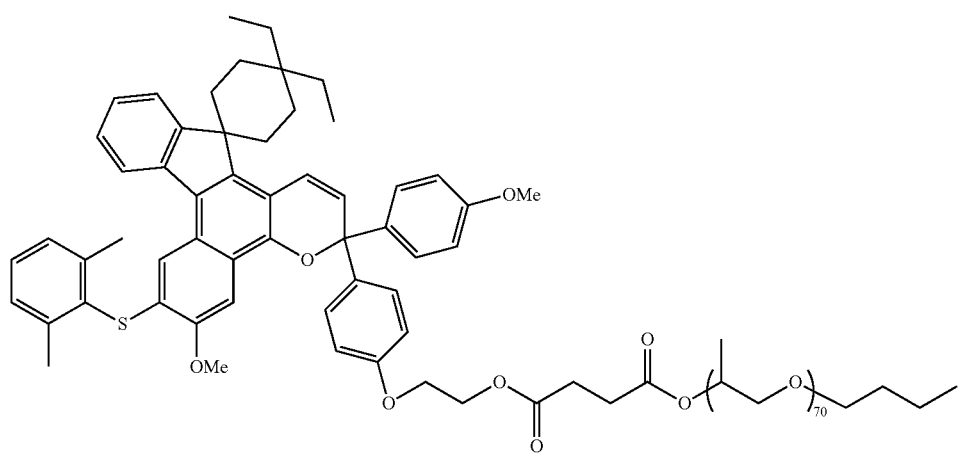

(55)

[CF 64]

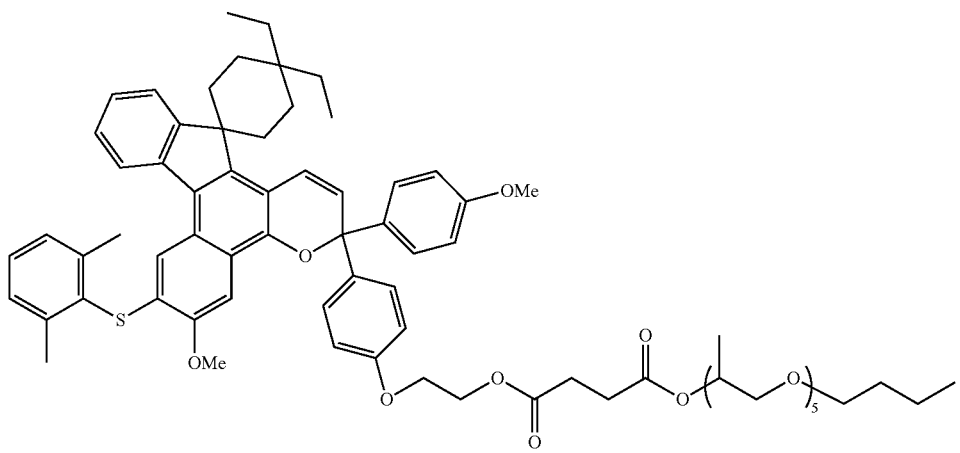

(56)

The yield was 79%.

When the proton nuclear magnetic resonance spectrum was measured, 40H peaks based on the protons of a cyclohexane ring, methyl group, butoxy group, succinic acid moiety and propyleneoxy appeared at around 1.0 to 3.0 ppm, 27H peaks based on methoxy group, propyleneoxy group, butoxy group and ethylenedioxy appeared at a δ of around 3.0 to 5.5 ppm, and 19H peaks based on an aromatic proton and an alkene proton appeared at a δ of around 5.6 to 9.0 ppm. It was confirmed that this structure matched the above formula (56).

Examples 17 to 30, Comparative Examples 9 to 12

Photochromic cured bodies (molded articles) were manufactured and evaluated in the same manner as in Example 4.

The chromene compound was added to ensure that the amount of the indenonaphthopyran moiety became 60 μmol. That is, the chromene compound having two indenonaphthopyran moieties in the compound was added to ensure that the amount of the indenonaphthopyran moiety became 30 μmol.

Compounds represented by the following formulas (E) to (F) were used in Comparative Examples 9 to 12.

[CF 65]

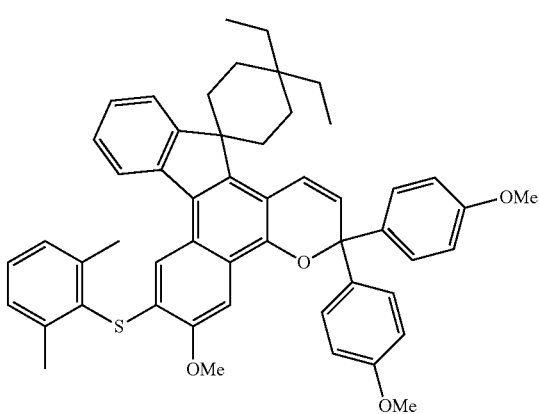

(E)

-continued

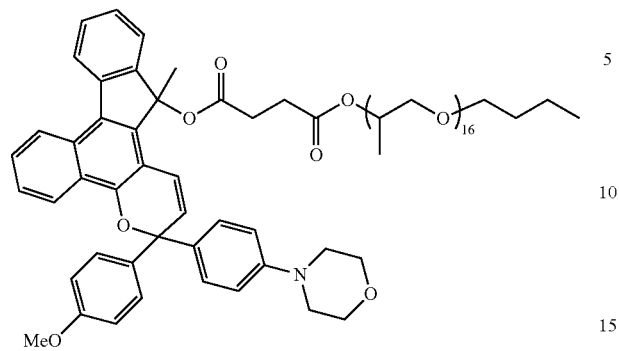
(F)

The blending amount of each component and the results are shown in Table 3.

TABLE 3

| | Photochromic curable composition | | Photochromic properties | | | | | |
|---|---|---|---|---|---|---|---|---|
| | | | Maximum absorption wavelength | Optical color density | Fading speed | Residual rate | | |
| | composition | compound | (nm) | (—) | (sec.) | (%) | HL | transparency |
| Example 17 | A | Example 10 | 598 | 1.43 | 62 | 81 | 45 | 1 |
| Example 18 | A | Example 11 | 597 | 1.48 | 59 | 82 | 45 | 1 |
| Example 19 | A | Example 12 | 609 | 0.94 | 46 | 79 | 45 | 1 |
| Example 20 | A | Example 13 | 468 | 1.02 | 79 | 85 | 45 | 1 |
| | | | 588 | 0.88 | 80 | 85 | | |
| Example 21 | A | Example 14 | 467 | 1.00 | 83 | 85 | 45 | 1 |
| | | | 587 | 0.87 | 83 | 85 | | |
| Example 22 | A | Example 15 | 468 | 1.04 | 77 | 83 | 45 | 1 |
| | | | 586 | 0.92 | 77 | 82 | | |
| Example 23 | A | Example 16 | 468 | 0.97 | 85 | 86 | 45 | 1 |
| | | | 586 | 0.85 | 86 | 86 | | |
| Example 24 | B | Example 10 | 591 | 0.87 | 105 | 82 | 100 | 1 |
| Example 25 | B | Example 11 | 592 | 0.93 | 89 | 83 | 100 | 1 |
| Example 26 | B | Example 12 | 602 | 0.50 | 74 | 80 | 100 | 1 |
| Example 27 | B | Example 13 | 466 | 0.63 | 117 | 87 | 100 | 1 |
| | | | 579 | 0.55 | 118 | 87 | | |
| Example 28 | B | Example 14 | 465 | 0.61 | 127 | 87 | 100 | 1 |
| | | | 582 | 0.54 | 127 | 87 | | |
| Example 29 | B | Example 15 | 466 | 0.74 | 105 | 85 | 100 | 1 |
| | | | 579 | 0.65 | 105 | 84 | | |
| Example 30 | B | Example 16 | 466 | 0.51 | 142 | 87 | 100 | 1 |
| | | | 579 | 0.46 | 143 | 87 | | |
| Comp. Ex. 9 | A | E | 468 | 0.93 | 106 | 87 | 45 | 1 |
| | | | 590 | 0.81 | 107 | | | |
| Comp. Ex. 10 | A | F | 456 | 0.22 | 113 | 57 | 45 | 1 |
| | | | 572 | 0.52 | 113 | | | |
| Comp. Ex. 11 | B | E | 465 | 0.42 | 206 | 88 | 100 | 1 |
| | | | 584 | 0.37 | 207 | | | |
| Comp. Ex. 12 | B | F | 456 | 0.22 | 113 | 57 | 100 | 1 |
| | | | 572 | 0.52 | 113 | | | |

Comp. Ex.: Comparative Example

Examples 31 to 32 and Comparative Example 13

(Evaluation of Physical Properties of Photochromic Plastic Lenses Manufactured by Coating Method)

Photochromic curable compositions were prepared by mixing together components in accordance with the following formulation. The amounts of the compositions are shown below.
Composition C:
(B) Polymerizable Compounds
Component (B1-1-1-1) 10 parts by mass of polyethylene glycol diacrylate (average molecular weight of 532)
Component (B1-1-1-2)
50 parts by mass of
2,2-bis(4-methacryloyloxypentaethoxyphenyl)propane
Component (B1-1-2-1)
10 parts by mass of trimethylolpropane trimethacrylate
Component (B-1-1-2-3)
10 parts by mass of polyester oligomer hexaacrylate (EB-1830 of Daicel U.C.B.)
Component (B1-1-3)
10 parts by mass of glycidyl methacrylate
(C) Polymerization-Curing Accelerator
Component (C-1)
0.3 part by mass of phenylbis(2,4,6-trimethylbenzoyl)phosphine oxide (trade name: Irgacure819, manufactured by BASF)
Other Compounding Components
5 parts by mass of bis(1,2,8,6,6-pentamethyl-4-piperidyl) sebacate 3 parts by mass of ethylenebis(oxyethylene)bis[3-(5-tert-butyl-4-hydroxy-m-tolyl)propionate]
7 parts by mass of 7-methacryloyloxypropyl trimethoxysilane 3 parts by mass of N-methyldiethanolamine Each of the photochromic curable compositions was added to ensure that the amount of the indenonaphthopyran moiety of the chromene compound became 1.2 mmol based on 100 g of the total of the polymerizable compounds (B) in the above composition C. A photochromic laminate was obtained by using the obtained photochromic curable composition in accordance with the coating method. The polymerization method is described below.

A thiourethane-based plastic lens having a center thickness of 2 mm and a refractive index of 1.60 was first prepared as an optical substrate. This thiourethane-based plastic lens was subjected to 5 minutes of alkali etching at 50° C. by using a 10% sodium hydroxide aqueous solution and then fully rinsed with distilled water in advance.

A moisture-curable primer (product name; TR-SC-P, manufactured by Tokuyama Corporation) was coated to the surface of the above plastic lens by using a spin coater (1H-DX2, manufactured by MIKASA) at 70 rpm for 15 seconds and then at 1,000 rpm for 10 seconds. Thereafter, about 2 g of the photochromic composition obtained above was spin coated at 60 rpm for 40 seconds and then at 600 rpm for 10 to 20 seconds to form a photochromic coating layer having a thickness of 40 μm.

The lens coated with the coating agent on the surface was exposed to light from a metal halide lamp having an output of 200 mW/cm$^2$ in a nitrogen gas atmosphere for 90 seconds to cure the coating film. Thereafter, the lens was heated at 110° C. for 1 hour to manufacture a photochromic laminate having a photochromic layer.

The obtained photochromic laminate was used as a sample and the photochromic properties of the laminate were evaluated in the same manner as in Example 4. As for the residual rate, the accelerated deterioration of the photochromic laminate was carried out for 50 hours by means of the X25 xenon weather meter of Suga Test Instruments Co., Ltd. The results are shown in Table 4.

TABLE 4

| Photochromic curable composition | | Photochromic properties | | | |
|---|---|---|---|---|---|
| composition | compound | Maximum absorption wavelength (nm) | Optical color density (—) | Fading speed (sec.) | Residual rate (%) |
| Example 31 | C | Example 14 | 459 564 | 1.08 0.83 | 65 65 | 87 86 |
| Example 32 | C | Example 15 | 461 567 | 1.19 0.92 | 59 60 | 86 87 |
| Comp. Ex. 13 | C | E | 462 569 | 1.03 0.80 | 81 82 | 89 89 |

Comp. Ex.: Comparative Example

The invention claimed is:

1. A chromene compound having an indenonaphthopyran moiety, wherein the indenonaphthopyran moiety has a spiro ring formed together with the 13-position carbon atom at the 13-position and an oligomer chain group selected from the group consisting of a polyalkylene oxide oligomer chain group having at least three recurring units and a polyester oligomer chain group having at least three recurring units, and wherein the chromene compound, which is represented by the following formula (1):

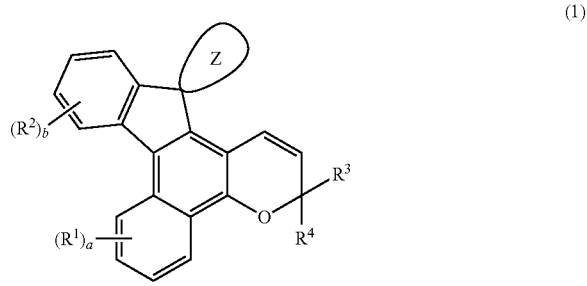

wherein R$^1$ and R$^2$ are each independently the oligomer chain group, hydroxyl group, alkyl group, haloalkyl group, cycloalkyl group which may have a substituent, alkoxy group, amino group, substituted amino group, heterocyclic group which may have a substituent, cyano group, halogen atom, alkylthio group, arylthio group which may have a substituent, nitro group, formyl group, hydroxycarbonyl group, alkylcarbonyl group, alkoxycarbonyl group, aralkyl group which may have a substituent, aralkoxy group which may have a substituent, aryloxy group which may have a substituent, aryl group which may have a substituent, heteroaryl group which may have a substituent, thiol group, alkoxyalkylthio group, haloalkylthio group or cycloalkylthio group which may have a substituent, "a" is an integer of 0 to 4, "b" is an integer of 0 to 4, when "a" is 2 to 4, a plurality of R$^1$'s may be the same or different, when "b" is 2 to 4, a plurality of R$^2$'s may be the same or different, when "a" is 2 to 4 and adjacent R$^1$'s are existent, two adjacent R$^1$'s may form together with two carbon atoms bonded to these R$^1$'s a ring which may include an oxygen atom, carbon atom, sulfur atom or nitrogen atom, and further the ring may have a substituent, when "b" is 2 to 4 and adjacent $R^2$'s are existent, two adjacent $R^2$'s may form together with two carbon atoms bonded to these $R^2$'s a ring which may include an oxygen atom, carbon atom, sulfur atom or nitrogen atom, and further the ring may have a substituent; $R^3$ and $R^4$ are each independently the oligomer chain group, an aryl group which may have a substituent, or heteroaryl group which may have a substituent and at least one of $R^3$ and $R^4$ is the oligomer chain group, the aryl group having the oligomer chain group, or the heteroaryl group having the oligomer chain group; the spiro ring Z represented by the following formula (Z) and bonded to the 13-position of the chromene compound together with the 13-position carbon atom is an aliphatic ring which may have a substituent and has 3 to 20 carbon atoms constituting the ring together with the 13-position carbon atom, condensed polycyclic ring obtained by condensing an aromatic ring or aromatic heterocyclic ring which may have a substituent to the aliphatic ring, heterocyclic ring which may have a substituent and has 3 to 20 atoms constituting the ring together with the 13-position carbon atom, or condensed polycyclic ring obtained by condensing an aromatic ring or aromatic heterocyclic ring which may have a substituent to the heterocyclic ring; and the substituent of each of the groups which may have a substituent may be the oligomer chain group to ensure that the chromene compound has at least one oligomer chain group in the molecule

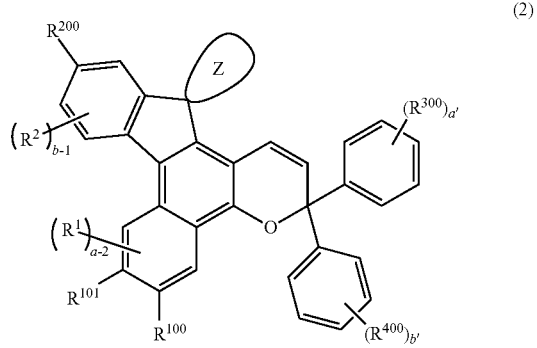

2. The chromene compound according to claim 1, wherein the spiro ring Z represented by the formula (Z) is a ring selected from cyclopentane ring, cyclohexane ring, cycloheptane ring, cyclooctane ring, cyclononane ring, cyclodecane ring, cycloundecane ring, cyclododecane ring and spirodicyclohexane ring, the ring may have 1 to 10 alkyl groups with 1 to 3 carbon atoms or 1 to 10 cycloalkyl groups with 5 to 7 carbon atoms as substituents, or the ring is a ring to which a cycloalkyl group having 5 to 7 carbon atoms may be condensed.

3. The chromene compound according to claim 1, wherein the spiro ring Z represented by the formula (Z) is a ring selected from the following formulas:

[CF3]

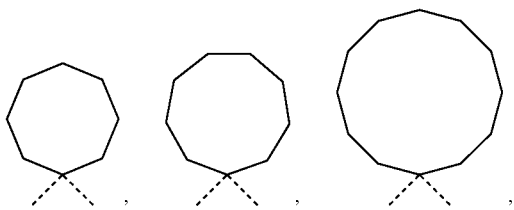

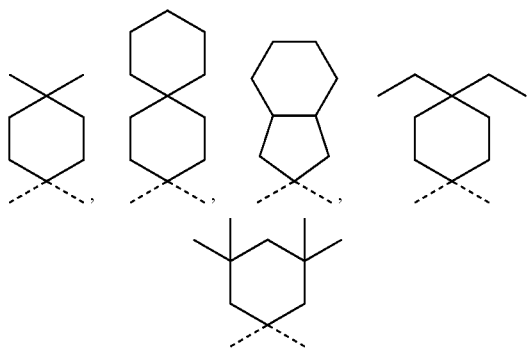

wherein carbon atoms having bonds shown by a dotted line are the 13-position carbon atoms.

4. The chromene compound according to claim 1, which is represented by the following formula (2):

[CF 4]

wherein $R^1$, $R^2$, "a", "b" and spiro ring Z are as defined in the formula (1); $R^{100}$ and $R^{101}$ are each independently the oligomer chain group, hydrogen atom, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group which may have a substituent, cyano group, halogen atom, alkylthio group having 1 to 6 carbon atoms, arylthio group having 6 to 10 carbon atoms which may have a substituent, nitro group, formyl group, hydroxycarbonyl group, alkylcarbonyl group having 2 to 7 carbon atoms, alkoxycarbonyl group having 2 to 7 carbon atoms, aralkyl group having 7 to 11 carbon atoms which may have a substituent, aralkoxy group having 7 to 11 carbon atoms which may have a substituent, aryloxy group having 6 to 12 carbon atoms which may have a substituent, aryl group having 6 to 12 carbon atoms which may have a substituent, heteroaryl group having 3 to 12 carbon atoms which may have a substituent, thiol group, alkoxyalkylthio group having 2 to 9 carbon atoms, haloalkylthio group having 1 to 6 carbon atoms or cycloalkylthio group having 3 to 8 carbon atoms, and $R^{100}$ and $R^{101}$ may form a ring represented by the following formula (3) together;

[CF 5]

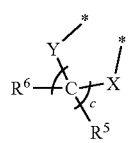
(3)

in the above formula, two asterisk marks represent 6-position or 7-position carbon atom, and either one or both of X and Y are sulfur atoms, methylene groups, oxygen atoms or groups represented by the following formula (4):

[CF 6]

(4)

in the above formula, $R^7$ is the oligomer chain group, hydrogen atom, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, aryl group having 6 to 12 carbon atoms which may have a substituent or heteroaryl group having 3 to 12 carbon atoms which may have a substituents;

$R^5$ and $R^6$ are each independently the oligomer chain group, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group which may have a substituent, cyano group, nitro group, formyl group, hydroxycarbonyl group, alkylcarbonyl group having 2 to 7 carbon atoms, alkoxycarbonyl group having 2 to 7 carbon atoms, halogen atom, aralkyl group having 7 to 11 carbon atoms which may have a substituent, aralkoxy group having 7 to 11 carbon atoms which may have a substituent, aryl group having 6 to 12 carbon atoms which may have a substituent, thiol group, alkylthio group having 1 to 6 carbon atoms, alkoxyalkylthio group having 2 to 9 carbon atoms, haloalkylthio group having 1 to 6 carbon atoms, cycloalkylthio group having 3 to 8 carbon atoms, or arylthio group having 6 to 10 carbon atoms which may have a substituent, and $R^5$ and $R^6$ may form an aliphatic ring which may have a substituent together with carbon atoms bonded thereto, and "c" is an integer of 1 to 3;

$R^{200}$ is the oligomer chain group, hydrogen atom, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group which may have a substituent, cyano group, nitro group, formyl group, hydroxycarbonyl group, alkylcarbonyl group having 2 to 7 carbon atoms, alkoxycarbonyl group having 2 to 7 carbon atoms, halogen atom, aralkyl group having 7 to 11 carbon atoms which may have a substituent, aralkoxy group having 7 to 11 carbon atoms which may have a substituent, aryl group having 6 to 12 carbon atoms which may have a substituent, thiol group, alkylthio group having 1 to 6 carbon atoms, alkoxyalkylthio group having 2 to 9 carbon atoms, haloalkylthio group having 1 to 6 carbon atoms, cycloalkylthio group having 3 to 8 carbon atoms, or arylthio group having 6 to 10 carbon atoms which may have a substituent; $R^{300}$ and $R^{400}$ are each independently the oligomer chain group, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group which may have a substituent, cyano group, halogen atom, alkylthio group having 1 to 6 carbon atoms, or arylthio group having 6 to 10 carbon atoms which may have a substituent and at least one of $R^{300}$ and $R^{400}$ is the oligomer chain group; "a'" is an integer of 0 to 5, when "a'" is 2 or more, $R^{300}$'s may be the same or different, "b" is an integer of 0 to 5, when "b" is 2 or more, $R^{400}$'s may be the same or different; and the substituent of each of the groups which may have a substituent may be the oligomer chain group to ensure that the chromene compound has at least one oligomer chain group in the molecule.

5. The chromene compound according to claim 1, wherein the oligomer chain group is selected from groups represented by the following formulas (5a) to (5c) or a combination thereof:

[CF 7]

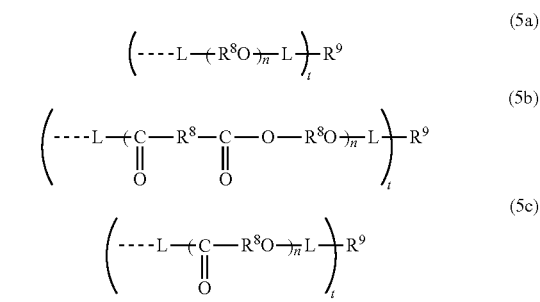

wherein $R^1$ is a linear or branched alkylene group having 1 to 20 carbon atoms, when a plurality of $R^8$'s are contained in the same molecule, $R^8$'s may be the same or different, "n" indicates the number of the recurring units of the oligomer chain group and is an integer of 3 to 200, and a plurality of divalent groups of the recurring units may be the same or different, L is a divalent bond group represented by the following formula (6):

[CF 8]

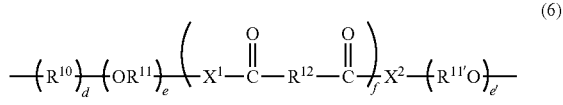
(6)

in the above formula, $R^{10}$ is a divalent group, which is a linear or branched alkylene group having 1 to 20 carbon atoms, cycloalkyl group which may have a substituent with 3 to 12 carbon atoms forming a ring, aryl group which may have a substituent with 6 to 12 carbon atoms forming a ring, or heterocyclic group which may have a substituent with 3 to 12 atoms forming a ring, $R^{11}$ and $R^{11'}$ are each independently a divalent group, which is a linear or branched alkylene group having 1 to 20 carbon atoms, cycloalkyl group which may have a substituent with 3 to 12 carbon atoms forming a ring, or aryl group which may have a substituent with 6 to 12 carbon atoms forming a ring, $R^{12}$ is a divalent group, which is a linear or branched alkylene group having 1 to 20 carbon atoms, cycloalkyl group which may have a substituent with 3 to 12 carbon atoms forming a ring, or aryl group which may have a substituent with 6 to 12 carbon atoms forming a ring, $X^1$ and $X^2$ are each independently a divalent group, which is a single bond, O, S, amino group, substituted amino group, (thio)amide group or (thio)ester group, "d" is an integer of 0 to 50, "e" and "e'" are each independently an integer of 0 to 50, "f" is an integer of 0 to 50, when "d" is 2 or more, a plurality of $R^{10}$'s may be the same or different, and when "e" and "e'" are each 2 or more, an "e" number of divalent groups and an "e'" number of divalent groups may be the same or different, and when "f" is 2 or more, an "f" number of divalent groups may be the same or different;

a plurality of L's may be the same or different, the broken line represents a bond to the indenonaphthopyran moiety, "t" indicates the number of the oligomer chain groups and is an integer of 1 to 10, when "t" is 1, $R^9$ is a hydrogen atom or alkyl group having 1 to 20 carbon atoms, when "t" is 2, $R^9$ is a bond or divalent organic residue, and when "t" is 3 to 10, $R^9$ is a "t" number of organic residues.

6. The chromene compound according to claim 5, wherein the bond group L is a group selected from the following formulas:

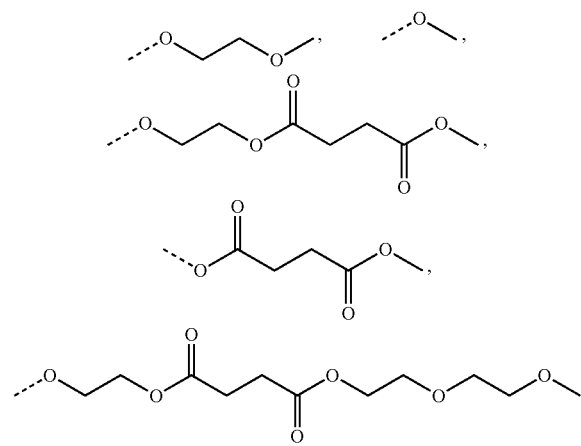

wherein the broken line represents a bond to the indenonaphthopyran moiety.

7. A photochromic curable composition comprising the chromene compound of claim 1 and a polymerizable compound.

8. A photochromic optical article obtained by polymerizing the photochromic curable composition of claim 7.

9. A polymer molded body containing the chromene compound of claim 1 dispersed therein.

10. An optical article covered with a polymer film containing the chromene compound of claim 1 dispersed therein.

11. The chromene compound according to claim 2, wherein the spiro ring Z represented by the formula (Z) is a ring selected from the following formulas:

[CF 3]

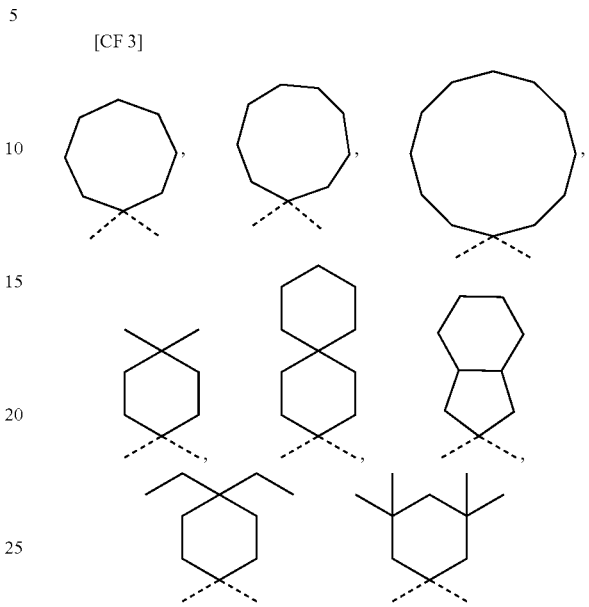

wherein carbon atoms having bonds shown by a dotted line are the 13-position carbon atoms.

12. The chromene compound according to claim 2, which is represented by the following formula (2):

[CF 4]

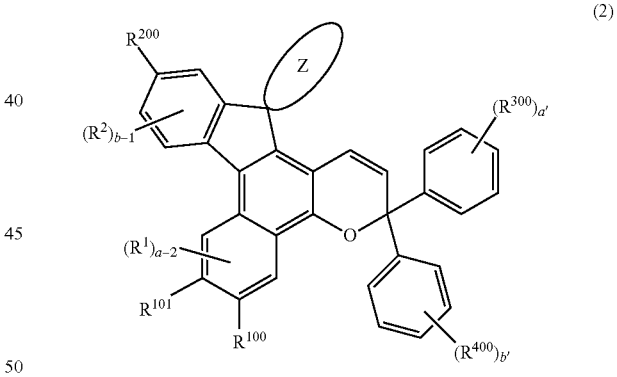

(2)

wherein $R^1$, $R^2$, "a", "b" and Spiro ring Z are as defined in the formula (1); $R^{100}$ and $R^{101}$ are each independently the oligomer chain group, hydrogen atom, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group which may have a substituent, cyano group, halogen atom, alkylthio group having 1 to 6 carbon atoms, arylthio group having 6 to 10 carbon atoms which may have a substituent, nitro group, formyl group, hydroxycarbonyl group, alkylcarbonyl group having 2 to 7 carbon atoms, alkoxycarbonyl group having 2 to 7 carbon atoms, aralkyl group having 7 to 11 carbon atoms which may have a substituent, aralkoxy group having 7 to 11 carbon atoms which may have a substituent, aryloxy group having 6 to 12 carbon atoms which may have a substituent, aryl group having 6 to 12 carbon atoms which may have a substituent, heteroaryl group having 3 to 12 carbon atoms which may have a substituent, thiol group, alkoxyalkylthio group having 2 to 9 carbon atoms, haloalkylthio group having 1 to 6 carbon atoms or cycloalkylthio group having 3 to 8 carbon atoms, and $R^{100}$ and $R^{101}$ may form a ring represented by the following formula (3) together;

[CF 5]

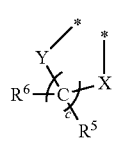

(3)

in the above formula, two asterisk marks represent 6-position or 7-position carbon atom, and either one or both of X and Y are sulfur atoms, methylene groups, oxygen atoms or groups represented by the following formula (4):

[CF 6]

(4)

in the above formula, $R^7$ is the oligomer chain group, hydrogen atom, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, aryl group having 6 to 12 carbon atoms which may have a substituent or heteroaryl group having 3 to 12 carbon atoms which may have a substituents;

$R^5$ and $R^6$ are each independently the oligomer chain group, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group which may have a substituent, cyano group, nitro group, formyl group, hydroxycarbonyl group, alkylcarbonyl group having 2 to 7 carbon atoms, alkoxycarbonyl group having 2 to 7 carbon atoms, halogen atom, aralkyl group having 7 to 11 carbon atoms which may have a substituent, aralkoxy group having 7 to 11 carbon atoms which may have a substituent, aryl group having 6 to 12 carbon atoms which may have a substituent, thiol group, alkylthio group having 1 to 6 carbon atoms, alkoxyalkylthio group having 2 to 9 carbon atoms, haloalkylthio group having 1 to 6 carbon atoms, cycloalkylthio group having 3 to 8 carbon atoms, or arylthio group having 6 to 10 carbon atoms which may have a substituent, and $R^5$ and $R^6$ may form an aliphatic ring which may have a substituent together with carbon atoms bonded thereto, and "c" is an integer of 1 to 3;

$R^{200}$ is the oligomer chain group, hydrogen atom, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group which may have a substituent, cyano group, nitro group, formyl group, hydroxycarbonyl group, alkylcarbonyl group having 2 to 7 carbon atoms, alkoxycarbonyl group having 2 to 7 carbon atoms, halogen atom, aralkyl group having 7 to 11 carbon atoms which may have a substituent, aralkoxy group having 7 to 11 carbon atoms which may have a substituent, aryl group having 6 to 12 carbon atoms which may have a substituent, thiol group, alkylthio group having 1 to 6 carbon atoms, alkoxyalkylthio group having 2 to 9 carbon atoms, haloalkylthio group having 1 to 6 carbon atoms, cycloalkylthio group having 3 to 8 carbon atoms, or arylthio group having 6 to 10 carbon atoms which may have a substituent; $R^{300}$ and $R^{400}$ are each independently the oligomer chain group, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group which may have a substituent, cyano group, halogen atom, alkylthio group having 1 to 6 carbon atoms, or arylthio group having 6 to 10 carbon atoms which may have a substituent and at least one of $R^{300}$ and $R^{400}$ is the oligomer chain group; "a'" is an integer of 0 to 5, when "a'" is 2 or more, $R^{300}$'s may be the same or different, "b'" is an integer of 0 to 5, when "b'" is 2 or more, $R^{400}$'s may be the same or different; and the substituent of each of the groups which may have a substituent may be the oligomer chain group to ensure that the chromene compound has at least one oligomer chain group in the molecule.

13. The chromene compound according to claim 3, which is represented by the following formula (2):

[CF 4]

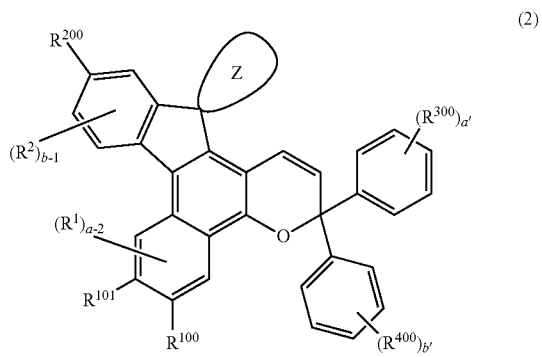

(2)

wherein $R^1$, $R^2$, "a", "b" and spiro ring Z are as defined in the formula (1); $R^{100}$ and $R^{101}$ are each independently the oligomer chain group, hydrogen atom, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group which may have a substituent, cyano group, halogen atom, alkylthio group having 1 to 6 carbon atoms, arylthio group having 6 to 10 carbon atoms which may have a substituent, nitro group, formyl group, hydroxycarbonyl group, alkylcarbonyl group having 2 to 7 carbon atoms, alkoxycarbonyl group having 2 to 7 carbon atoms, aralkyl group having 7 to 11 carbon atoms which may have a substituent, aralkoxy group having 7 to 11 carbon atoms which may have a substituent, aryloxy group having 6 to 12 carbon atoms which may have a substituent, aryl group having 6 to 12 carbon atoms which may have a substituent, heteroaryl group having 3 to 12 carbon atoms which may have a substituent, thiol group, alkoxyalkylthio group having 2 to 9 carbon atoms, haloalkylthio group having 1 to 6 carbon atoms or cycloalkylthio group having 3 to 8 carbon atoms, and $R^{100}$ and $R^{101}$ may form a ring represented by the following formula (3) together;

[CF 5]

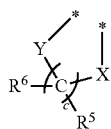

(3)

in the above formula, two asterisk marks represent 6-position or 7-position carbon atom, and either one or both of X and Y are sulfur atoms, methylene groups, oxygen atoms or groups represented by the following formula (4):

[CF 6]

(4)

in the above formula, $R^7$ is the oligomer chain group, hydrogen atom, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, aryl group having 6 to 12 carbon atoms which may have a substituent or heteroaryl group having 3 to 12 carbon atoms which may have a substituent;

$R^5$ and $R^6$ are each independently the oligomer chain group, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group which may have a substituent, cyano group, nitro group, formyl group, hydroxycarbonyl group, alkylcarbonyl group having 2 to 7 carbon atoms, alkoxycarbonyl group having 2 to 7 carbon atoms, halogen atom, aralkyl group having 7 to 11 carbon atoms which may have a substituent, aralkoxy group having 7 to 11 carbon atoms which may have a substituent, aryl group having 6 to 12 carbon atoms which may have a substituent, thiol group, alkylthio group having 1 to 6 carbon atoms, alkoxyalkylthio group having 2 to 9 carbon atoms, haloalkylthio group having 1 to 6 carbon atoms, cycloalkylthio group having 3 to 8 carbon atoms, or arylthio group having 6 to 10 carbon atoms which may have a substituent, and $R^5$ and $R^6$ may form an aliphatic ring which may have a substituent together with carbon atoms bonded thereto, and "c" is an integer of 1 to 3;

$R^{200}$ is the oligomer chain group, hydrogen atom, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group which may have a substituent, cyano group, nitro group, formyl group, hydroxycarbonyl group, alkylcarbonyl group having 2 to 7 carbon atoms, alkoxycarbonyl group having 2 to 7 carbon atoms, halogen atom, aralkyl group having 7 to 11 carbon atoms which may have a substituent, aralkoxy group having 7 to 11 carbon atoms which may have a substituent, aryl group having 6 to 12 carbon atoms which may have a substituent, thiol group, alkylthio group having 1 to 6 carbon atoms, alkoxyalkylthio group having 2 to 9 carbon atoms, haloalkylthio group having 1 to 6 carbon atoms, cycloalkylthio group having 3 to 8 carbon atoms, or arylthio group having 6 to 10 carbon atoms which may have a substituent; $R^{300}$ and $R^{400}$ are each independently the oligomer chain group, hydroxyl group, alkyl group having 1 to 6 carbon atoms, haloalkyl group having 1 to 6 carbon atoms, cycloalkyl group having 3 to 8 carbon atoms, alkoxy group having 1 to 6 carbon atoms, amino group, substituted amino group, heterocyclic group which may have a substituent, cyano group, halogen atom, alkylthio group having 1 to 6 carbon atoms, or arylthio group having 6 to 10 carbon atoms which may have a substituent and at least one of $R^{300}$ and $R^{400}$ is the oligomer chain group; "a" is an integer of 0 to 5, when "a" is 2 or more, $R^{300}$'s may be the same or different, "b" is an integer of 0 to 5, when "b" is 2 or more, $R^{400}$'s may be the same or different; and the substituent of each of the groups which may have a substituent may be the oligomer chain group to ensure that the chromene compound has at least one oligomer chain group in the molecule.

14. The chromene compound according to claim 2, wherein the oligomer chain group is selected from groups represented by the following formulas (5a) to (5c) or a combination thereof:

[CF 7]

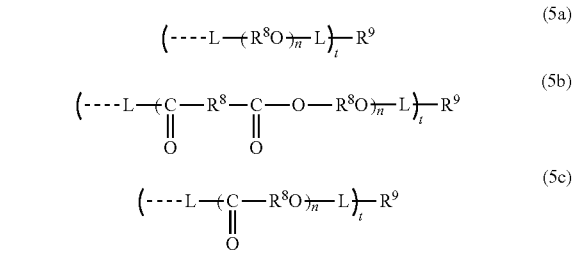

wherein $R^8$ is a linear or branched alkylene group having 1 to 20 carbon atoms, when a plurality of $R^8$'s are contained in the same molecule, $R^8$'s may be the same or different, "n" indicates the number of the recurring units of the oligomer chain group and is an integer of 3 to 200, and a plurality of divalent groups of the recurring units may be the same or different, L is a divalent bond group represented by the following formula (6):

[CF 8]

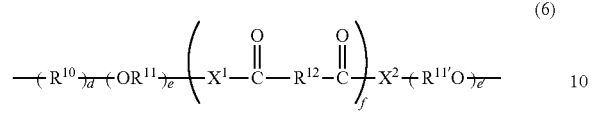
(6)

in the above formula, $R^{10}$ is a divalent group, which is a linear or branched alkylene group having 1 to 20 carbon atoms, cycloalkyl group which may have a substituent with 3 to 12 carbon atoms forming a ring, aryl group which may have a substituent with 6 to 12 carbon atoms forming a ring, or heterocyclic group which may have a substituent with 3 to 12 atoms forming a ring, $R^{11}$ and $R^{11'}$ are each independently a divalent group, which is a linear or branched alkylene group having 1 to 20 carbon atoms, cycloalkyl group which may have a substituent with 3 to 12 carbon atoms forming a ring, or aryl group which may have a substituent with 6 to 12 carbon atoms forming a ring, $R^{12}$ is a divalent group, which is a linear or branched alkylene group having 1 to 20 carbon atoms, cycloalkyl group which may have a substituent with 3 to 12 carbon atoms forming a ring, or aryl group which may have a substituent with 6 to 12 carbon atoms forming a ring, $X^1$ and $X^2$ are each independently a divalent group, which is a single bond, O, S, amino group, substituted amino group, (thio)amide group or (thio)ester group, "d" is an integer of 0 to 50, "e" and "e'" are each independently an integer of 0 to 50, "f" is an integer of 0 to 50, when "d" is 2 or more, a plurality of $R^{10}$'s may be the same or different, and when "e" and "e'" are each 2 or more, an "e" number of divalent groups and an "e'" number of divalent groups may be the same or different, and when "f" is 2 or more, an "f" number of divalent groups may be the same or different;

a plurality of L's may be the same or different, the broken line represents a bond to the indenonaphthopyran moiety, "t" indicates the number of the oligomer chain groups and is an integer of 1 to 10, when "t" is 1, $R^9$ is a hydrogen atom or alkyl group having 1 to 20 carbon atoms, when "t" is 2, $R^9$ is a bond or divalent organic residue, and when "t" is 3 to 10, $R^9$ is a "t" number of organic residues.

15. The chromene compound according to claim 3, wherein the oligomer chain group is selected from groups represented by the following formulas (5a) to (5c) or a combination thereof:

[CF 7]

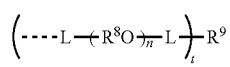
(5a)

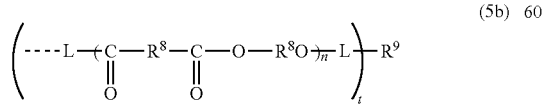
(5b)

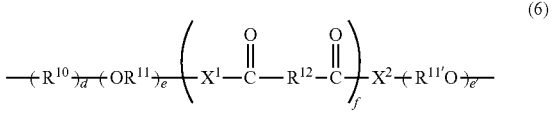
(5c)

wherein $R^8$ is a linear or branched alkylene group having 1 to 20 carbon atoms, when a plurality of $R^8$'s are contained in the same molecule, $R^8$'s may be the same or different, "n" indicates the number of the recurring units of the oligomer chain group and is an integer of 3 to 200, and a plurality of divalent groups of the recurring units may be the same or different, L is a divalent bond group represented by the following formula (6):

[CF 8]

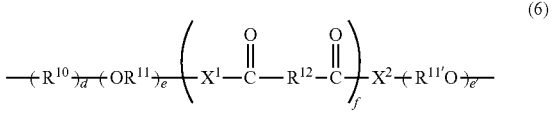
(6)

in the above formula, $R^{10}$ is a divalent group, which is a linear or branched alkylene group having 1 to 20 carbon atoms, cycloalkyl group which may have a substituent with 3 to 12 carbon atoms forming a ring, aryl group which may have a substituent with 6 to 12 carbon atoms forming a ring, or heterocyclic group which may have a substituent with 3 to 12 atoms forming a ring, $R^{11}$ and $R^{11'}$ are each independently a divalent group, which is a linear or branched alkylene group having 1 to 20 carbon atoms, cycloalkyl group which may have a substituent with 3 to 12 carbon atoms forming a ring, or aryl group which may have a substituent with 6 to 12 carbon atoms forming a ring, $R^{12}$ is a divalent group, which is a linear or branched alkylene group having 1 to 20 carbon atoms, cycloalkyl group which may have a substituent with 3 to 12 carbon atoms forming a ring, or aryl group which may have a substituent with 6 to 12 carbon atoms forming a ring, $X^1$ and $X^2$ are each independently a divalent group, which is a single bond, O, S, amino group, substituted amino group, (thio)amide group or (thio)ester group, "d" is an integer of 0 to 50, "e" and "e'" are each independently an integer of 0 to 50, "f" is an integer of 0 to 50, when "d" is 2 or more, a plurality of $R^{10}$'s may be the same or different, and when "e" and "e'" are each 2 or more, an "e" number of divalent groups and an "e'" number of divalent groups may be the same or different, and when "f" is 2 or more, an "f" number of divalent groups may be the same or different;

a plurality of L's may be the same or different, the broken line represents a bond to the indenonaphthopyran moiety, "t" indicates the number of the oligomer chain groups and is an integer of 1 to 10, when "t" is 1, $R^9$ is a hydrogen atom or alkyl group having 1 to 20 carbon atoms, when "t" is 2, $R^9$ is a bond or divalent organic residue, and when "t" is 3 to 10, $R^9$ is a "t" number of organic residues.

* * * * *